(12) United States Patent
Welker et al.

(10) Patent No.: US 9,550,791 B2
(45) Date of Patent: Jan. 24, 2017

(54) FUNCTIONNALIZED BENZODITHIOPHENE POLYMERS FOR ELECTRONIC APPLICATION

(71) Applicant: BASF SE, Ludwigshafen (DE)

(72) Inventors: Matthias Welker, St. Louis (FR); Mathieu G. R. Turbiez, Rixheim (FR); Natalia Chebotareva, Hagenthal le Bas (FR); Hans Jürg Kirner, Basel (CH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/649,352

(22) PCT Filed: Dec. 2, 2013

(86) PCT No.: PCT/EP2013/075263
§ 371 (c)(1),
(2) Date: Jun. 3, 2015

(87) PCT Pub. No.: WO2014/086722
PCT Pub. Date: Jun. 12, 2014

(65) Prior Publication Data
US 2015/0333265 A1 Nov. 19, 2015

Related U.S. Application Data

(60) Provisional application No. 61/732,951, filed on Dec. 4, 2012.

(30) Foreign Application Priority Data

Dec. 4, 2012 (EP) .................................... 12195408

(51) Int. Cl.
| | | |
|---|---|---|
| C07F 5/04 | (2006.01) |
| C07F 7/08 | (2006.01) |
| C08G 61/12 | (2006.01) |
| C07D 495/04 | (2006.01) |
| H01L 51/00 | (2006.01) |
| C07F 5/02 | (2006.01) |
| C09B 57/00 | (2006.01) |
| C09B 69/00 | (2006.01) |
| C09B 69/10 | (2006.01) |

(Continued)

(52) U.S. Cl.
CPC ............ *C07D 495/04* (2013.01); *C07F 5/025* (2013.01); *C07F 7/0814* (2013.01); *C08G 61/126* (2013.01); *C09B 57/00* (2013.01); *C09B 57/004* (2013.01); *C09B 69/008* (2013.01); *C09B 69/102* (2013.01); *C09B 69/109* (2013.01); *H01L 51/0036* (2013.01); *H01L 51/0037* (2013.01); *H01L 51/0043* (2013.01); *C08G 2261/124* (2013.01); *C08G 2261/146* (2013.01); *C08G 2261/1426* (2013.01); *C08G 2261/1428* (2013.01); *C08G 2261/1432* (2013.01); *C08G 2261/3243* (2013.01); *C08G 2261/344* (2013.01); *C08G 2261/411* (2013.01); *C08G 2261/51* (2013.01); *C08G 2261/91* (2013.01); *C08G 2261/92* (2013.01); *H01L 51/0545* (2013.01); *H01L 51/4253* (2013.01); *Y02E 10/549* (2013.01)

(58) Field of Classification Search
CPC ...... C07F 5/025; C07F 7/0814; H01L 51/0036; C08G 61/126; C07D 495/04
See application file for complete search history.

(56) References Cited

U.S. PATENT DOCUMENTS

| | | |
|---|---|---|
| 2009/0065770 A1 | 3/2009 | Miura et al. |
| 2011/0006287 A1 | 1/2011 | You et al. |
| 2011/0284826 A1 | 11/2011 | Hayoz et al. |

(Continued)

FOREIGN PATENT DOCUMENTS

| | | |
|---|---|---|
| CN | 102329413 A | 1/2012 |
| EP | 2006291 B1 | 11/2010 |

(Continued)

OTHER PUBLICATIONS

Wiersema et al. Acta Chemica Scandinavica, 1970, 24, 2653-2655.*
Wiersema et al., "Thiophene Analogues of Fluorene IV. An Unusual Behavior of a Cyclopentadithiophenone in the Reaction with Dienophiles", *Acta Chem. Scand.*, vol. 24, No. 7, pp. 2653-2655 (1970).

(Continued)

*Primary Examiner* — Matthew Coughlin
(74) *Attorney, Agent, or Firm* — Drinker Biddle & Reath LLP

(57) ABSTRACT

The present invention relates to polymers comprising a repeating unit of the formula (I), and their use as organic semiconductor in organic electronic devices, especially in organic photovoltaics and photodiodes, or in a device containing a diode and/or an organic field effect transistor. The polymers according to the invention can have excellent solubility in organic solvents and excellent film-forming properties. In addition, high efficiency of energy conversion, excellent field-effect mobility, good on/off current ratios and/or excellent stability can be observed, when the polymers according to the invention are used in organic field effect transistors, organic photovoltaics (solar cells) and photodiodes.

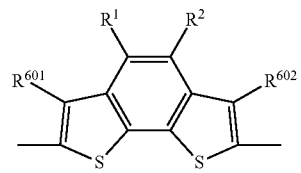

(I)

14 Claims, No Drawings

(51) Int. Cl.
  *H01L 51/42* (2006.01)
  *H01L 51/05* (2006.01)

(56) References Cited

U.S. PATENT DOCUMENTS

| | | |
|---|---|---|
| 2013/0072654 A1 | 3/2013 | Zhou et al. |
| 2013/0085249 A1 | 4/2013 | Zhou et al. |
| 2013/0102746 A1 | 4/2013 | Zhou et al. |
| 2013/0165655 A1 | 6/2013 | Zhou et al. |

FOREIGN PATENT DOCUMENTS

| | | |
|---|---|---|
| EP | 2578614 A1 | 4/2013 |
| WO | WO-2007/105386 A1 | 9/2007 |
| WO | WO-2010/136353 A1 | 12/2010 |
| WO | WO-2010/136401 A2 | 12/2010 |
| WO | WO-2011/002927 A2 | 1/2011 |
| WO | WO-2011/011545 A1 | 1/2011 |
| WO | WO-2011/025454 A1 | 3/2011 |
| WO | WO-2011/147067 A1 | 12/2011 |
| WO | WO-2011/153694 A1 | 12/2011 |
| WO | WO-2011/160302 A1 | 12/2011 |
| WO | WO-2011156478 A2 | 12/2011 |
| WO | WO-2012/031404 A1 | 3/2012 |
| WO | WO 2013/150005 A1 | 10/2013 |

OTHER PUBLICATIONS

Citterio et al., Oxidative Dimerization of Diethyl 3-Thienylmalonate by High Valent Metal Salts. Synthesis of Benzo[1,2-b:4,5-b']dithiophene Derivatives, *Tetrahedron*, vol. 52, No. 41, pp. 13227-13242 (1996).

Dahlmann et al., "The Diyne Reaction of 3,3'-Bis(phenylethynyl)-2,2'-bithiophene Derivatives via Rhodium Complexes: A Novel Approach to Condensed Benzo[2,1-*b* :3,4-*b*']dithiophenes", *Helvetica Chimica. Acta*, vol. 80, pp. 111-120 (1997).

Huo et al., "Bandgap and Molecular Level Control of the Low-Bandgap Polymers Based on 3,6-Dithiophen-2-yl-2,5-dihydropyrrolo[3,4-*c*]pyrrole-1,4-dione toward Highly Efficient Polymer Solar Cells", *Macromolecules*, vol. 42, pp. 6564-6571 (2009).

Yuan et al., "Benzo[2,1-*b*;3,4-*b'*]dithiophene-Based Low-Bandgap Polymers for Photovoltaic Applications", *Journal of Polymer Science: Part A: Polymer Chemistry*, vol. 49, pp. 701-711 (Published online—Wiley Online Library) DOI: 10.1002/pola.24481, Dec. 3, 2010.

Lei et al., "Systematic Investigation of Isoindigo-Based Polymeric Field-Effect Transistors: Design Strategy and Impact of Polymer Symmetry and Backbone Curvature", *Chem. Mater.*, vol. 24, pp. 1762-1770 (2012).

International Search Report for PCT/EP2013/075263 mailed Jan. 31, 2014.

\* cited by examiner

FUNCTIONNALIZED BENZODITHIOPHENE POLYMERS FOR ELECTRONIC APPLICATION

CROSS-REFERENCE TO RELATED APPLICATIONS

This application is a national stage application (under 35 U.S.C. §371) of PCT/EP2013/075263, filed Dec. 2, 2013, which claims benefit of European Application No. 12195408.5, filed Dec. 4, 2012, and U.S. Application No. 61/732,951, filed Dec. 4, 2012, all of which are incorporated herein by reference in their entirety.

The present invention relates to polymers comprising a repeating unit of the formula (I) and their use as organic semiconductor in organic electronic devices, especially in organic photovoltaics (solar cells) and photodiodes, or in a device containing a diode and/or an organic field effect transistor. The polymers according to the invention can have excellent solubility in organic solvents and excellent film-forming properties. In addition, high efficiency of energy conversion, excellent field-effect mobility, high open-circuit voltages ($V_{oc}$), good on/off current ratios and/or excellent stability can be observed, when the polymers according to the invention are used in organic field effect transistors, organic photovoltaics (solar cells) and photodiodes.

WO2010136401 relates to polycyclic dithiophenes of the following formula

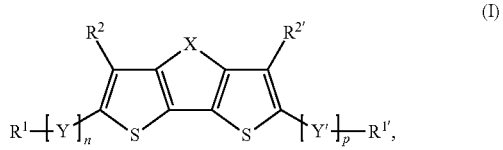

wherein $R^1$ and $R^{1'}$ independently of each other are H or a substituent, halogen or $SiR^6R^4R^5$;

$R^2$ and $R^{2'}$ may be the same or different and are selected from $C_1$-$C_{25}$alkyl, $C_3$-$C_{12}$cycloalkyl, $C_2$-$C_{25}$alkenyl, $C_2$-$C_{25}$alkynyl, $C_4$-$C_{25}$aryl, $C_5$-$C_{25}$alkylaryl or $C_5$-$C_{25}$aralkyl, each of which is unsubstituted or substituted, and if $R^3$ and $R^{3'}$ within the definition of X together complete a ring structure, or X is a bridging group conforming to one of the formulae

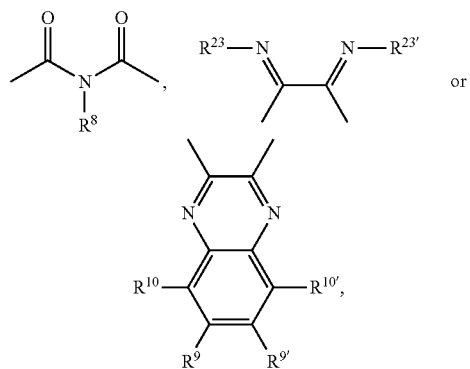

$R^2$ and/or $R^{2'}$ may also be halogen or hydrogen;

X is a divalent linking group selected from

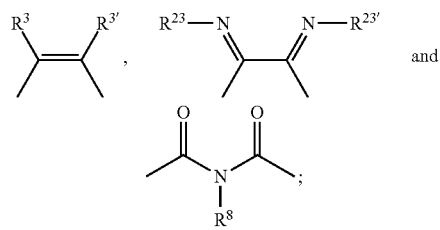

Y and Y' independently are selected from

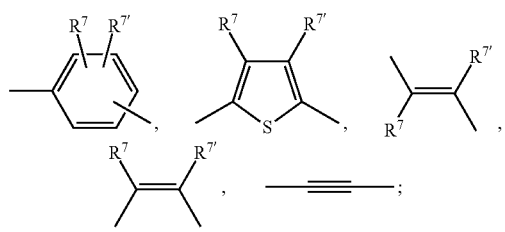

n and p independently range from 0 to 6;

$R^3$ and $R^{3'}$ independently are hydrogen or a substituent, or are amino, or together, with the carbon atoms they are attached to, complete a 5- or 6-membered unsubstituted or substituted hydrocarbon ring, or a 5-membered unsubstituted or substituted heterocyclic ring comprising at least one hetero atom selected from N, O, or S; as well as oligomers, polymers or copolymers comprising at least 2 structural units of the formula

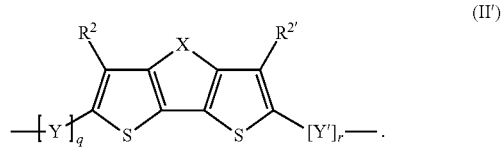

The substances described in WO2010136401 are used in organic field effect transistors, organic photovoltaics (solar cells) and photodiodes.

WO2011002927 relates to a (copolymer) composition comprising at least one copolymer comprising at least one bithiophene repeat unit represented by formula

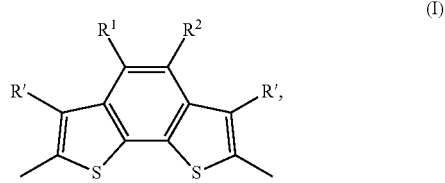

wherein $R_1$, $R_2$ and R' are solubilizing groups or hydrogen. In addition, polymers comprising a bithiophene repeating unit are described in EP2006291, US20110006287 and WO2011025454.

A. K. Wiersema and S. Gronowitz, describe in Acta Chemica Scandinavica 24 (1970) 2653-2655 a procedure for the preparation of the following compound:

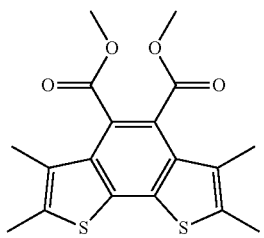

A. Citterio, et al., Tetrahedron 52 (1996) 13227-13242 disclose the preparation of the following compound:

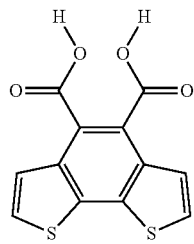 [SMILES: O=C(O)c1c(C(=O)O)c2ccsc2c2sccc12]

U. Dahlmann and R. Neidlein, Helvetica Chimica Acta 80 (1997) 111-120 disclose a synthetic procedure for the preparation of the Following compound:

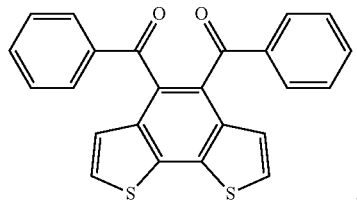

WO2007105386 discloses fused ring compounds exhibiting sufficient charge transport property while having excellent solubility in a solvent. Specifically disclosed is a fused ring compound represented by the general formula A12 ($R^{11}$, $R^{12}$=H, $C_{1-20}$alkyl, alkoxy, alkylthio, alkylamino, alkoxycarbonyl, aryl optionally having a $C_{6-60}$substituent, heterocyclic optionally having a $C_{4-60}$ substituent, cyano group, provided that at least one of $R^{11}$ and $R^{12}$ is not a H atom; $R^{13}$, $R^{14}$=monovalent group; n, m=0-2; and $Y^{11}$, $Y^{12}$=divalent group containing S, O, Se, Te).

A12

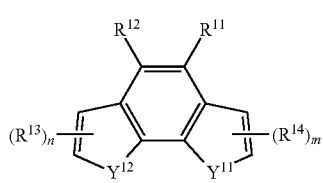

In addition, WO2007105386 describes polymers comprising a repeating unit of formula B1:

B1

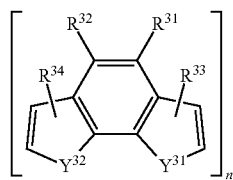

wherein $R^{31}$ and $R^{32}$ each independently represent an hydrogen atom, an alkyl group having 1 to 20 carbon atoms, an alkoxy group, an alkylthio group, an alkylamino group, an alkoxycarbonyl group, an optionally substituted aryl group having 6 to 60 carbon atoms, an optionally substituted heterocyclic group having 4 to 60 carbon atoms, or a cyano group, provided that at least one of $R^{31}$ and $R^{32}$ is not an hydrogen atom. $R^{33}$ and $R^{34}$ are a hydrogen atom or a monovalent group; $Y^{31}$ and $Y^{32}$ are a divalent group containing S, O, Se, Te). The use of those materials in thin film devices, especially transistors, is also reported. The Examples are limited to compounds, wherein $R^{31}$ and $R^{32}$ are alkyl and thin film devices being transistors.

L. Huo et al., Macromolecules (42) 2009 6564-6571 reports the preparation of the following polymer and its application in OPV devices, wherein a maximum PCE of 4.45% with a $V_{oc}$ of 0.72 V was obtained.

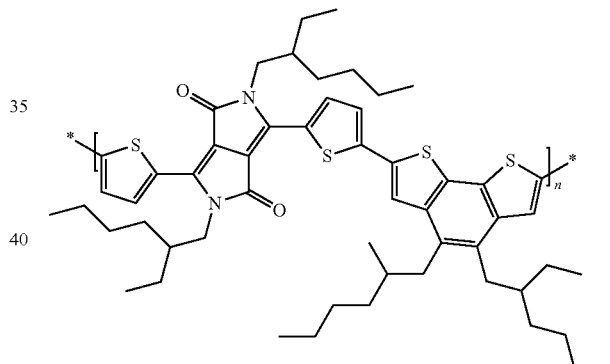

WO2010136401 relates to polycyclic dithiophenes of the following formula, their polymers, and use in semiconductors.

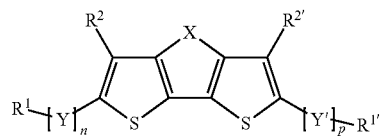

$R^1$ and $R^{1'}$ independently of each other are H or a substituent, halogen or $SiR^6R^4R^5$; $R^2$ and $R^{2'}$, may be the same or different and are selected from $C_1$-$C_{25}$alkyl, $C_3$-$C_{12}$cycloalkyl, $C_2$-$C_{25}$alkenyl, $C_2$-$C_{25}$alkynyl, $C_4$-$C_{25}$aryl, $C_5$-$C_{25}$alkylaryl or $C_5$-$C_{25}$aralkyl, each of which is unsubstituted or substituted, $R^2$ and/or $R^{2'}$ may be halogen or hydrogen; X is a divalent linking group selected from

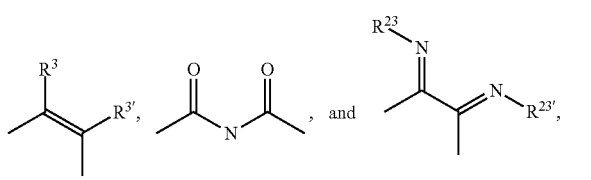

Y and Y' independently are divalent unsaturated groups; n and p independently range from 0 to 6; $R^3$ and $R^{3'}$ independently are a hydrogen atom or a substituent, or are amino, or together, with the carbon atoms they are attached to, complete a 5- or 6-membered unsubstituted or substituted hydrocarbon ring, or a 5-membered unsubstituted or substituted heterocyclic ring comprising at least one heteroatom selected from N, S, O, and to corresponding oligomers and (co)polymers.

WO2010136353 relates to diketopyrrolopyrrole polymers and their use in organic semiconductor devices. In particular the following polymers are explicitly disclosed:

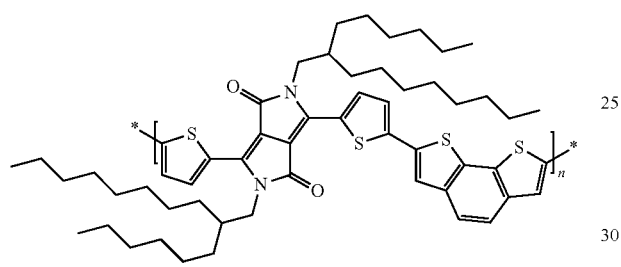

M. Yuan et al.; Journal of Polymer Science, Part A: Polymer Chemistry 49 (2011) 701-711 disclose the preparation of the following polymers (PBDPDPP, PBDPBT, PBDPQU, PBDPTP), and their application in OPV devices, reaching PCE up to 1.11%.

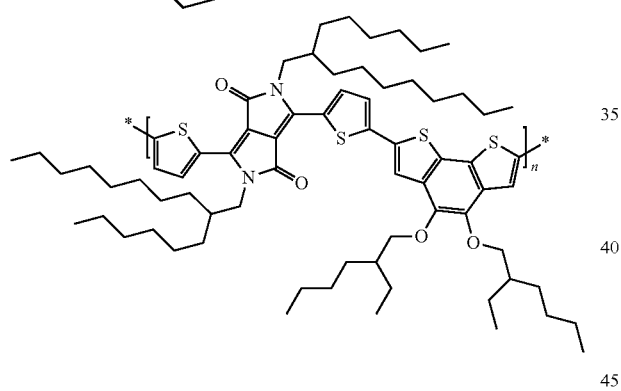

PBDPDPP

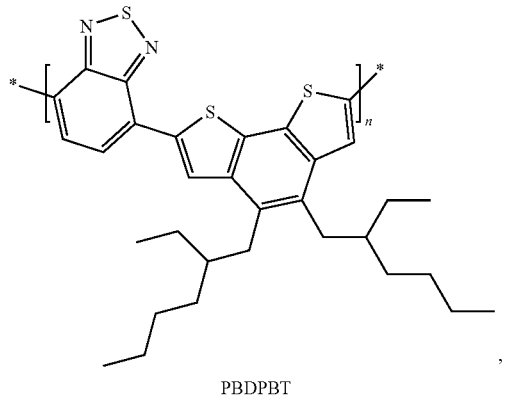

PBDPBT

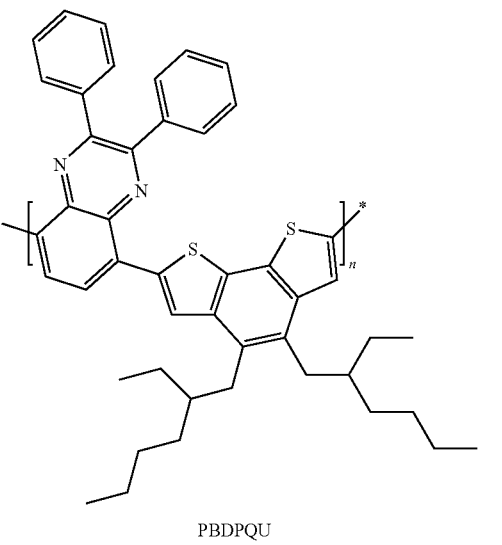

PBDPQU and

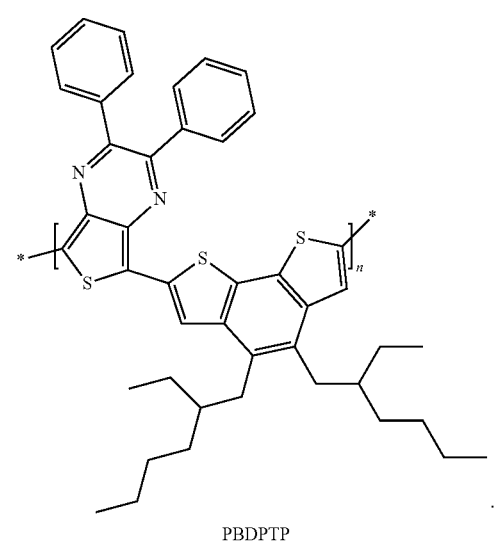

PBDPTP

US20110006287 and WO2011156478 relate to fused ring polymers with tunable band gaps for photonic and electronic applications. In particular claims include copolymers comprising at least one donor and one acceptor monomer, said donor monomer can consist—among others—of the following unit:

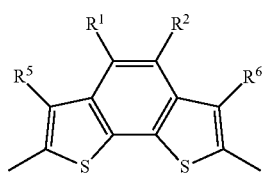

And said acceptor can consist—among others—of the following compounds:

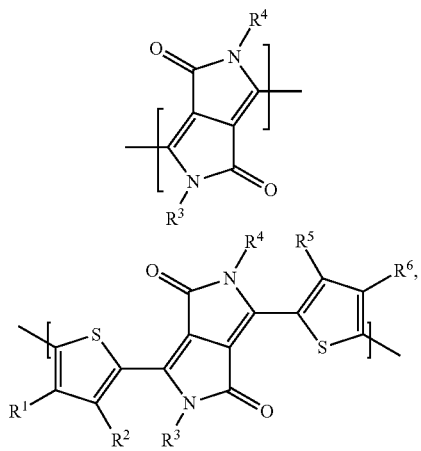

wherein $R^1$, $R^3$, $R^4$, $R^5$ and $R^6$ are independently selected from H, $C_1$-$C_{20}$alkyl, $C_1$-$C_{20}$fluoroalkyl, $C_1$-$C_{20}$alkoxy, $C_1$-$C_{20}$fluoroalkoxy, halo and aryl. The following compound is explicitly mentioned:

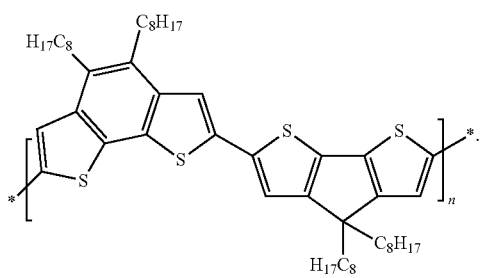

WO2011002927 describes compositions comprising conjugated polymers containing a bithiophene unit. In particular, WO2011002927 includes a claim for polymers comprising at least one repeating unit of the formula (I):

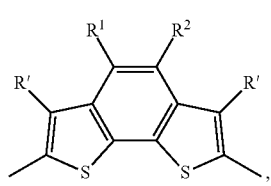

wherein $R^1$ and $R^2$ and $R'$ are solubilizing groups or hydrogen.

WO2011011545 relates to conjugated polymers comprising carbonyl substituted thieno (3,4-b) thiophene units, used as photovoltaic material in photovoltaic devices e.g. photodetector devices; and as active layer material in electronic devices such as sensors. Explicitly claimed is the following compound (III):

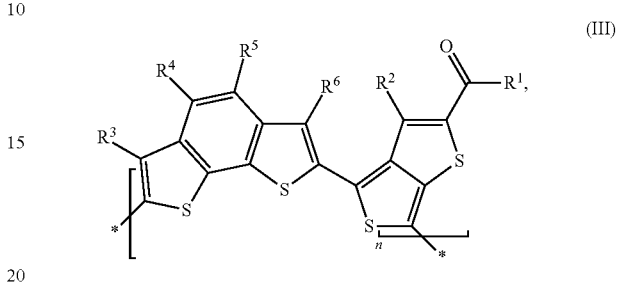

wherein $R^1$ is selected from hydrogen, alkyls, substituted alkyls, aryls, substituted aryls, $R^2$, $R^3$, $R^4$, $R^5$ and $R^6$ are selected independently from hydrogen, alkyls, substituted alkyls, alkoxyls, substituted alkoxyls, halogens, aryls, substituted aryls.

WO2011153694 relates to conjugated polymer of perylene tetracarboxylic acid diimide and benzodithiophene for manufacturing solar cell, organic electroluminescent devices and organic field effect transistors.

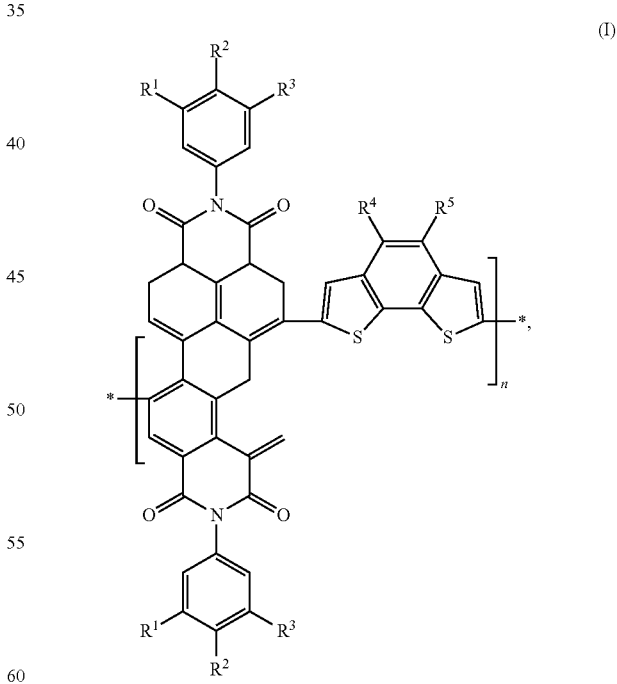

wherein $R^4$ and $R^5$ are alkyl groups.

WO2011147067, WO2011160302, CN102329413 and WO2012031404 respectively relate to polymers of general formula (I), (II), (III) and (IV), preparation methods and uses thereof.

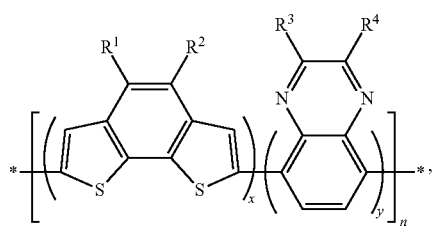 (I)

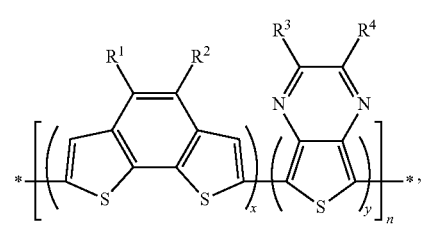 (II)

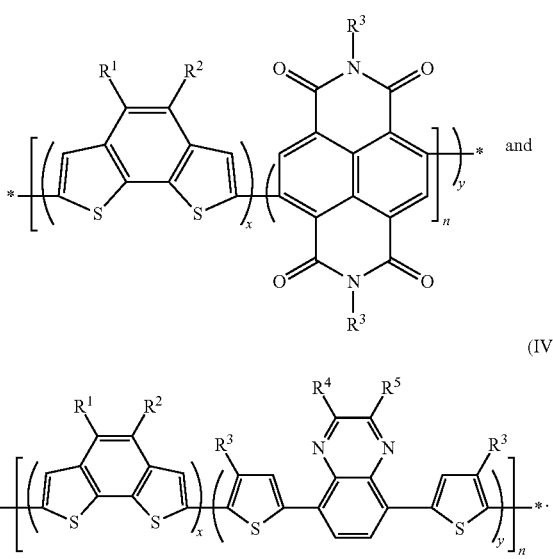 (III)

and (IV)

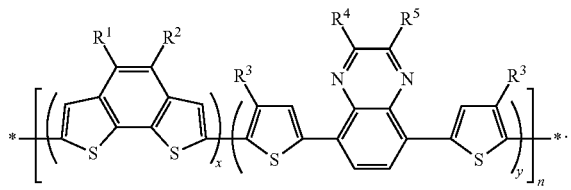

Compounds are disclosed, wherein R¹ and R² are alkyl.

T. Lei et al.; Chemistry of Materials 24 (2012) 1762-1770 relates to the preparation and study of isoindigo based polymers for organic field-effect transistor. In particular the following polymer is presented:

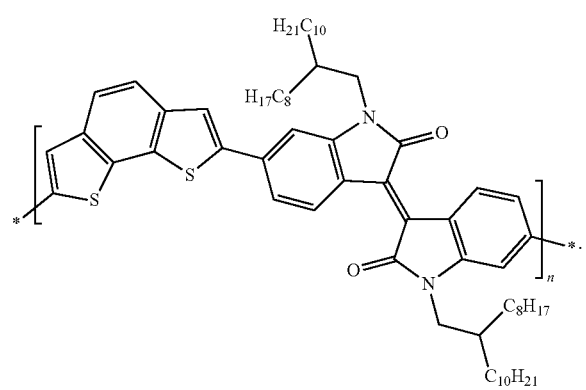

It is one object of the present invention to provide polymers, which show high efficiency of energy conversion, excellent field-effect mobility, good on/off current ratios and/or excellent stability, when used in organic field effect transistors, organic photovoltaics (solar cells) and photodiodes.

Said object has been solved by polymers, comprising a repeating unit of the formula

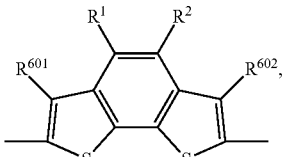 (I)

wherein $R^1$ is selected from hydrogen, $C_1$-$C_{100}$alkyl, or a group of formula —$SiR^{501}R^{502}R^{503}$;

$R^2$ is —CN, —$CF_3$, a fluorine atom, or a group of the formula

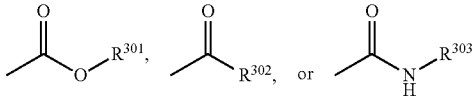

$R^{301}$, $R^{302}$ and $R^{303}$ are independently of each other $C_1$-$C_{18}$alkyl, $C_1$-$C_{18}$alkyl which is substituted by E' and/or interrupted by D', $C_1$-$C_{100}$fluoroalkyl, $C_3$-$C_{12}$cycloalkyl, $C_6$-$C_{24}$aryl, $C_6$-$C_{24}$aryl group, which is be substituted by G'; $C_2$-$C_{18}$alkenyl, $C_2$-$C_{18}$alkynyl, $C_7$-$C_{25}$aralkyl, or $C_7$-$C_{25}$aralkyl which is substituted by G'; $C_2$-$C_{20}$heteroaryl, or $C_2$-$C_{20}$heteroaryl, which is substituted by G';

$R^{601}$ and $R^{602}$ are independently of each other H, or $C_1$-$C_{25}$alkyl;

$R^{501}$, $R^{502}$ and $R^{503}$ are independently of each other $C_1$-$C_8$alkyl, especially $C_1$-$C_4$alkyl, $C_6$-$C_{24}$aryl, or $C_7$-$C_{12}$aralkyl;

D' is —CO—, —COO—, —S—, —SO—, —$SO_2$—, —O—, —$NR^{65}$—, —$SiR^{70}R^{71}$—, —$POR^{72}$—, —$CR^{63}$=$CR^{64}$—, or —C≡C—, and E' is —$OR^{69}$, —$SR^{69}$, —$NR^{65}R^{66}$, —$COR^{68}$, —$COOR^{67}$, —$CONR^{65}R^{66}$, —CN, $CF_3$, or halogen, G' is E', $C_1$-$C_{18}$alkyl, or $C_1$-$C_{18}$alkyl which is interrupted by —O—, $R^{63}$ and $R^{64}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^{65}$ and $R^{66}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—; or $R^{65}$ and $R^{66}$ together form a five or six membered ring, $R^{67}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{68}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{69}$ is $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{70}$ and $R^{71}$ are independently of each other $C_1$-$C_{18}$alkyl, $C_6$-$C_{18}$aryl, or $C_6$-$C_{18}$aryl, which is substituted by $C_1$-$C_{18}$alkyl, and $R^{72}$ is $C_1$-$C_{18}$alkyl, $C_6$-$C_{18}$aryl, or $C_6$-$C_{18}$aryl, which is substituted by $C_1$-$C_{18}$alkyl.

Advantageously, the polymer of the present invention, or an organic semiconductor material, layer or component, comprising the polymer of the present invention, can be used in organic light emitting diodes (PLEDs, OLEDs), organic photovoltaics (solar cells) and photodiodes, or in an organic field effect transistor (OFET).

The polymers of this invention preferably have a weight average molecular weight of 4,000 Daltons or greater, especially 4,000 to 2,000,000 Daltons, more preferably 10,000 to 1,000,000 and most preferably 10,000 to 100,000 Daltons. Molecular weights are determined according to high-temperature gel permeation chromatography (HT-GPC) using polystyrene standards. The polymers of this invention preferably have a polydispersity of 1.01 to 10, more preferably 1.1 to 3.0, most preferred 1.5 to 2.5. The polymers of the present invention are preferably conjugated.

In a preferred embodiment the present invention is directed to polymers comprising a repeating unit of the formula

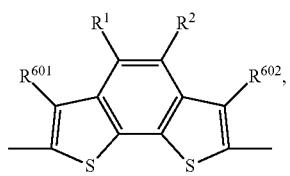

(I)

wherein $R^1$ is a selected from hydrogen, $C_1$-$C_{100}$alkyl, or a group of formula —SiR$^{501}$R$^{502}$R$^{503}$, especially —Si(R$^{501}$)$_3$. Preferably, $R^1$ is hydrogen, or $C_1$-$C_{100}$alkyl. If $R^1$ is $C_1$-$C_{100}$alkyl, it is preferably a linear, or branched $C_1$-$C_{25}$alkyl group, such as, for example, methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, especially n-dodecyl, tridecyl, tetradecyl, pentadecyl, hexadecyl, 2-ethyl-hexyl, 2-butyl-hexyl, 2-butyloctyl, 2-hexyldecyl, 2-decyl-tetradecyl, heptadecyl, octadecyl, eicosyl, heneicosyl, docosyl, or tetracosyl. Preferably, $R^{501}$, $R^{502}$ and $R^{503}$ are the same and are $C_1$-$C_4$alkyl, especially methyl, ethyl, isopropyl, or butyl; or phenyl.

$R^2$ is preferably

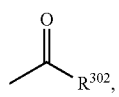

wherein $R^{302}$ is $C_1$-$C_{18}$alkyl; —CN, or a group of formula

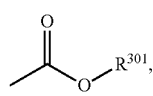

more preferred —CN, or a group of formula

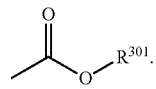

$R^{301}$ is preferably $C_1$-$C_{18}$alkyl, $C_1$-$C_{18}$alkyl which is substituted by E' and/or interrupted by O, thiophen, thiophen, which is substituted by one, or more G', especially by one or more groups selected from $C_1$-$C_{18}$alkyl, halogen, OR$^{69}$, CN, or CF$_3$; phenyl, or phenyl, which is substituted by one, or more G', especially by one or more groups selected from $C_1$-$C_{18}$alkyl, halogen, OR$^{69}$, CN, or CF$_3$; wherein R$^{69}$ is $C_1$-$C_{18}$alkyl, or phenyl. $R^{301}$ is more preferably $C_1$-$C_{18}$alkyl, phenyl, or phenyl, which is substituted by one, or more $C_1$-$C_{18}$alkyl groups.

Most preferred, $R^2$ is a group of formula

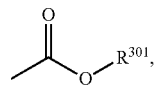

wherein $R^{301}$ is $C_1$-$C_{18}$alkyl, phenyl, or phenyl, which is substituted by one, or more $C_1$-$C_{18}$alkyl groups.

$R^{601}$ and $R^{602}$ are independently of each other H, or $C_1$-$C_{25}$alkyl. Most preferred, $R^{601}$ and $R^{602}$ are hydrogen.

In a preferred embodiment the present invention is directed to polymers comprising a repeating unit of the formula

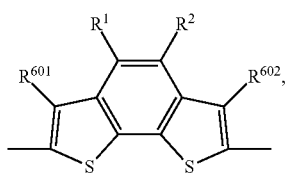

(I)

wherein $R^1$ is a selected from hydrogen, $C_1$-$C_{100}$alkyl, or a group of formula —SiR$^{501}$R$^{502}$R$^{503}$, $R^2$ is —CN, or a group of formula

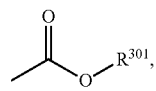

$R^{301}$ is $C_1$-$C_{18}$alkyl, phenyl, phenyl, which is substituted by one, or more groups selected from $C_1$-$C_{18}$alkyl, halogen, OR$^{69}$, CN, or CF$_3$; wherein R$^{69}$ is $C_1$-$C_{18}$alkyl, or phenyl; and $R^{601}$ and $R^{602}$ are independently of each other H, or $C_1$-$C_{25}$alkyl, especially $R^{601}$ and $R^{602}$ are hydrogen.

Among the repeating units of formula I repeating units of the formula (Ia)

[Structure: benzodithiophene with R¹, R⁶⁰¹, R⁶⁰² substituents and C(O)OR³⁰¹ group] and (Ib)

[Structure: benzodithiophene with R¹, R⁶⁰¹, R⁶⁰² substituents and CN group]

are preferred, wherein
  $R^1$ is hydrogen, or $C_1$-$C_{100}$alkyl, especially $C_1$-$C_{25}$alkyl; $C_1$-$C_{18}$alkyl, $C_1$-$C_{18}$alkyl which is interrupted by O; thiophen, thiophen, which is substituted by one, or more groups selected from $C_1$-$C_{18}$alkyl, halogen, $OR^{69}$, CN, or $CF_3$; phenyl, or phenyl, which is substituted by one, or more groups selected from $C_1$-$C_{18}$alkyl, halogen, $OR^{69}$, CN, or $CF_3$; wherein $R^{69}$ is $C_1$-$C_{18}$alkyl, or phenyl;
  $R^{301}$ is $C_1$-$C_{18}$alkyl, phenyl, phenyl, which is substituted by one, or more groups selected from $C_1$-$C_{18}$alkyl, halogen, $OR^{69}$, CN, or $CF_3$; wherein $R^{69}$ is $C_1$-$C_{18}$alkyl, or phenyl; and
  $R^{601}$ and $R^{602}$ are the same and are hydrogen or $C_1$-$C_{18}$alkyl;
Among the repeating units of formula I repeating units of the formula (Ia)

[Structure]

wherein
  $R^1$ is hydrogen, or $C_1$-$C_{100}$alkyl, especially $C_1$-$C_{25}$alkyl;
  $R^{301}$ is $C_1$-$C_{18}$alkyl, phenyl, phenyl, which is substituted by one, or more groups selected from $C_1$-$C_{18}$alkyl, halogen, $OR^{69}$, CN, or $CF_3$; wherein $R^{69}$ is $C_1$-$C_{18}$alkyl, or phenyl;
  $R^{601}$ and $R^{602}$ are the same and are hydrogen or $C_1$-$C_{18}$alkyl; and repeating units of the formula (Ib)

[Structure]

are more preferred, wherein
  $R^1$ is hydrogen, or $C_1$-$C_{100}$alkyl, especially $C_1$-$C_{25}$alkyl; and
  $R^{601}$ and $R^{602}$ are the same and are hydrogen, or $C_1$-$C_{18}$alkyl.
  $R^{601}$ and $R^{602}$ are preferably hydrogen.
Among the repeating units of formula I repeating units of formula (Ia')

[Structure]

are most preferred, wherein $R^1$ is hydrogen or $C_1$-$C_{100}$alkyl, especially $C_1$-$C_{25}$alkyl; and $R^{301}$ is $C_1$-$C_{18}$alkyl, phenyl, or phenyl group, which is substituted by one, or more groups selected from $C_1$-$C_{18}$alkyl, halogen, $OR^{69}$, CN, or $CF_3$; wherein $R^{69}$ is $C_1$-$C_{18}$alkyl, or phenyl; especially by one, or more $C_1$-$C_{18}$alkyl groups.

The polymer may be a homopolymer of formula $$*\text{-}[A]_n\text{-}*,$$

wherein A is a repeating unit of formula (I), especially formula (Ia), or (Ib) as described above, and n is usually in the range of 4 to 1000, especially 4 to 200, very especially 5 to 150.

Alternatively, the polymer may be a polymer, comprising repeating units of the formula $$*\text{-}[A]\text{-}* \quad \text{and} \quad *\text{-}[COM^1]\text{-}*,$$

especially $$*\text{-}[A]\text{-}[COM^1]\text{-}*,$$

very especially a copolymer of formula $$*\text{-}[[A]\text{-}[COM^1]]_n\text{-}*,$$ (III)

wherein
  n is usually in the range of 4 to 1000, especially 4 to 200, very especially 5 to 150.
  A is a repeating unit of formula (I), and
  —$COM^1$- is a repeating unit $$*\text{-}[Ar^4]_k[Ar^5]_l[Ar^6]_r[Ar^7]_z\text{-}*,$$

wherein
  k is 0, 1, 2, or 3; l is 1, 2, or 3; r is 0, 1, 2, or 3; z is 0, 1, 2, or 3;

Ar⁴, Ar⁵, Ar⁶ and Ar⁷ are independently of each other a group of formula and
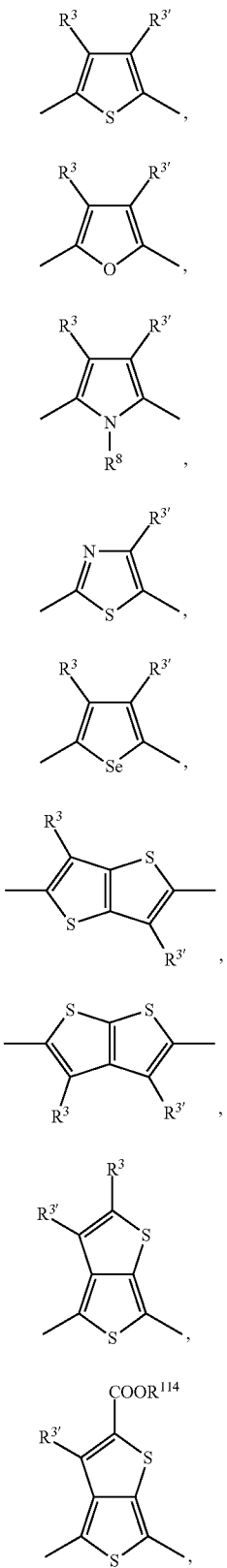
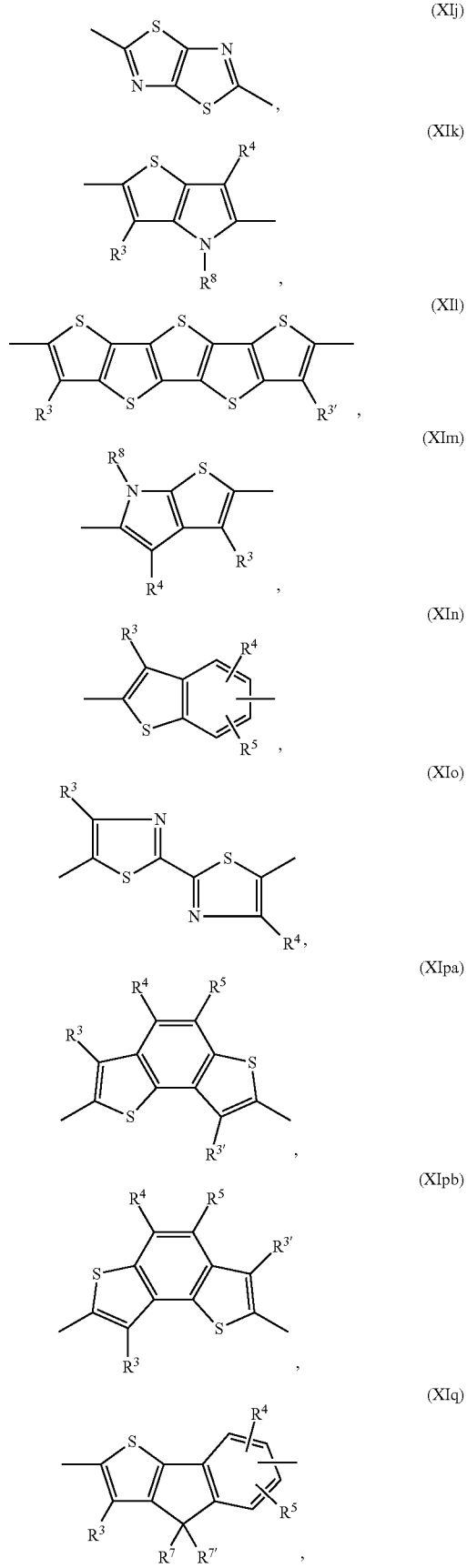

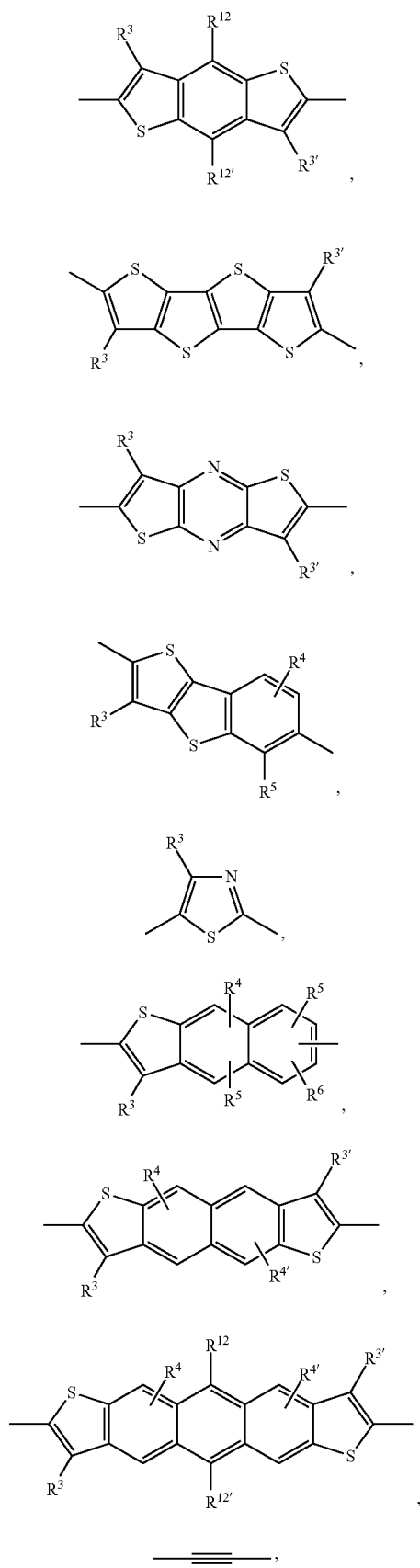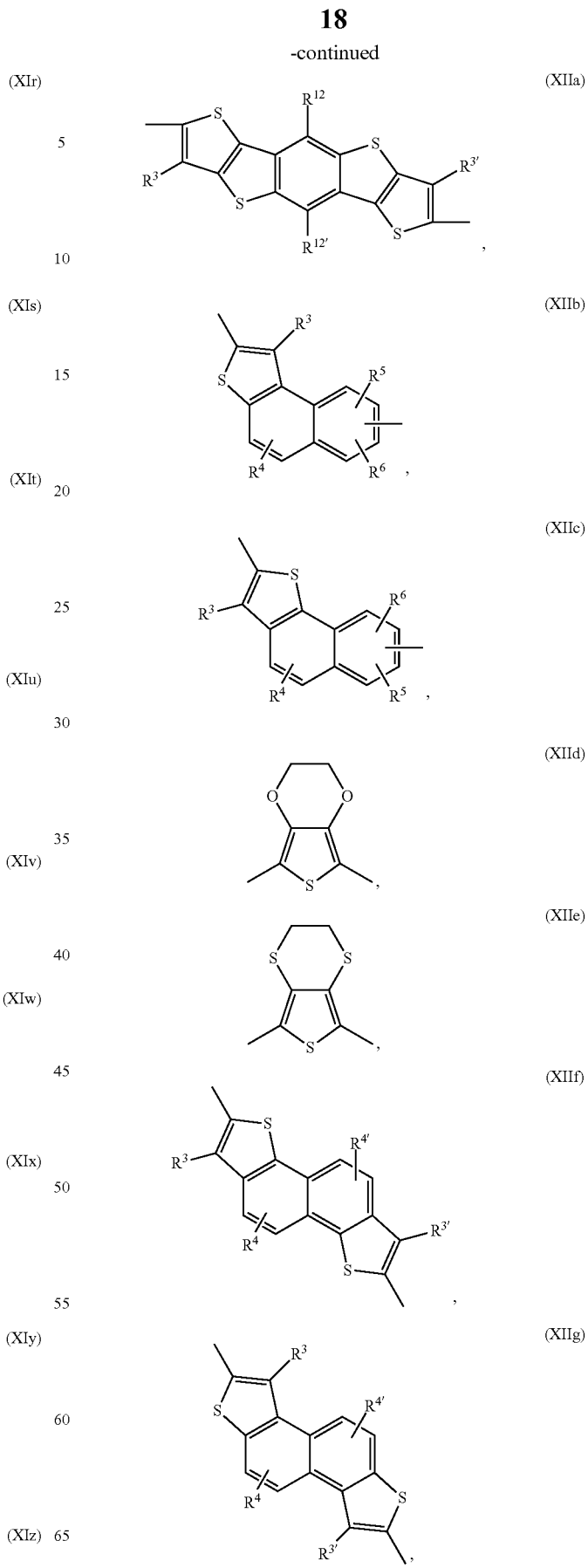

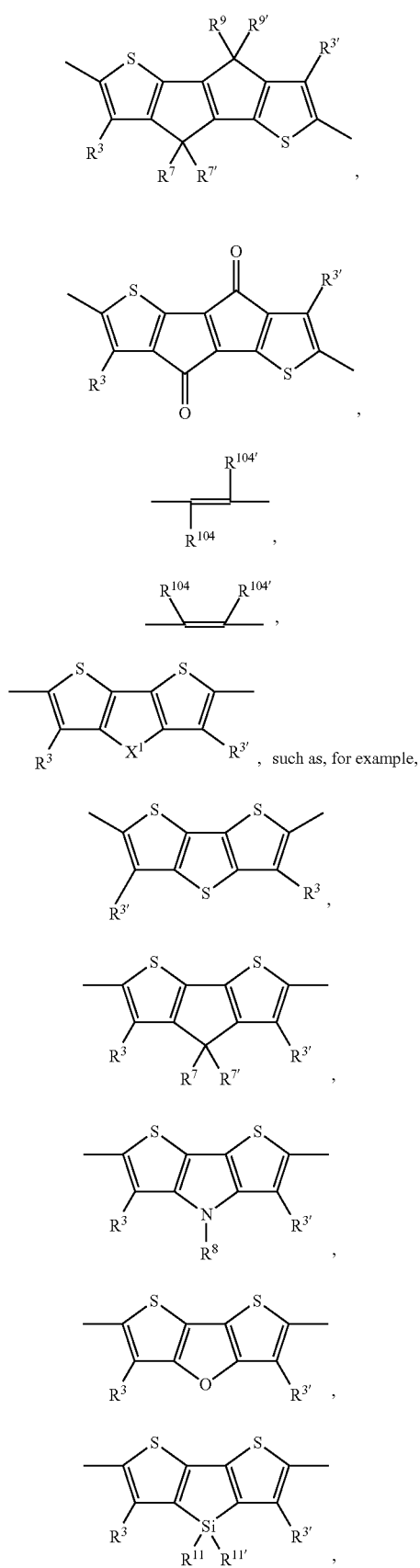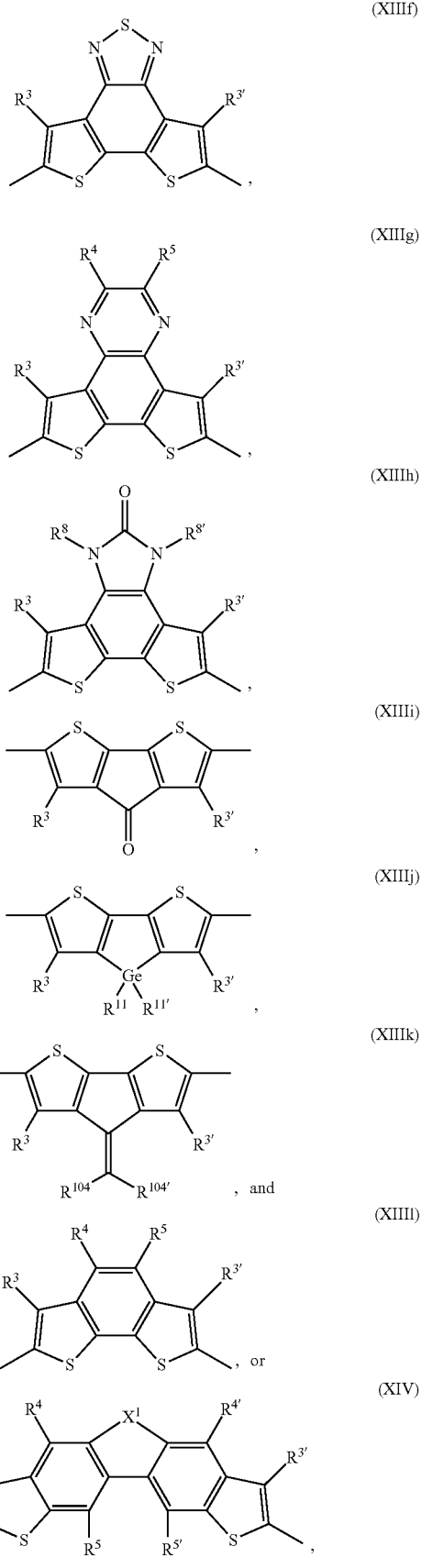

such as, for example,
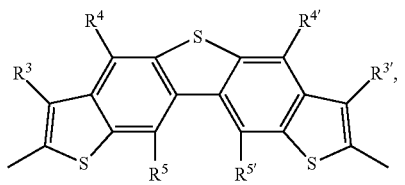
(XIVa)
wherein
X¹ is —O—, —S—, —NR⁸—, —Si(R¹¹)(R¹¹')—, —Ge(R¹¹)(R¹¹')—, —C(R⁷)(R⁷')—, —C(=O)—, —C(=CR¹⁰⁴R¹⁰⁴')—,
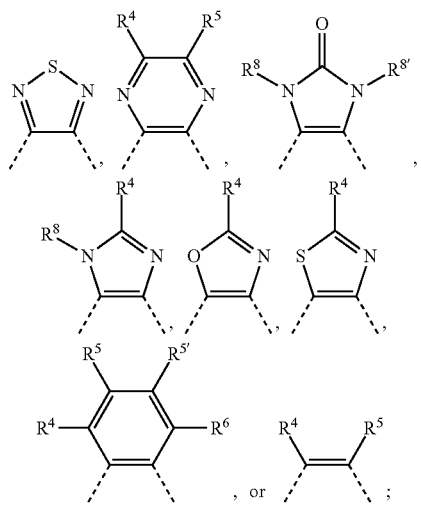
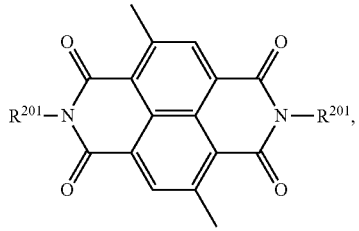
(XVa)
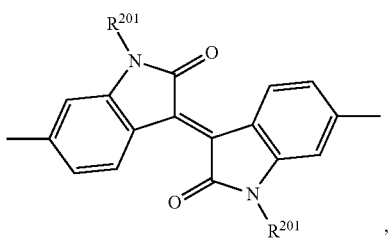
(XVb)
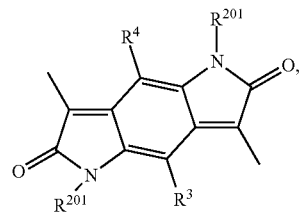
(XVc)
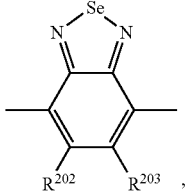
(XVd)
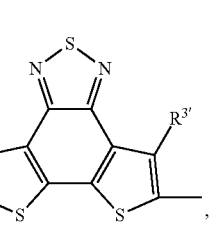
(XVe)
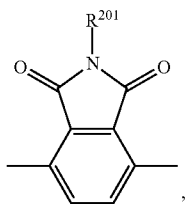
(XVf)
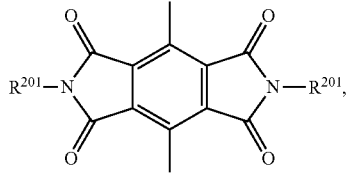
(XVg)
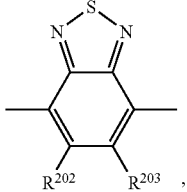
(XVh)
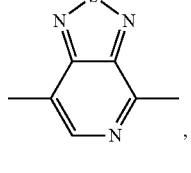
(XVi)
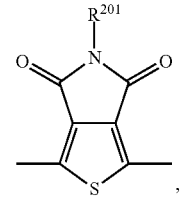
(XVj)
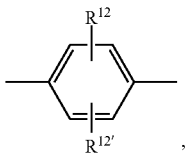
(XVk)

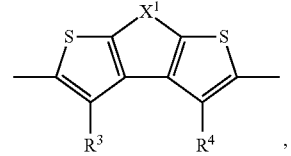 (XVl)
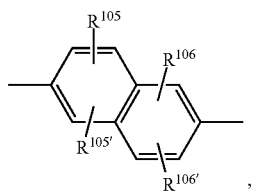 (XVm)
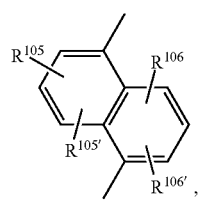 (XVn)
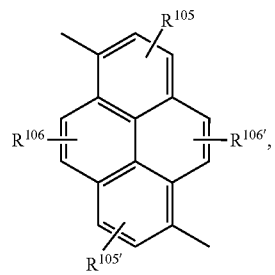 (XVo)
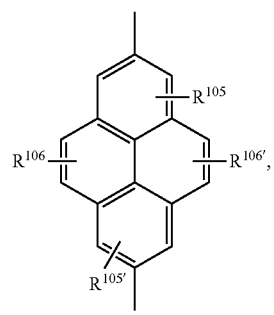 (XVp)
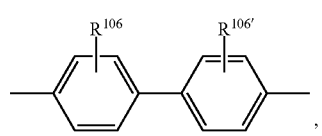 (XVq)
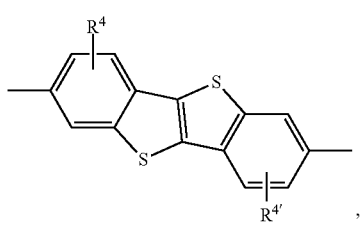 (XVr)
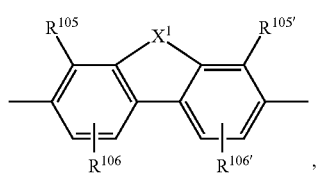 (XVs)
such as, for example,
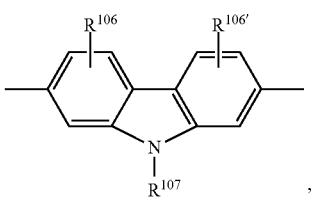 (XVsa)
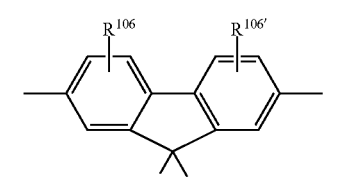 (XVsb)
, and
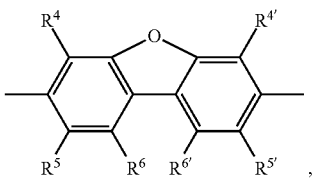 (XVsc)
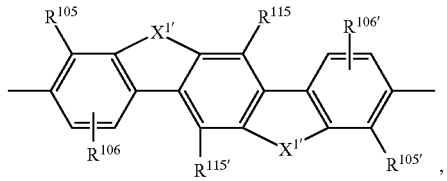 (XVt)
such as, for example,
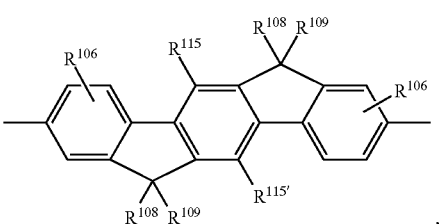 (XVta)
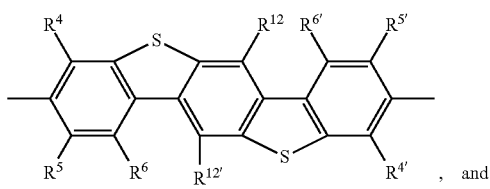 (XVtb)
, and

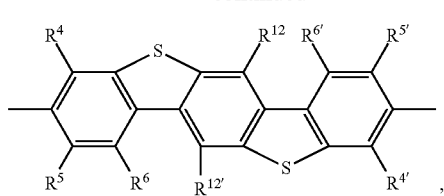

wherein

X¹' is S, O, —NR¹⁰⁷—, —Si(R¹¹⁷)(R¹¹⁷')—, —Ge(R¹¹⁷)(R¹¹⁷')—, —C(R¹⁰⁸)(R¹⁰⁹)—, —C(=O)—, —C(=CR¹⁰⁴R¹⁰⁴')—,

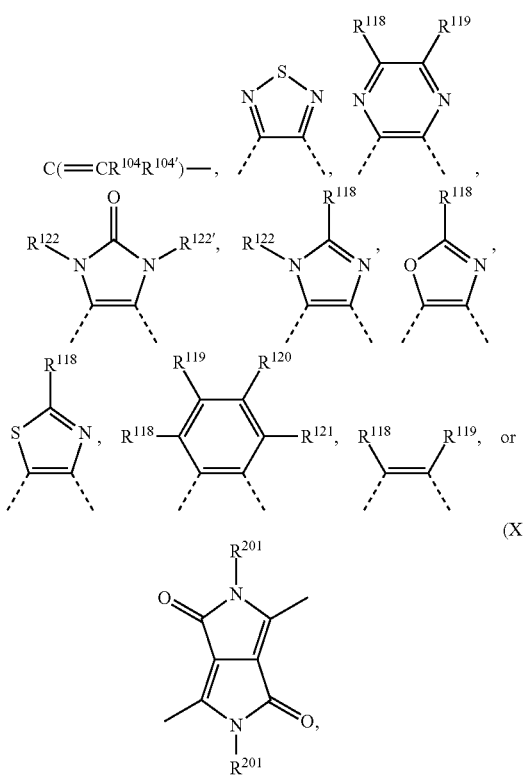

R³ and R³' are independently of each other hydrogen, halogen, halogenated $C_1$-$C_{25}$alkyl, cyano, $C_1$-$C_{25}$alkyl, which may optionally be interrupted by one or more oxygen or sulphur atoms; $C_7$-$C_{25}$arylalkyl, or $C_1$-$C_{25}$alkoxy;

R¹⁰⁴ and R¹⁰⁴' are independently of each other hydrogen, cyano, COOR¹⁰³, a $C_1$-$C_{25}$alkyl group, or $C_6$-$C_{24}$aryl or $C_2$-$C_{20}$heteroaryl, R⁴, R⁴', R⁵, R⁵', R⁶, and R⁶' are independently of each other hydrogen, halogen, halogenated $C_1$-$C_{25}$alkyl, cyano, $C_1$-$C_{25}$alkyl, which may optionally be interrupted by one or more oxygen or sulphur atoms; $C_7$-$C_{25}$arylalkyl, or $C_1$-$C_{25}$alkoxy;

R⁷, R⁷', R⁹ and R⁹' are independently of each other hydrogen, $C_1$-$C_{25}$alkyl, which may optionally be interrupted by one, or more oxygen, or sulphur atoms; or $C_7$-$C_{25}$arylalkyl, R⁸ and R⁸' are independently of each other hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms; or $C_7$-$C_{25}$arylalkyl, R¹¹ and R¹¹' are independently of each other $C_1$-$C_{25}$alkyl group, $C_7$-$C_{25}$arylalkyl, or a phenyl group, which can be substituted one to three times with $C_1$-$C_8$alkyl and/or $C_1$-$C_8$alkoxy;

R¹² and R¹²' are independently of each other hydrogen, halogen, cyano, $C_1$-$C_{25}$alkyl, which may optionally be interrupted by one, or more oxygen, or sulphur atoms, $C_1$-$C_{25}$alkoxy, $C_7$-$C_{25}$arylalkyl, or —≡-R¹³, wherein R¹³ is a $C_1$-$C_{10}$alkyl group, or a tri($C_1$-$C_8$alkyl)silyl group; or R¹⁰⁴ and R¹⁰⁴' are independently of each other hydrogen, $C_1$-$C_{18}$alkyl, $C_6$-$C_{10}$aryl, which may optionally be substituted by G, or $C_2$-$C_8$heteroaryl, which may optionally be substituted by G, R¹⁰⁵, R¹⁰⁵', R¹⁰⁶ and R¹⁰⁶' are independently of each other hydrogen, halogen, cyano, $C_1$-$C_{25}$alkyl, which may optionally be interrupted by one or more oxygen or sulphur atoms; $C_7$-$C_{25}$arylalkyl, or $C_1$-$C_{18}$alkoxy, R¹⁰⁷ is hydrogen, $C_7$-$C_{25}$arylalkyl, $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$perfluoroalkyl; $C_1$-$C_{25}$alkyl; which may be interrupted by —O—, or —S—; or —COOR¹⁰³;

R¹⁰⁸ and R¹⁰⁹ are independently of each other H, $C_1$-$C_{25}$alkyl, $C_1$-$C_{25}$alkyl which is substituted by E and/or interrupted by D, $C_7$-$C_{25}$arylalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or R¹⁰⁸ and R¹⁰⁹ together form a group of formula =CR¹¹⁰R¹¹¹ wherein R¹¹⁰ and R¹¹¹ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or R¹⁰⁸ and R¹⁰⁹ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, D is —CO—, —COO—, —S—, —O—, or —NR¹¹²'—, E is $C_1$-$C_8$thioalkoxy, $C_1$-$C_8$alkoxy, CN, —NR¹¹²'R¹¹³', —CONR¹¹²'R¹¹³', or halogen, G is E, or $C_1$-$C_{18}$alkyl, and R¹¹²' and R¹¹³' are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, R¹¹⁵ and R¹¹⁵' are independently of each other hydrogen, halogen, cyano, $C_1$-$C_{25}$alkyl, which may optionally be interrupted by one, or more oxygen, or sulphur atoms, $C_1$-$C_{25}$alkoxy, $C_7$-$C_{25}$arylalkyl, or

——≡—R¹¹⁶, wherein R¹¹⁶ is a $C_1$-$C_{18}$alkyl group, or a tri($C_1$-$C_8$alkyl)silyl group;

R¹¹⁷ and R¹¹⁷' are independently of each other $C_1$-$C_{25}$alkyl group, $C_7$-$C_{25}$arylalkyl, or a phenyl group, which can be substituted one to three times with $C_1$-$C_8$alkyl and/or $C_1$-$C_8$alkoxy; R¹¹⁸, R¹¹⁹, R¹²⁰ and R¹²¹ are independently of each other hydrogen, halogen, halogenated $C_1$-$C_{25}$alkyl, cyano, $C_1$-$C_{25}$alkyl, which may optionally be interrupted by one or more oxygen or sulphur atoms; $C_7$-$C_{25}$arylalkyl, or $C_1$-$C_{25}$alkoxy;

$R^{122}$ and $R^{122'}$ are independently of each other hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms; or $C_7$-$C_{25}$arylalkyl.

$R^{201}$ is selected from hydrogen, a $C_1$-$C_{100}$alkyl group, —COOR$^{103}$, a $C_1$-$C_{100}$alkyl group substituted by one or more halogen atoms, hydroxyl groups, nitro groups, —CN, or $C_6$-$C_{18}$aryl groups and/or interrupted by —O—, —COO—, —OCO— or —S—; a $C_7$-$C_{25}$arylalkyl group, a carbamoyl group, a $C_5$-$C_{12}$cycloalkyl group, which can be substituted one to three times with $C_1$-$C_{100}$alkyl and/or $C_1$-$C_{100}$alkoxy, a $C_6$-$C_{24}$aryl group, in particular phenyl or 1- or 2 naphtyl which can be substituted one to three times with $C_1$-$C_{100}$alkyl, $C_1$-$C_{100}$thioalkoxy, and/or $C_1$-$C_{100}$alkoxy; and pentafluorophenyl;

$R^{103}$ and $R^{114}$ are independently of each other $C_1$-$C_{25}$alkyl, which may optionally be interrupted by one, or more oxygen, or sulphur atoms, $R^{202}$ and $R^{203}$ may be the same or different and are selected from H, F, —CN, $C_1$-$C_{100}$alkyl, which may optionally be interrupted by one or more oxygen, or sulphur atoms; and $C_1$-$C_{100}$alkoxy.

The above-mentioned repeating units COM$^1$ are known and can be prepared according to known procedures. With respect to DPP repeating units and their synthesis reference is, for example, made to US6451459B1, WO05/049695, WO2008/000664, EP2034537A2, EP2075274A1, WO2010/049321, WO2010/049323, WO2010/108873, WO2010/115767, WO2010/136353, WO2010/136352 and PCT/EP2011/057878.

$R^3$, $R^{3'}$, $R^4$ and $R^{4'}$ are preferably hydrogen, or $C_1$-$C_{25}$alkyl.

$R^{201}$ is preferably a linear, or branched $C_1$-$C_{36}$alkyl group, such as, for example, methyl, ethyl, n-propyl, iso-propyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, especially n-dodecyl, tridecyl, tetradecyl, pentadecyl, hexadecyl, 2-ethylhexyl, 2-butyl-hexyl, 2-butyloctyl, 2-hexyldecyl, 2-decyltetradecyl, heptadecyl, octadecyl, eicosyl, heneicosyl, docosyl, or tetracosyl.

Advantageously, the groups $R^{201}$ can be represented by formula

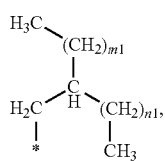

wherein m1=n1+2 and m1+n1≤24. Chiral side chains can either be homochiral, or racemic, which can influence the morphology of the compounds.

—COM$^1$- is preferably a repeating unit of formula

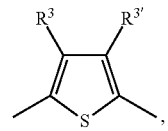

(XIa)

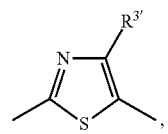

(XId)

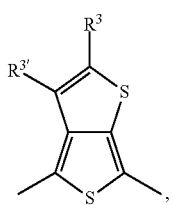

(XIh)

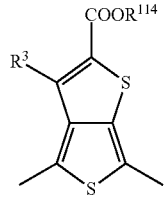

(XIi)

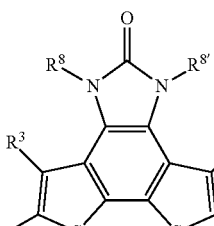

(XIIIh)

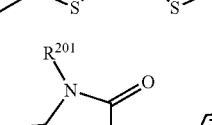

(XVb)

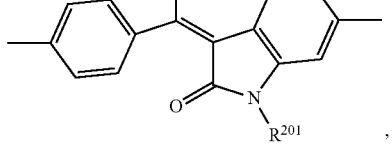

(XVb')

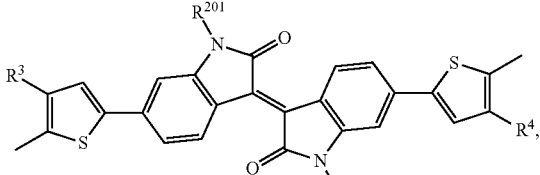

(XVe)

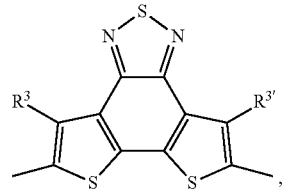

-continued

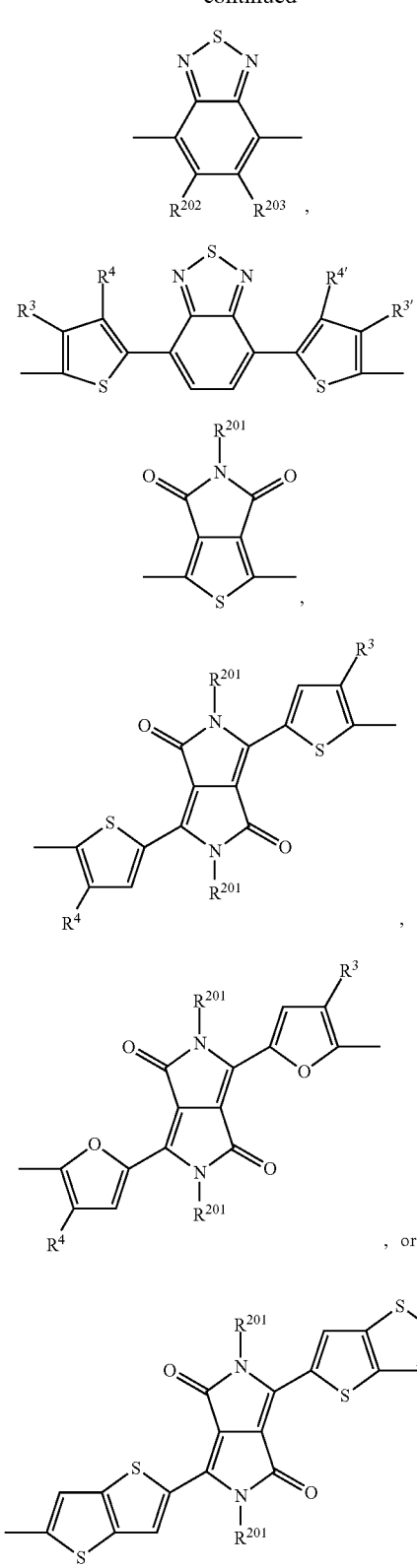

wherein $R^3$, $R^{3'}$, $R^4$ and $R^{4'}$ are independently of each other hydrogen, or $C_1$-$C_{25}$alkyl;

$R^8$ and $R^{8'}$ are independently of each other hydrogen, or $C_1$-$C_{25}$alkyl;

$R^{114}$ is a $C_1$-$C_{38}$alkyl group;

$R^{201}$ is a $C_1$-$C_{38}$alkyl group; and $R^{202}$ and $R^{203}$ are independently of each other hydrogen or $C_1$-$C_{25}$alkyl.

In a particularly preferred embodiment COM¹ is selected from repeating units of formula (XVb), (XVb'), (XVe), (XVh), (XVh'), (XVu'), (XVu"), and (XVu'''), especially (XVb), (XVb'), (XVu'), (XVu"), and (XVu''').

In a preferred embodiment of the present invention the polymer is a copolymer, comprising repeating units of formula

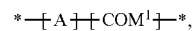

especially a copolymer of formula

     (III)

wherein A and COM¹ are as defined above; n is a number which results in a molecular weight of 4,000 to 2,000,000 Daltons, more preferably 10,000 to 1,000,000 and most preferably 10,000 to 100,000 Daltons. n is usually in the range of 4 to 1000, especially 4 to 200, very especially 5 to 150. The polymer structure represented by formula III is an idealized representation of the polymer products obtained, for example, via the Suzuki polymerization procedure. The repeating unit of formula

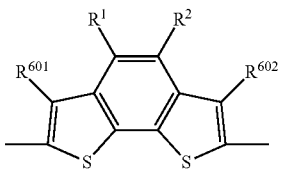     (I)

can be incorporated into the polymer chain in two ways:

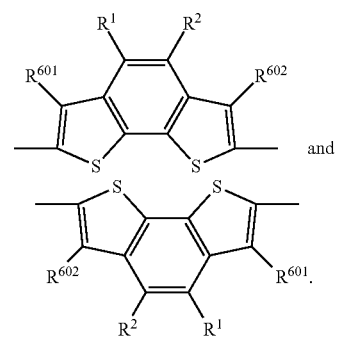

Both possibilities shall be covered by formula (III).

The polymers of the present invention can comprise more than 2 different repeating units, such as, for example, repeating units A, COM¹ and B, which are different from each other. In said embodiment the polymer is a copolymer, comprising repeating units of formula

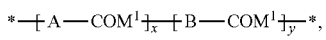

wherein x=0.995 to 0.005, y=0.005 to 0.995, especially x=0.2 to 0.8, y=0.8 to 0.2, and x+y=1. B has the meaning of A, with the proviso that B is different from A. and $COM^1$ are as defined above.

In another embodiment the polymer is a copolymer, comprising repeating units of formula

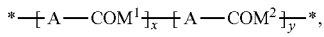

wherein x=0.995 to 0.005, y=0.005 to 0.995, especially x=0.2 to 0.8, y=0.8 to 0.2, and x+y=1. $COM^2$ has the meaning of $COM^1$, with the proviso that $COM^2$ is different from $COM^1$; A and $COM^1$ are as defined above.

In another preferred embodiment of the present invention A is a repeating unit of formula (I), especially (Ia), or (Ib) as defined above, and

is a group of formula

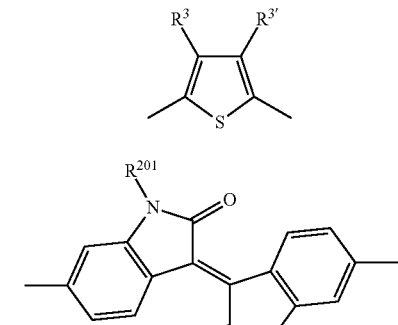 (XIa)

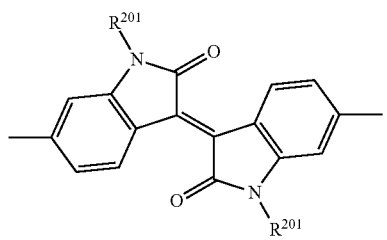 (XVb)

(XVb')

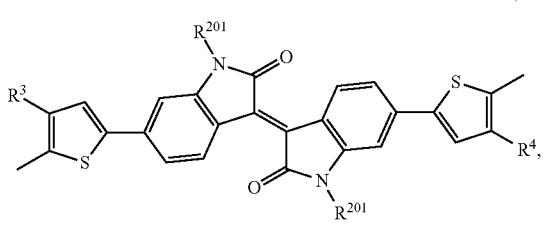

(XVe)

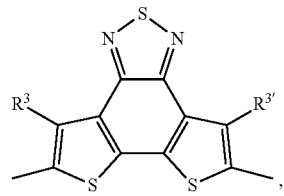

(XVh')

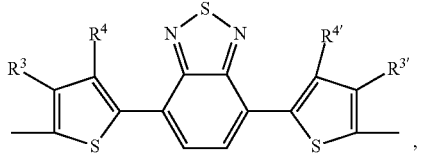

(XVu')

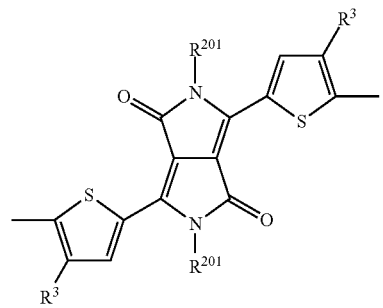

(XVu")

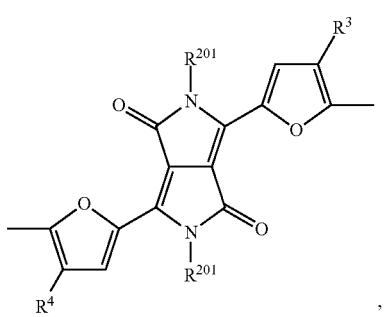

, or (XVu''')

[structure]

;

wherein $R^3$, $R^{3'}$, $R^4$ and $R^{4'}$ are independently of each other hydrogen, or $C_1$-$C_{25}$alkyl; $R^8$ and $R^{8'}$ are independently of each other hydrogen, or $C_1$-$C_{25}$alkyl; and $R^{201}$ is a $C_1$-$C_{38}$alkyl group.

$COM^1$ is preferably a repeating unit of formula (XVb), (XVb'), (XVu'), or (XVu").

Among the repeating units of formula (I) repeating units of formula (I) are preferred, wherein $R^1$ is hydrogen, $C_1$-$C_{100}$alkyl, or a group of formula —$SiR^{501}R^{502}R^{503}$, especially —$Si(R^{501})_3$. More preferably, $R^1$ is hydrogen, or $C_1$-$C_{100}$alkyl, especially $C_1$-$C_{25}$alkyl.

$R^2$ is preferably

[structure with $R^{302}$]

wherein $R^{302}$ is $C_1$-$C_{18}$alkyl; —CN, or a group of formula

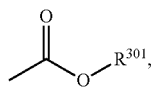

more preferred —CN, or a group of formula

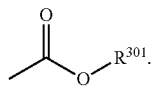

$R^{301}$ is preferably $C_1$-$C_{18}$alkyl, $C_1$-$C_{18}$alkyl which is substituted by E' and/or interrupted by O, thiophen, thiophen, which is substituted by one, or more G', especially by one or more groups selected from $C_1$-$C_{18}$alkyl, halogen, $OR^{69}$, CN, or $CF_3$; phenyl, or phenyl, which is substituted by one, or more G', especially by one or more groups selected from $C_1$-$C_{18}$alkyl, halogen, $OR^{69}$, CN, or $CF_3$; wherein $R^{69}$ is $C_1$-$C_{18}$alkyl, or phenyl. $R^{301}$ is more preferably $C_1$-$C_{18}$alkyl, phenyl, or phenyl, which is substituted by one, or more $C_1$-$C_{18}$alkyl groups.

Most preferred, $R^2$ is a group of formula

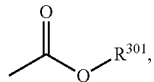

wherein $R^{301}$ is $C_1$-$C_{18}$alkyl, phenyl, or phenyl, which is substituted by one, or more $C_1$-$C_{18}$alkyl groups, especially $C_1$-$C_8$alkyl groups.

$R^{601}$ and $R^{602}$ are independently of each other H, or $C_1$-$C_{25}$alkyl; especially H.

Among the repeating units of formula I repeating units of formula

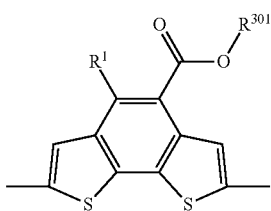

are most preferred, wherein $R^1$ is selected from hydrogen or $C_1$-$C_{100}$alkyl, especially $C_1$-$C_{25}$alkyl; and $R^{301}$ is $C_1$-$C_{18}$alkyl, phenyl, phenyl, which is substituted by one, or more groups selected from $C_1$-$C_{18}$alkyl, halogen, $OR^{69}$, CN, or $CF_3$; wherein $R^{69}$ is $C_1$-$C_{18}$alkyl, or phenyl; especially by one, or more $C_1$-$C_{18}$alkyl groups.

In a preferred embodiment the present invention is directed to polymers of formula $$*\!-\!\!\!+\!\!+\!\!A\!\!+\!\!+\!COM^1\!\!+\!\!\!+_n\!-\!\!*,$$ (III)

wherein n is 4 to 1000, especially 4 to 200, very especially 5 to 150;

A is a repeating unit of formula

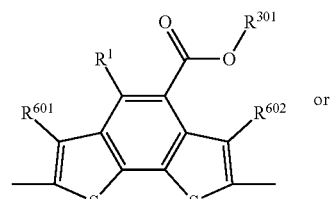

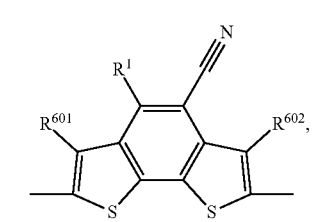

wherein $R^1$ is selected from hydrogen, or $C_1$-$C_{25}$alkyl, $R^{301}$ is $C_1$-$C_{18}$alkyl, phenyl, phenyl, which is substituted by one, or more groups selected from $C_1$-$C_{18}$alkyl, halogen, $OR^{69}$, CN, or $CF_3$; wherein $R^{69}$ is $C_1$-$C_{18}$alkyl, or phenyl; especially by one, or more $C_1$-$C_{18}$alkyl groups, $R^{601}$ and $R^{602}$ are hydrogen; and

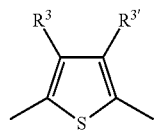

is a group of formula

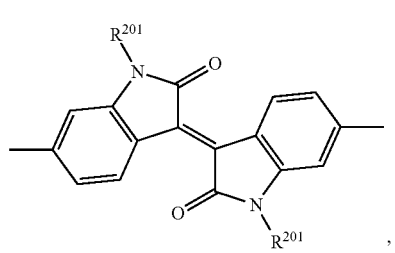

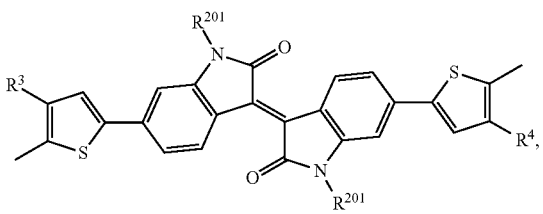

-continued
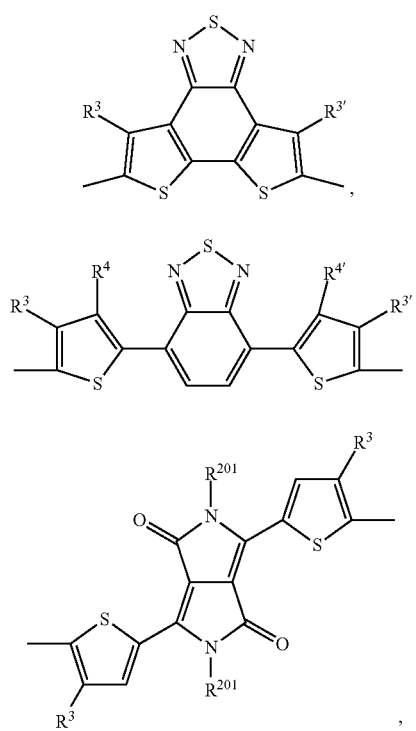
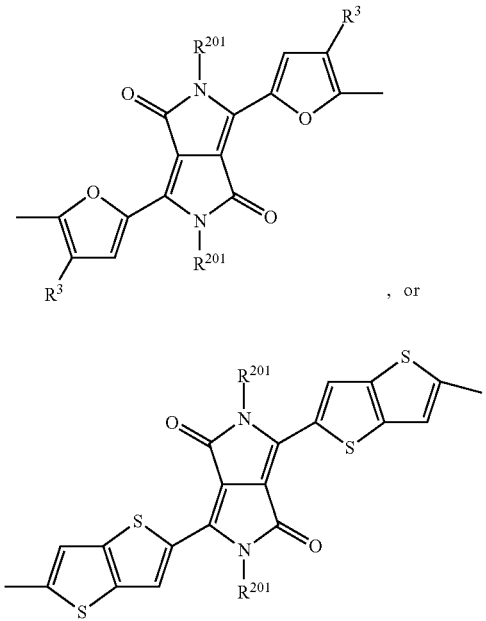
wherein R³, R³', R⁴ and R⁴' are independently of each other hydrogen, or $C_1$-$C_{25}$alkyl; and $R^{201}$ is a $C_1$-$C_{38}$alkyl group.
Among the polymers of formula III the following polymers are preferred:
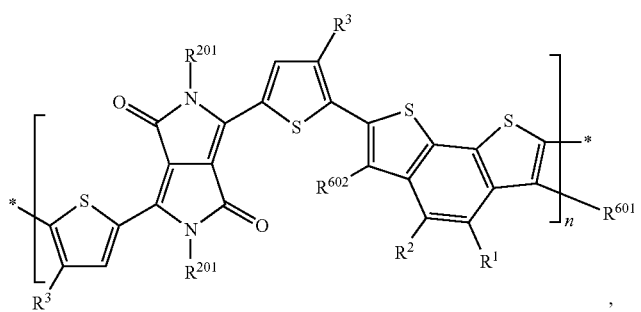
(III-1)
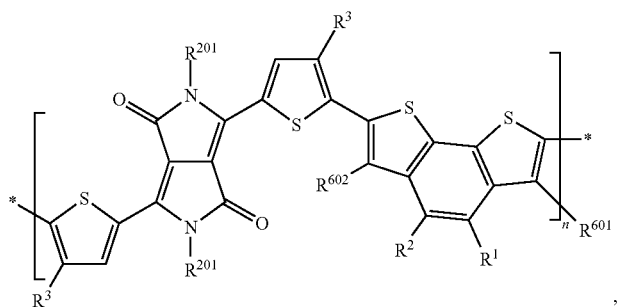
(III-2)

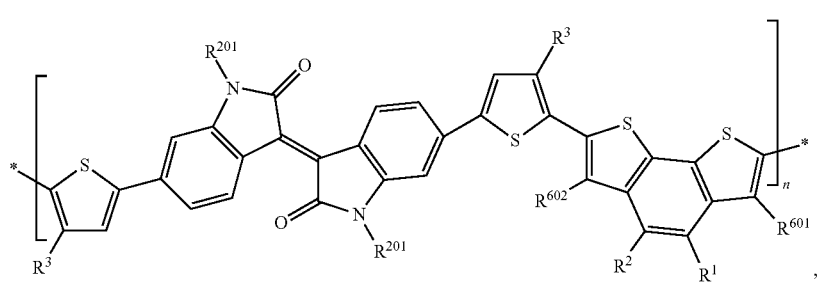

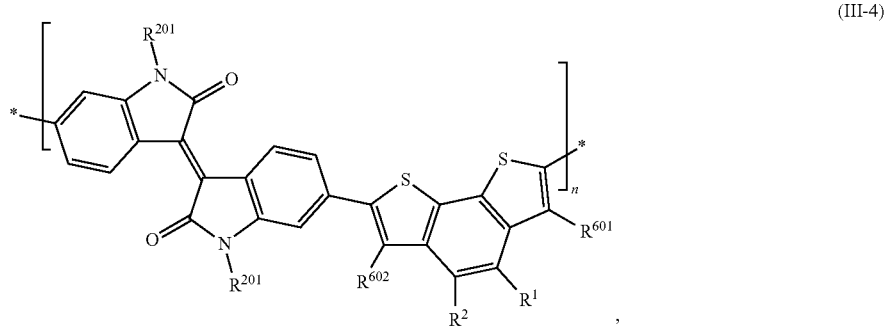

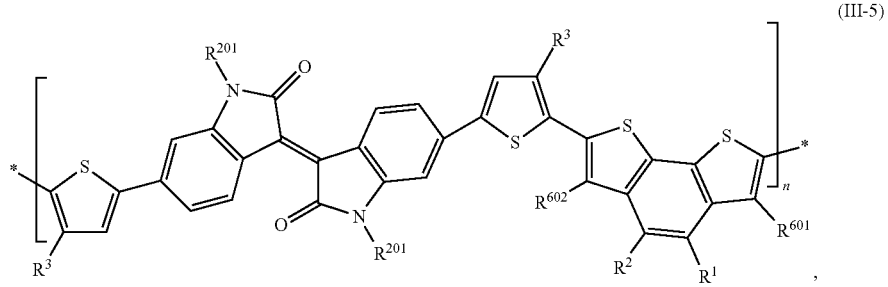

wherein n is 4 to 1000, especially 4 to 200, very especially 5 to 150;

$R^1$ is hydrogen, or $C_1$-$C_{100}$alkyl, especially hydrogen, or $C_1$-$C_{25}$alkyl;

$R^2$ is —CN, or a group of formula

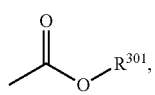

wherein $R^{301}$ is $C_1$-$C_{18}$ alkyl, phenyl, phenyl, which is substituted by one, or more groups selected from $C_1$-$C_{18}$alkyl, halogen, $OR^{69}$, CN, or $CF_3$; wherein $R^{69}$ is $C_1$-$C_{18}$alkyl, or phenyl; especially by one, or more $C_1$-$C_{18}$alkyl groups;

$R^{601}$ and $R^{602}$ are independently of each other H, or $C_1$-$C_{25}$alkyl; especially H;

$R^3$, $R^{3'}$, $R^4$ and $R^{4'}$ are independently of each other hydrogen, or $C_1$-$C_{25}$alkyl; and $R^{201}$ is a $C_1$-$C_{38}$alkyl group. Polymers of formula (III-1), (III-2), (III-3) and (III-4) are more preferred.

The following polymers are more preferred:

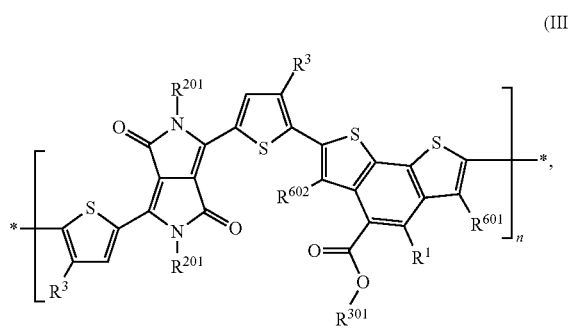

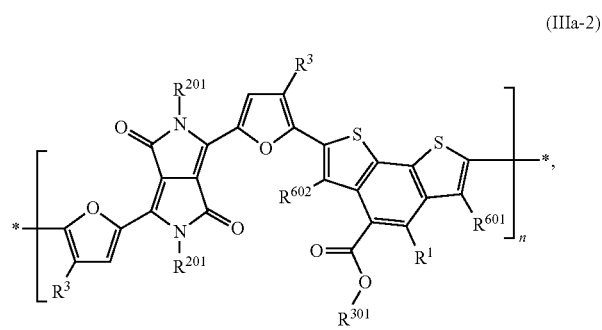

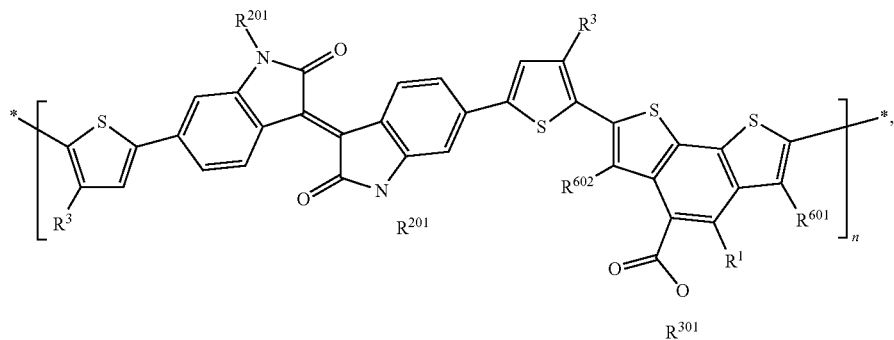
(IIIa-3)
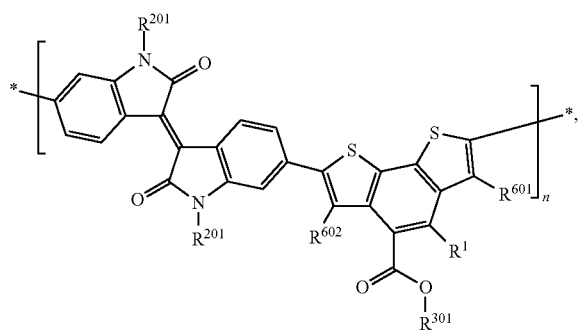
(IIIa-4)
(IIIb-1)
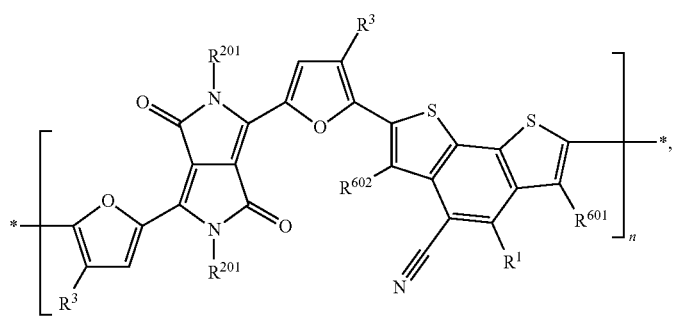
(IIIb-2)
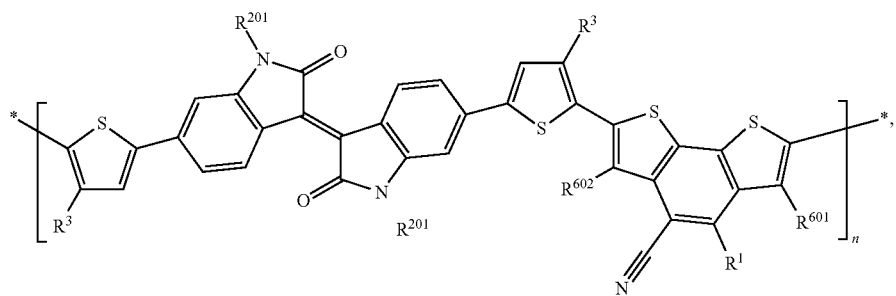
(IIIb-3)

-continued

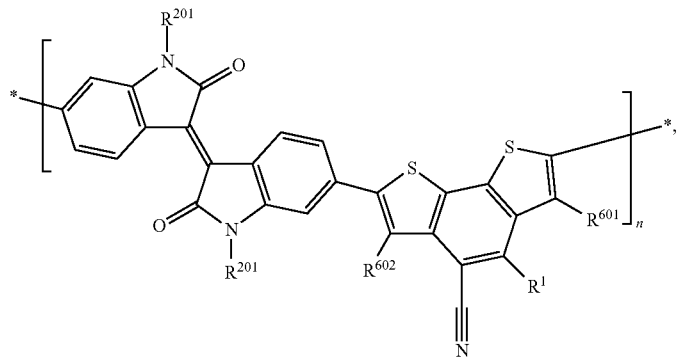

wherein n is 4 to 1000, especially 4 to 200, very especially 5 to 150;

$R^1$ is selected from hydrogen or $C_1$-$C_{100}$alkyl, $R^3$ and $R^{3'}$ are independently of each other hydrogen or $C_1$-$C_{25}$alkyl;

$R^{201}$ is a $C_1$-$C_{38}$alkyl group, $R^{301}$ is $C_1$-$C_{18}$alkyl, phenyl, phenyl, which is substituted by one, or more groups selected from $C_1$-$C_{18}$alkyl, halogen, $OR^{69}$, CN, or $CF_3$; wherein $R^{69}$ is $C_1$-$C_{18}$alkyl, or phenyl;

$R^{601}$ and $R^{602}$ are independently of each other hydrogen, or $C_1$-$C_{25}$alkyl; especially hydrogen. In case of $R^{301}$ halogen is preferably F, or Cl.

Examples of polymers of the present invention are shown below:

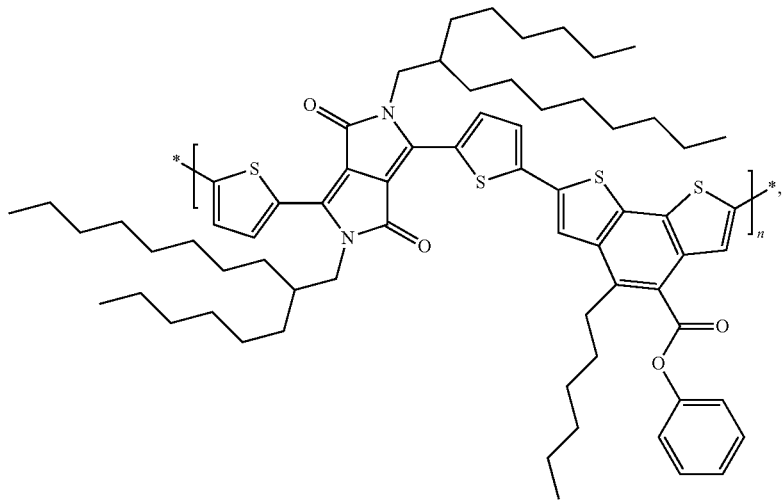

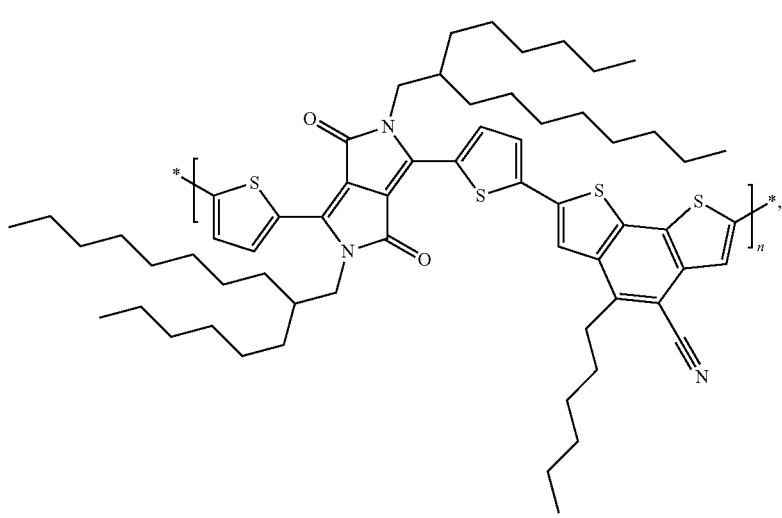

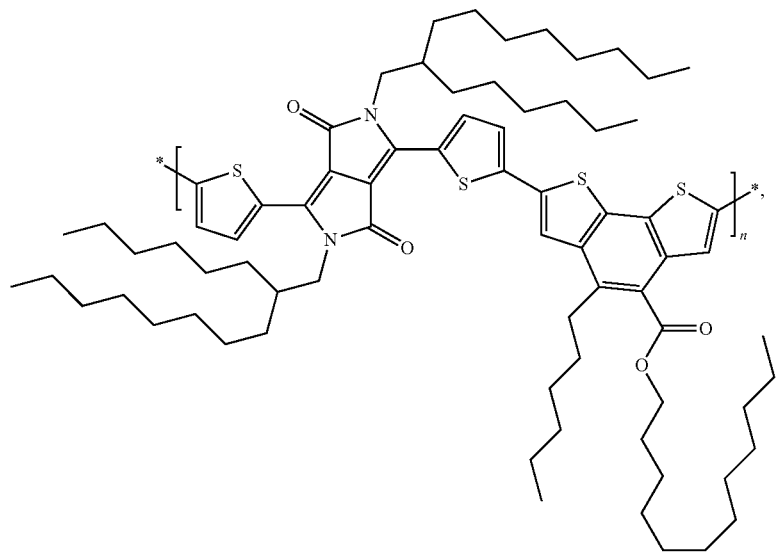
(P-102)
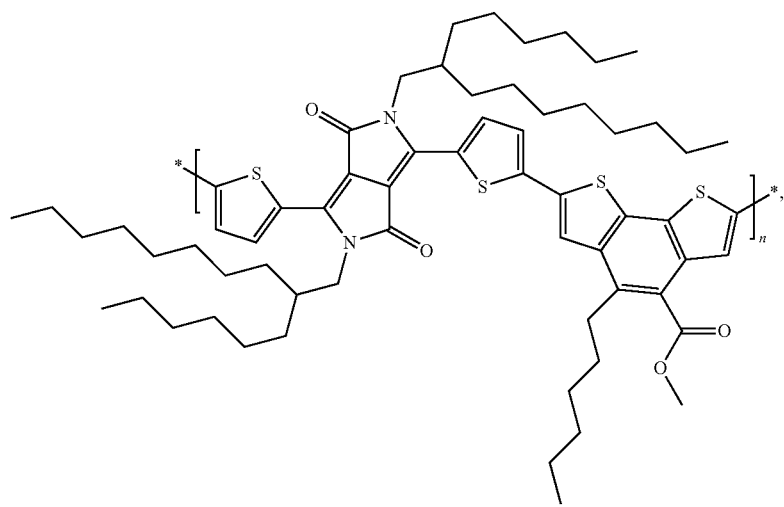
(P-103)
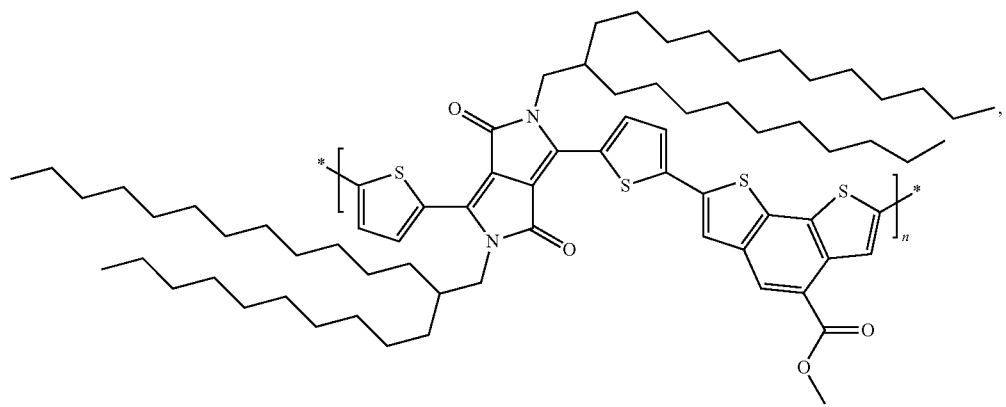
(P-104)

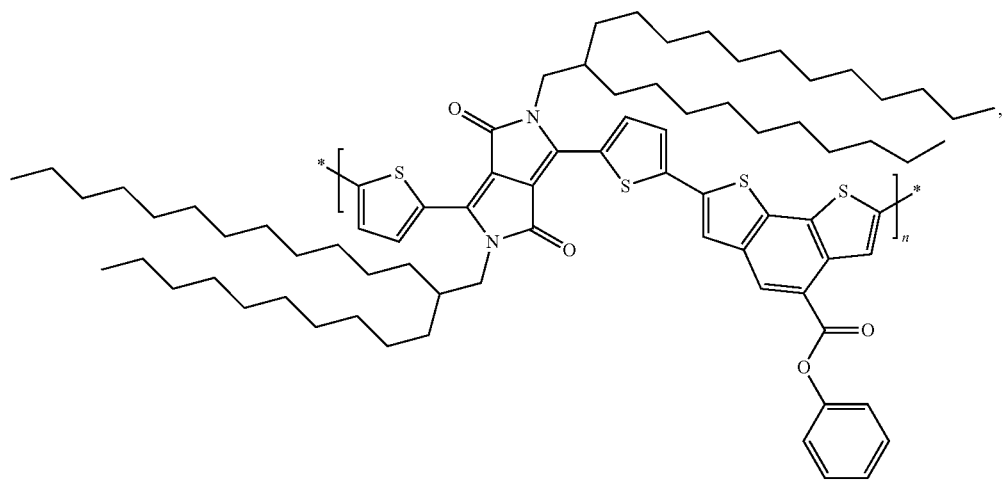
(P-105)
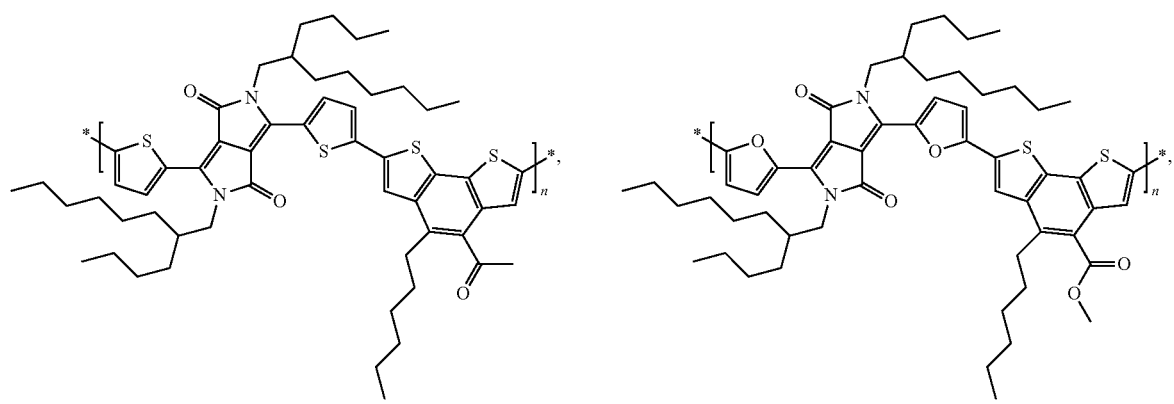
(P-106) (P-107)
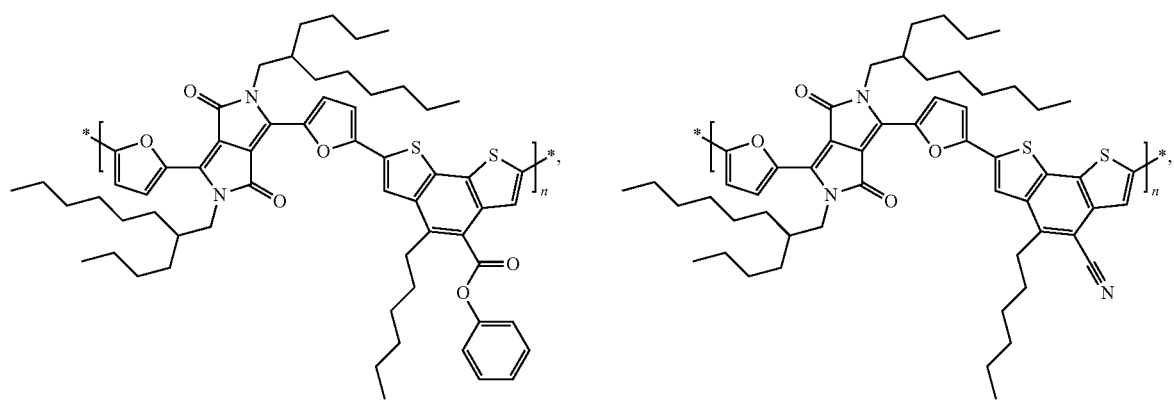
(P-108) (P-109)

-continued
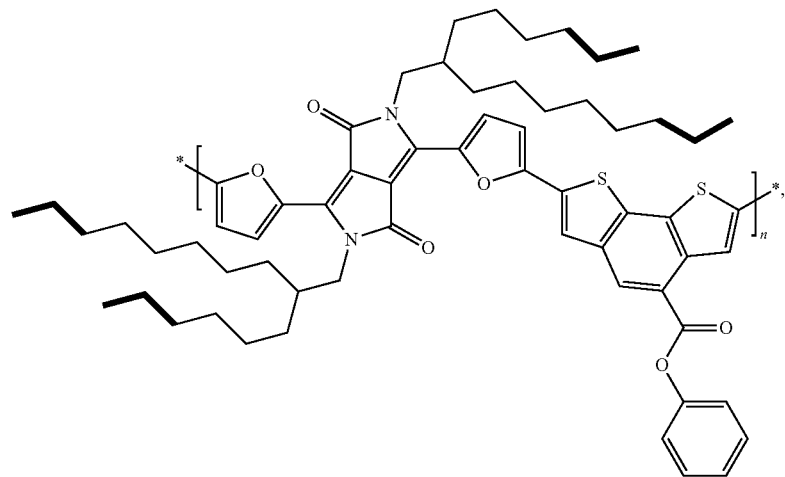
(P-110)
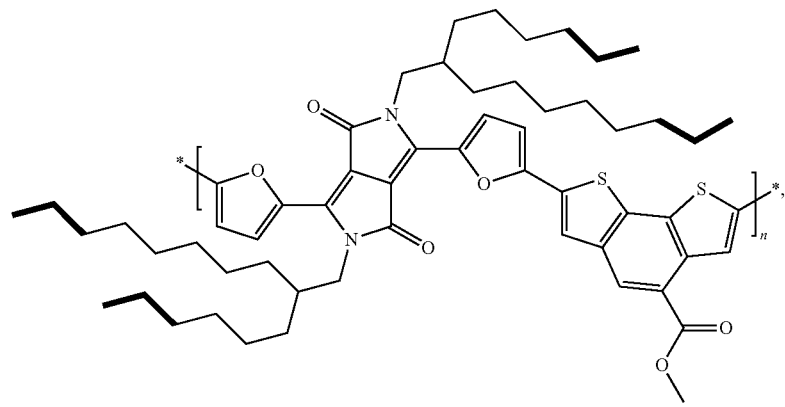
(P-111)
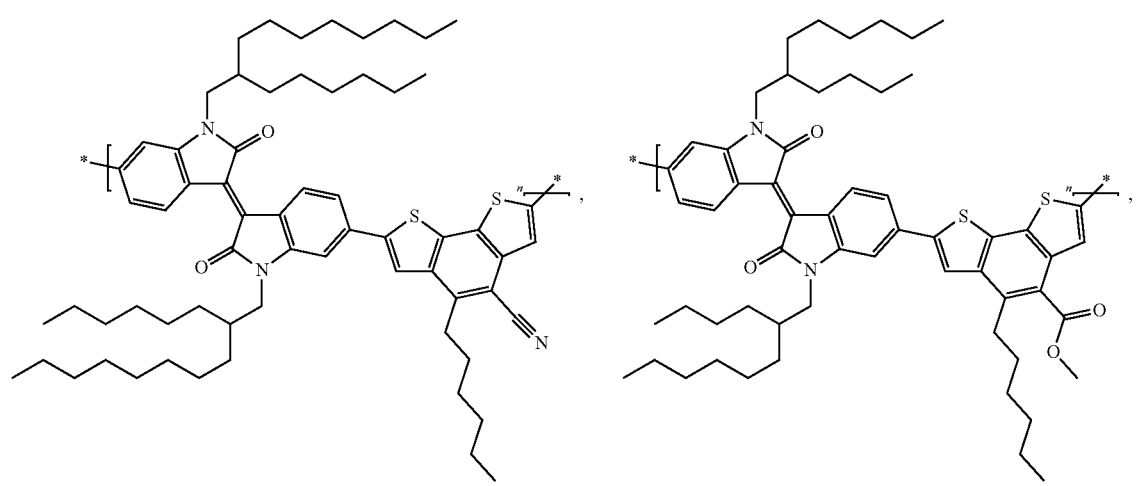
(P-112) (P-113)

-continued
(P-114)
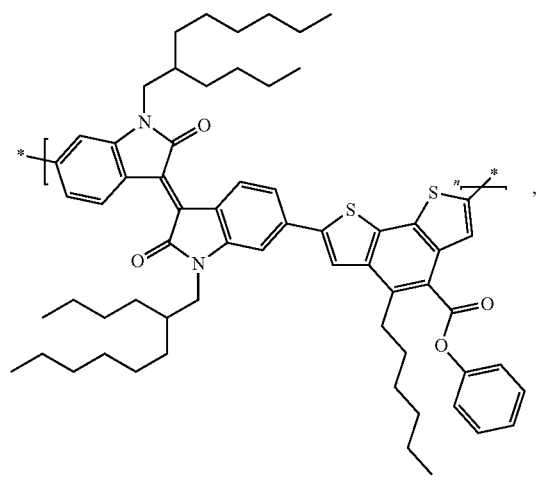
(P-115)
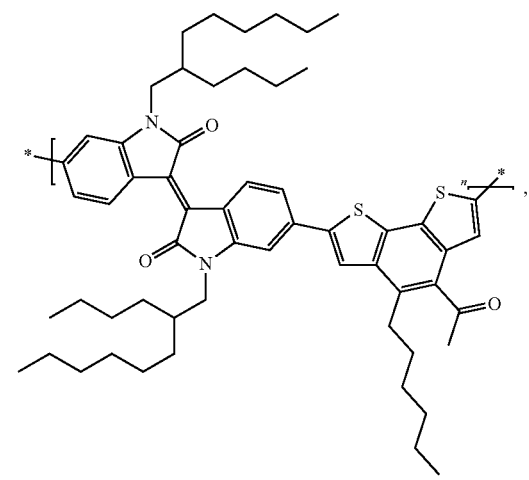
(P-116)
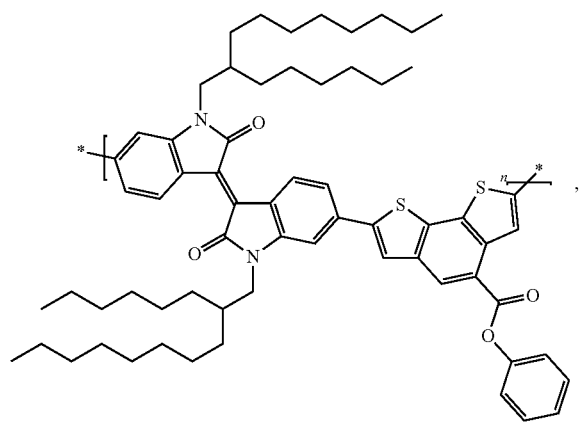
(P-117)
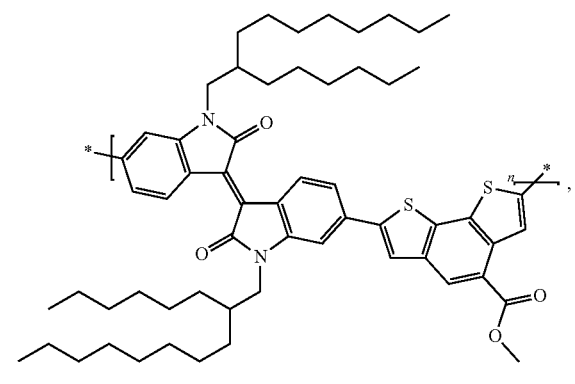
(P-118)
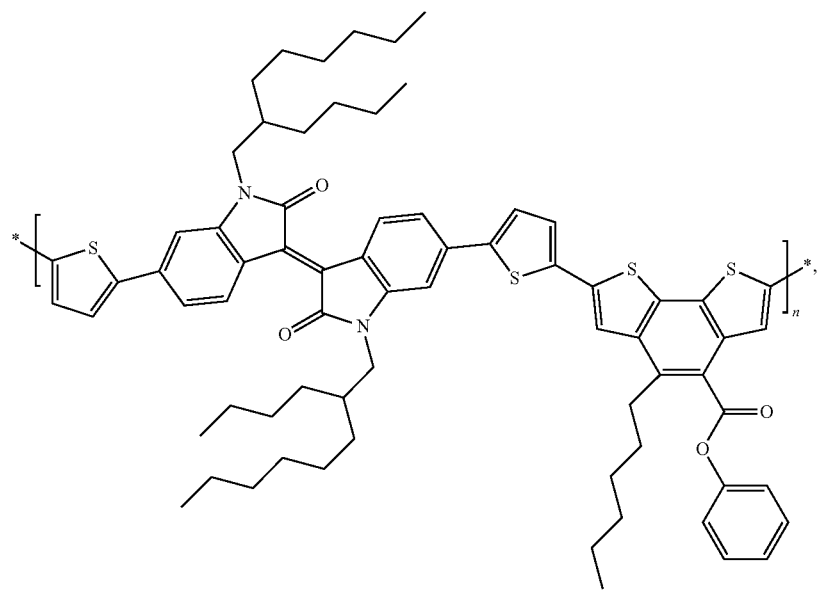

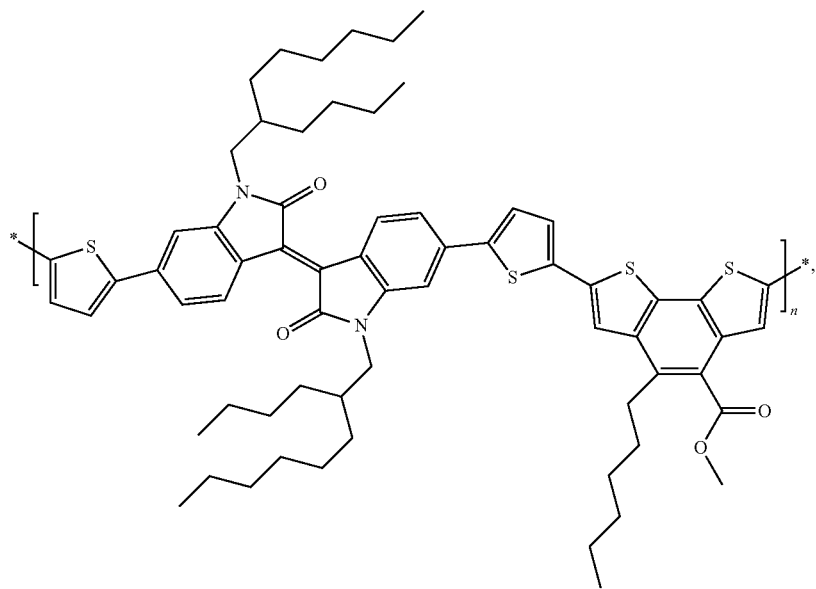
(P-119)
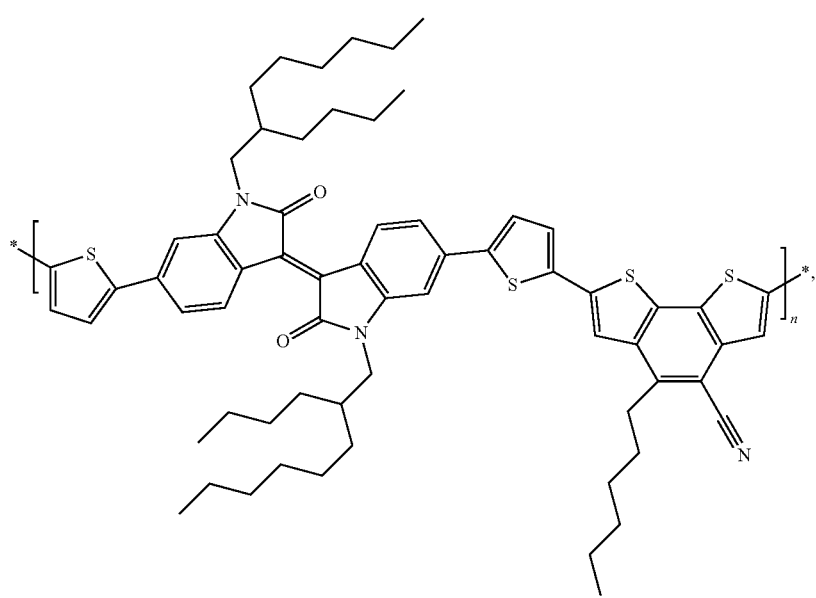
(P-120)

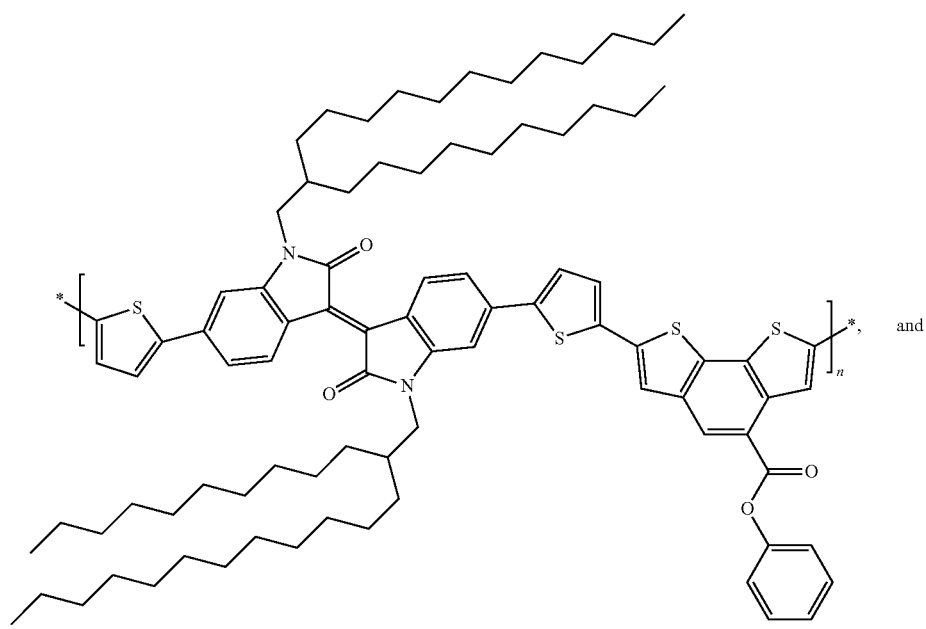
(P-121)
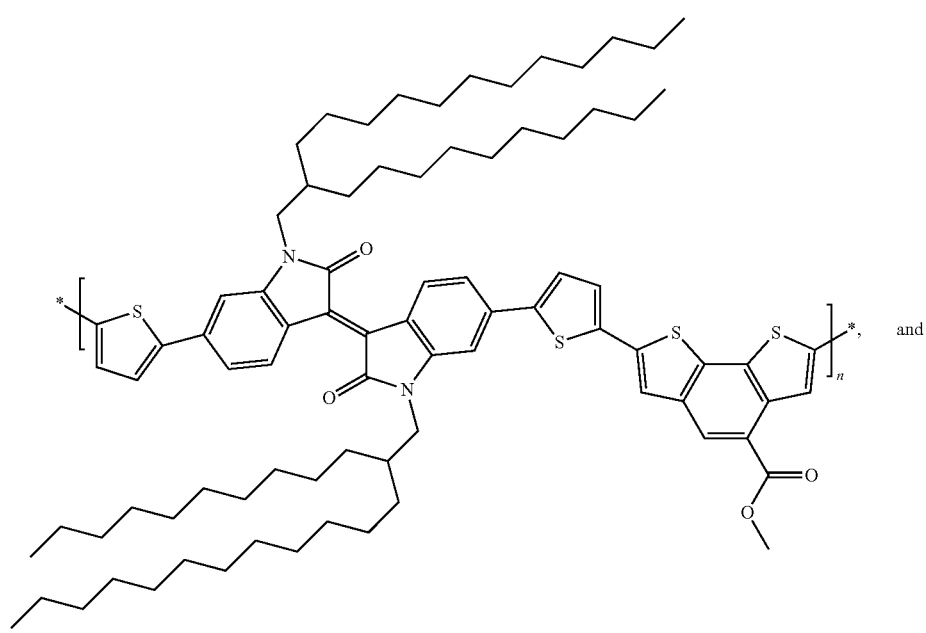
(P-122)

(P-123)

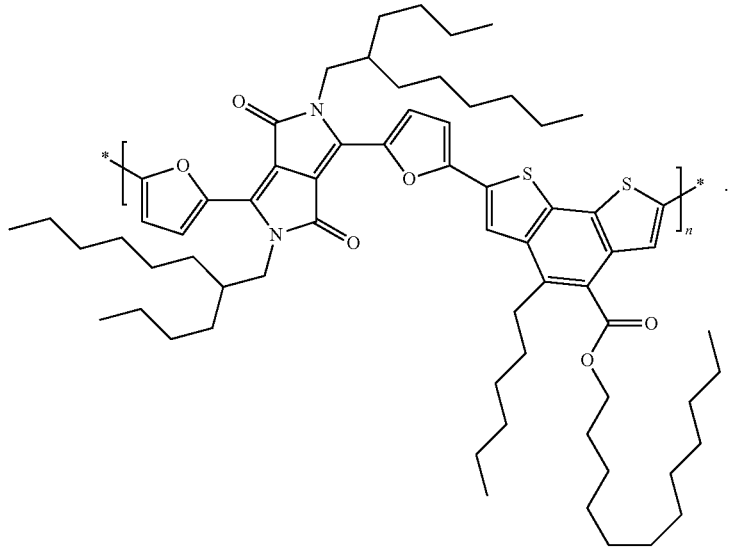

n is 4 to 1000, especially 4 to 200, very especially 5 to 150.

Copolymers of formula III can be obtained, for example, by the Suzuki reaction. The condensation reaction of an aromatic boronate and a halogenide, especially a bromide, commonly referred to as the "Suzuki reaction", is tolerant of the presence of a variety of organic functional groups as reported by N. Miyaura and A. Suzuki in Chemical Reviews, Vol. 95, pp. 457-2483 (1995). Preferred catalysts are 2-dicyclohexylphosphino-2',6'-di-alkoxybiphenyl/palladium(II) acetates, tri-alykl-phosphonium salts/palladium (0) derivatives and tri-alkylphosphine/palladium (0) derivatives. Especially preferred catalysts are 2-dicyclohexylphosphino-2',6'-di-methoxybiphenyl (sPhos)/palladium(II)acetate and, tri-tert-butylphosphonium tetrafluoroborate ((t-Bu)$_3$P*HBF4)/tris(dibenzylideneacetone) dipalladium (0) (Pd$_2$(dba)$_3$) and tri-tert-butylphosphine (t-Bu)$_3$P/tris(dibenzylideneacetone) dipalladium (0) (Pd$_2$(dba)$_3$). This reaction can be applied to preparing high molecular weight polymers and copolymers.

To prepare polymers corresponding to formula III a dihalogenide of formula $X^{10}$-A-$X^{10}$ is reacted with an (equimolar) amount of a diboronic acid or diboronate corresponding to formula

or a dihalogenide of formula

is reacted with an (equimolar) amount of a diboronic acid or diboronate corresponding to formula $X^{11}$-A-$X^{11}$, wherein $X^{10}$ is halogen, especially Cl, Br, or I, very especially Br, and $X^{11}$ is independently in each occurrence —B(OH)$_2$, —B(OY$^1$)$_2$,

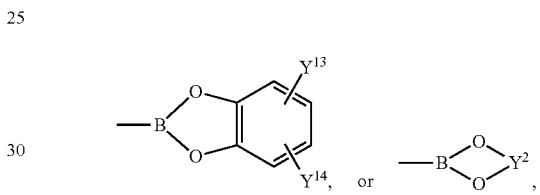

wherein $Y^1$ is independently in each occurrence a $C_1$-$C_{10}$alkyl group and $Y^2$ is independently in each occurrence a $C_2$-$C_{10}$alkylene group, such as —CY$^3$Y$^4$—CY$^5$Y$^6$—, or —CY$^7$Y$^8$—CY$^9$Y$^{10}$—CY$^{11}$Y$^{12}$—, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{10}$alkyl group, especially —C(CH$_3$)$_2$C(CH$_3$)$_2$—, —CH$_2$C(CH$_3$)$_2$CH$_2$—, or —C(CH$_3$)$_2$CH$_2$C(CH$_3$)$_2$—, and $Y^{13}$ and $Y^{14}$ are independently of each other hydrogen, or a $C_1$-$C_{10}$alkyl group, under the catalytic action of Pd and triphenylphosphine. The reaction is typically conducted at about 0° C. to 180° C. in an aromatic hydrocarbon solvent such as toluene, xylene. Other solvents such as dimethylformamide, dioxane, dimethoxyethan and tetrahydrofuran can also be used alone, or in mixtures with an aromatic hydrocarbon. An aqueous base, preferably sodium carbonate or bicarbonate, potassium phosphate, potassium carbonate or bicarbonate is used as activation agent for the boronic acid, boronate and as the HBr scavenger. A polymerization reaction may take 0.2 to 100 hours. Organic bases, such as, for example, tetraalkylammonium hydroxide, and phase transfer catalysts, such as, for example TBAB, can promote the activity of the boron (see, for example, Leadbeater & Marco; Angew. Chem. Int. Ed. Eng. 42 (2003) 1407 and references cited therein). Other variations of reaction conditions are given by T. I. Wallow and B. M. Novak in J. Org. Chem. 59 (1994) 5034-5037; and M. Remmers, M. Schulze, and G. Wegner in Macromol. Rapid Commun. 17 (1996) 239-252. Control of molecular weight is possible by using either an excess of dibromide, diboronic acid, or diboronate, or a chain terminator.

According to the process described in WO2010/136352 the polymerisation is carried out in presence of a) a catalyst/ligand system comprising a palladium catalyst and an organic phosphine or phosphonium compound, b) a base,
c) a solvent or a mixture of solvents, characterized in that the organic phosphine is a trisubstituted phosphine of formula

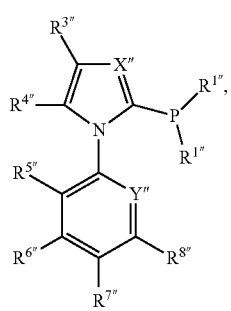

(VI)

or phosphonium salt thereof, wherein X″ independently of Y″ represents a nitrogen atom or a C—R²″ group and Y″ independently of X″ represents a nitrogen atom or a C—R⁹″ group, R¹″ for each of the two R¹″ groups independently of the other represents a radical selected from the group $C_1$-$C_{24}$-alkyl, $C_3$-$C_{20}$-cycloalkyl, which includes especially both monocyclic and also bi- and tri-cyclic cycloalkyl radicals, $C_5$-$C_{14}$-aryl, which includes especially the phenyl, naphthyl, fluorenyl radical, $C_2$-$C_{13}$-heteroaryl, wherein the number of hetero atoms, selected from the group N, O, S, may be from 1 to 2, wherein the two radicals R¹″ may also be linked to one another, and wherein the above-mentioned radicals R¹″ may themselves each be mono- or polysubstituted independently of one another by substituents selected from the group hydrogen, $C_1$-$C_{20}$-alkyl, $C_2$-$C_{20}$-alkenyl, $C_3$-$C_8$-cycloalkyl, $C_2$-$C_9$-hetero-alkyl, $C_2$-$C_9$-heteroaryl, wherein the number of hetero atoms from the group N, O, S may be from 1 to 4, $C_1$-$C_{20}$-alkoxy, hydroxy, amino of the forms NH—($C_1$-$C_{20}$-alkyl), NH—($C_5$-$C_{10}$-aryl), N($C_1$-$C_{20}$-alkyl)$_2$, N($C_1$-$C_{20}$-alkyl) ($C_5$-$C_{10}$-aryl), N($C_5$-$C_{10}$-aryl)$_2$, N($C_1$-$C_{20}$-alkyl/$C_5$-$C_{10}$-aryl)$_3^+$, NH—CO—$C_1$-$C_{20}$-alkyl, NH—CO—$C_5$-$C_{10}$-aryl carboxylato of the forms COOH and COOQ (wherein Q represents either a monovalent cation or $C_1$-$C_8$-alkyl), $C_1$-$C_6$-acyloxy, sulfinato, sulfonato of the forms SO$_3$H and SO$_3$Q′ (wherein Q′ represents either a monovalent cation, $C_1$-$C_{20}$-alkyl, or $C_5$-$C_{10}$-aryl), tri-$C_1$-$C_6$-alkylsilyl, wherein two of the mentioned substituents may also be bridged with one another, R²″-R⁹″ represent a hydrogen, alkyl, alkenyl, cycloalkyl, aromatic or heteroaromatic aryl, O-alkyl, NH-alkyl, N-(alkyl)$_2$, O-(aryl), NH-(aryl), N-(alkyl)(aryl), O—CO-alkyl, O—CO-aryl, F, Si(alkyl)$_3$, CF$_3$, CN, CO$_2$H, COH, SO$_3$H, CONH$_2$, CONH(alkyl), CON(alkyl)$_2$, SO$_2$(alkyl), SO(alkyl), SO(aryl), SO$_2$(aryl), SO$_3$(alkyl), SO$_3$(aryl), S-alkyl, S-aryl, NH—CO(alkyl), CO$_2$(alkyl), CONH$_2$, CO(alkyl), NHCOH, NHCO$_2$(alkyl), CO(aryl), CO$_2$(aryl) radical, wherein two or more adjacent radicals, each independently of the other (s), may also be linked to one another so that a condensed ring system is present and wherein in R²″ to R⁹″ alkyl represents a hydrocarbon radical having from 1 to 20 carbon atoms which may in each case be linear or branched, alkenyl represents a mono- or polyunsaturated hydrocarbon radical having from 2 to 20 carbon atoms which may in each case be linear or branched, cycloalkyl represents a hydrocarbon having from 3 to 20 carbon atoms, aryl represents a 5- to 14-membered aromatic radical, wherein from one to four carbon atoms in the aryl radical may also be replaced by hetero atoms from the group nitrogen, oxygen and sulfur so that a 5- to 14-membered heteroaromatic radical is present, wherein the radicals R²″ to R⁹″ may also carry further substituents as defined for R¹″. The organic phosphines and their synthesis are described in WO2004101581. Preferred organic phosphines are selected from trisubstituted phosphines of formula

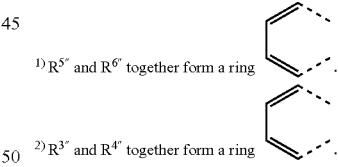

| Cpd. | R¹″ | R⁵″ | R⁶″ | R³″ | R⁴″ |
|------|-----|-----|-----|-----|-----|
| A-1 | H₃C-C(CH₃)₂-CH₃ (tert-butyl) | H | H | H | H |
| A-2 | cyclohexyl | H | H | H | H |
| A-3 | phenyl | H | H | H | H |
| A-4 | adamantyl | H | H | H | H |
| A-5 | cyclohexyl | —OCH₃ | H | H | H |
| A-6 | cyclohexyl | 1) | 1) | H | H |
| A-7 | H₃C-C(CH₃)₂-CH₃ | 1) | 1) | H | H |
| A-8 | phenyl | 1) | 1) | H | H |
| A-9 | adamantyl | 1) | 1) | H | H |
| A-10 | cyclohexyl | H | H | 2) | 2) |
| A-11 | H₃C-C(CH₃)₂-CH₃ | H | H | 2) | 2) |
| A-12 | phenyl | H | H | 2) | 2) |
| A-13 | adamantyl | H | H | 2) | 2) |

1) R⁵″ and R⁶″ together form a ring

2) R³″ and R⁴″ together form a ring

Examples of preferred catalysts include the following compounds:

palladium(II) acetylacetonate, palladium(0) dibenzylidene-acetone complexes, palladium(II) propionate, Pd$_2$(dba)$_3$: [tris(dibenzylideneacetone) dipalladium(0)], Pd(dba)$_2$: [bis(dibenzylideneacetone) palladium(0)], Pd(PR$_3$)$_2$, wherein PR$_3$ is a trisubstituted phosphine of formula VI, Pd(OAc)$_2$: [palladium(II) acetate], palladium(II) chloride, palladium(II) bromide, lithium tetrachloropalladate(II), PdCl$_2$(PR$_3$)$_2$; wherein PR$_3$ is a trisubstituted phosphine of formula VI; palladium(0) diallyl ether complexes, palladium (II) nitrate, PdCl$_2$(PhCN)$_2$: [dichlorobis(benzonitrile) palladium(II)], PdCl$_2$(CH$_3$CN): [dichlorobis(acetonitrile) palladium(II)], and PdCl₂(COD): [dichloro(1,5-cyclooctadiene) palladium (II)].

Especially preferred are PdCl₂, Pd₂(dba)₃, Pd(dba)₂, Pd(OAc)₂, or Pd(PR₃)₂. Most preferred are Pd₂(dba)₃ and Pd(OAc)₂.

The palladium catalyst is present in the reaction mixture in catalytic amounts. The term "catalytic amount" refers to an amount that is clearly below one equivalent of the (hetero)aromatic compound(s), preferably 0.001 to 5 mol-%, most preferably 0.001 to 1 mol-%, based on the equivalents of the (hetero)aromatic compound(s) used.

The amount of phosphines or phosphonium salts in the reaction mixture is preferably from 0.001 to 10 mol-%, most preferably 0.01 to 5 mol-%, based on the equivalents of the (hetero)aromatic compound(s) used. The preferred ratio of Pd:phosphine is 1:4.

The base can be selected from all aqueous and nonaqueous bases and can be inorganic, or organic. It is preferable that at least 1.5 equivalents of said base per functional boron group is present in the reaction mixture. Suitable bases are, for example, alkali and alkaline earth metal hydroxides, carboxylates, carbonates, fluorides and phosphates such as sodium and potassium hydroxide, acetate, carbonate, fluoride and phosphate or also metal alcoholates. It is also possible to use a mixture of bases. The base is preferably a lithium salt, such as, for example, lithium alkoxides (such as, for example, lithium methoxide and lithium ethoxide), lithium hydroxide, carboxylate, carbonate, fluoride and/or phosphate.

The at present most preferred base is aqueous LiOHxH₂O (monohydrate of LiOH) and (waterfree) LiOH.

The reaction is typically conducted at about 0° C. to 180° C., preferably from 20 to 160° C., more preferably from 40 to 140° C. and most preferably from 40 to 120° C. A polymerization reaction may take 0.1, especially 0.2 to 100 hours.

In a preferred embodiment of the present invention the solvent is THF, the base is LiOH*H₂O and the reaction is conducted at reflux temperature of THF (about 65° C.).

The solvent is for example selected from toluene, xylenes, anisole, THF, 2-methyltetrahydrofuran, dioxane, chlorobenzene, fluorobenzene or solvent mixtures comprising one or more solvents like e.g. THF/toluene and optionally water. Most preferred is THF, or THF/water.

Advantageously, the polymerisation is carried out in presence of
a) palladium(II) acetate, or Pd₂(dba)₃, (tris(dibenzylideneacetone)dipalladium(0)) and an organic phosphine A-1 to A-13,
b) LiOH, or LiOHxH₂O; and
c) THF, and optionally water. If the monohydrate of LiOH is used, no water needs to be added. The palladium catalyst is present in an amount of preferably about 0.5 mol-%, based on the equivalents of the (hetero)aromatic compound(s) used. The amount of phosphines or phosphonium salts in the reaction mixture is preferably about 2 mol-%, based on the equivalents of the (hetero)aromatic compound(s) used. The preferred ratio of Pd:phosphine is about 1:4.

Preferably the polymerization reaction is conducted under inert conditions in the absence of oxygen. Nitrogen and more preferably argon are used as inert gases.

The process described in WO2010/136352 is suitable for large-scale applications, is readily accessible and convert starting materials to the respective polymers in high yield, with high purity and high selectivity. The process can provide polymers having weight average molecular weights of at least 10,000, more preferably at least 20,000, most preferably at least 30,000. The at present most preferred polymers have a weight average molecular weight of 30,000 to 80,000 Daltons. Molecular weights are determined according to high-temperature gel permeation chromatography (HT-GPC) using polystyrene standards. The polymers preferably have a polydispersibility of 1.01 to 10, more preferably 1.1 to 3.0, most preferred 1.5 to 2.5.

If desired, a monofunctional aryl halide or aryl boronate, such as, for example,

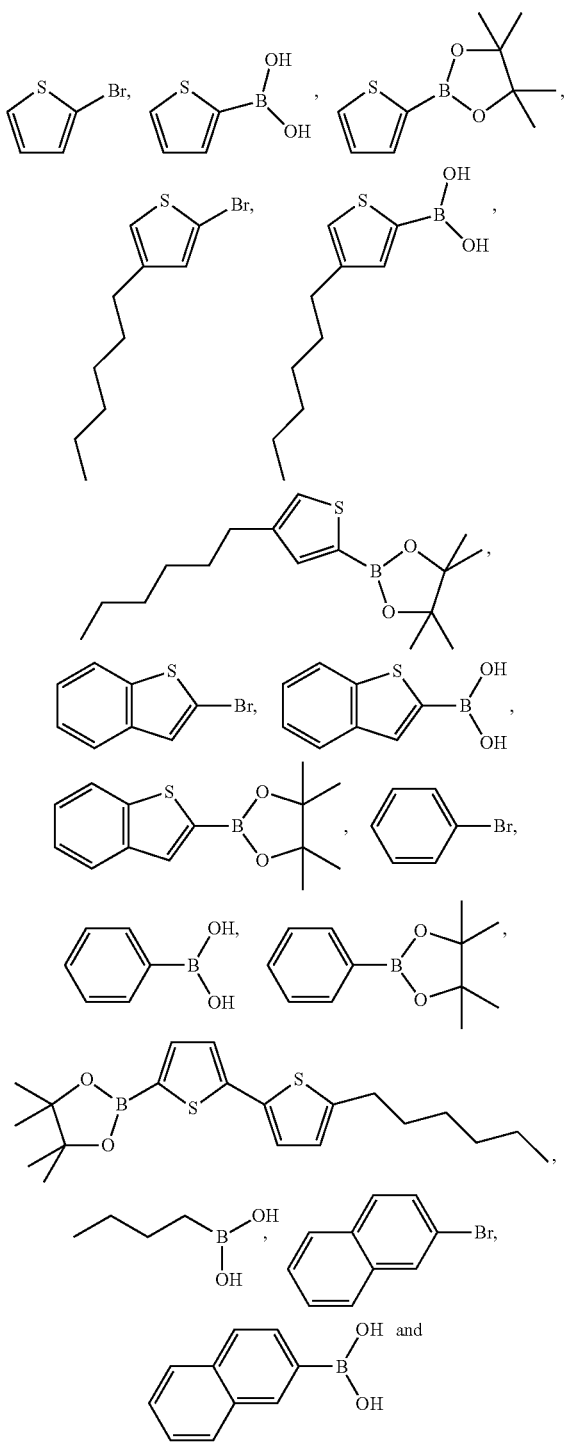

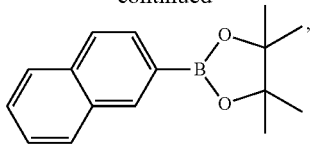

may be used as a chain-terminator in such reactions, which will result in the formation of a terminal aryl group.

It is possible to control the sequencing of the monomeric units in the resulting copolymer by controlling the order and composition of monomer feeds in the Suzuki reaction.

The polymers of the present invention can also be synthesized by the Stille coupling (see, for example, Babudri et al, J. Mater. Chem., 2004, 14, 11-34; J. K. Stille, Angew. Chemie Int. Ed. Engl. 1986, 25, 508). To prepare polymers corresponding to formula III a dihalogenide of formula $X^{10}$-A-$X^{10}$ is reacted with a compound of formula $X^{11'}$—COM$^1$-$X^{11'}$, or a dihalogenide of formula $X^{10}$—COM$^1$-$X^{10}$ is reacted with a compound of formula $X^{11'}$-A-$X^{11'}$, wherein $X^{11'}$ is a group —SnR$^{207}$R$^{208}$R$^{209}$ and $X^{10}$ is as defined above, in an inert solvent at a temperature in range from 0° C. to 200° C. in the presence of a palladium-containing catalyst, wherein R$^{207}$, R$^{208}$ and R$^{209}$ are identical or different and are H or C$_1$-C$_6$alkyl, wherein two radicals optionally form a common ring and these radicals are optionally branched or unbranched. It must be ensured here that the totality of all monomers used has a highly balanced ratio of organotin functions to halogen functions. In addition, it may prove advantageous to remove any excess reactive groups at the end of the reaction by end-capping with monofunctional reagents. In order to carry out the process, the tin compounds and the halogen compounds are preferably introduced into one or more inert organic solvents and stirred at a temperature of from 0 to 200° C., preferably from 30 to 170° C. for a period of from 1 hour to 200 hours, preferably from 5 hours to 150 hours. The crude product can be purified by methods known to the person skilled in the art and appropriate for the respective polymer, for example repeated re-precipitation or even by dialysis.

Suitable organic solvents for the process described are, for example, ethers, for example diethyl ether, dimethoxyethane, diethylene glycol dimethyl ether, tetrahydrofuran, dioxane, dioxolane, diisopropyl ether and tert-butyl methyl ether, hydrocarbons, for example hexane, isohexane, heptane, cyclohexane, benzene, toluene and xylene, alcohols, for example methanol, ethanol, 1-propanol, 2-propanol, ethylene glycol, 1-butanol, 2-butanol and tertbutanol, ketones, for example acetone, ethyl methyl ketone and isobutyl methyl ketone, amides, for example dimethylformamide (DMF), dimethylacetamide and N-methylpyrrolidone, nitriles, for example acetonitrile, propionitrile and butyronitrile, and mixtures thereof.

The palladium and phosphine components should be selected analogously to the description for the Suzuki variant.

Alternatively, the polymers of the present invention can also be synthesized by the Negishi reaction using a zinc reagent A-(ZnX$^{12}$)$_2$, wherein X$^{12}$ is halogen and halides, and COM$^1$-(X$^{23}$)$_2$, wherein X$^{23}$ is halogen or triflate, or using A-(X$^{23}$)$_2$ and COM$^1$-(ZnX$^{23}$)$_2$. Reference is, for example, made to E. Negishi et al., Heterocycles 18 (1982) 117-22.

Alternatively, the polymers of the present invention can also be synthesized by the Hiyama reaction using a organosilicon reagent A-(SiR$^{210}$R$^{211}$R$^{212}$)$_2$, wherein R$^{210}$, R$^{211}$ and R$^{212}$ are identical or different and are halogen, or C$_1$-C$_6$alkyl, and COM$^1$-(X$^{23}$)$_2$, wherein X$^{23}$ is halogen or triflate, or using A-(X$^{23}$)$_2$ and COM$^1$-(SiR$^{210}$R$^{211}$R$^{212}$)$_2$. Reference is, for example, made to T. Hiyama et al., Pure Appl. Chem. 66 (1994) 1471-1478 and T. Hiyama et al., Synlett (1991) 845-853.

Homopolymers of the type (A)$_n$ can be obtained via Yamamoto coupling of dihalides $X^{10}$-A-$X^{10}$, where $X^{10}$ is halogen, preferably bromide. Alternatively homopolymers of the type (A)$_n$ can be obtained via oxidative polymerization of units $X^{10}$-A-$X^{10}$, where $X^{10}$ is hydrogen, e.g. with FeCl$_3$ as oxidizing agent.

Compound of the formula $X^2$-A-$X^{2'}$ (V) are new, intermediates of the polymers of the present invention and form a further subject of the present invention. $X^2$ and $X^{2'}$ are independently of each other halogen, ZnX$^{12}$, —SnR$^{207}$R$^{208}$R$^{209}$, wherein R$^{207}$, R$^{208}$ and R$^{209}$ are identical or different and are H or C$_1$-C$_6$alkyl, wherein two radicals optionally form a common ring and these radicals are optionally branched or unbranched and X$^{12}$ is a halogen atom; SiR$^{210}$R$^{211}$R$^{212}$, wherein R$^{210}$, R$^{211}$ and R$^{212}$ are identical or different and are halogen, or C$_1$-C$_6$alkyl; —OS(O)$_2$CF$_3$, —OS(O)$_2$-aryl, —OS(O)$_2$CH$_3$, —B(OH)$_2$, —B(OY$^1$)$_2$,

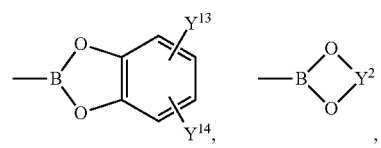

—BF$_4$Na, or —BF$_4$K, wherein Y$^1$ is independently in each occurrence a C$_1$-C$_{10}$alkyl group and Y$^2$ is independently in each occurrence a C$_2$-C$_{10}$alkylene group and Y$^{13}$ and Y$^{14}$ are independently of each other hydrogen, or a C$_1$-C$_{10}$alkyl group.

A possible synthesis route for monomers useful in the preparation of polymers, comprising repeating units of formula (I), wherein R$^1$ is an alkyl group and R$^2$ is an ester group is shown below:

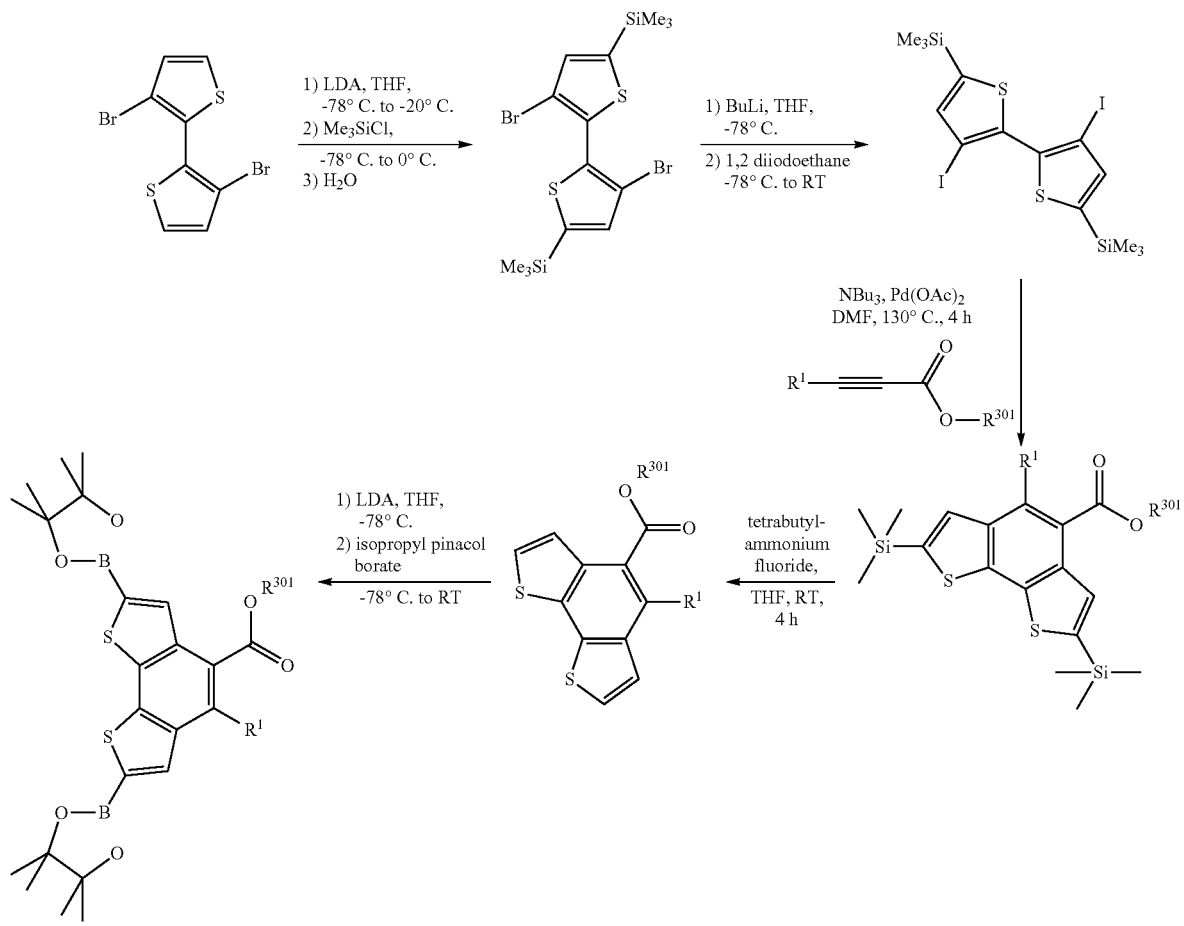
A possible route for monomers, wherein $R^1$ is hydrogen, is shown below:
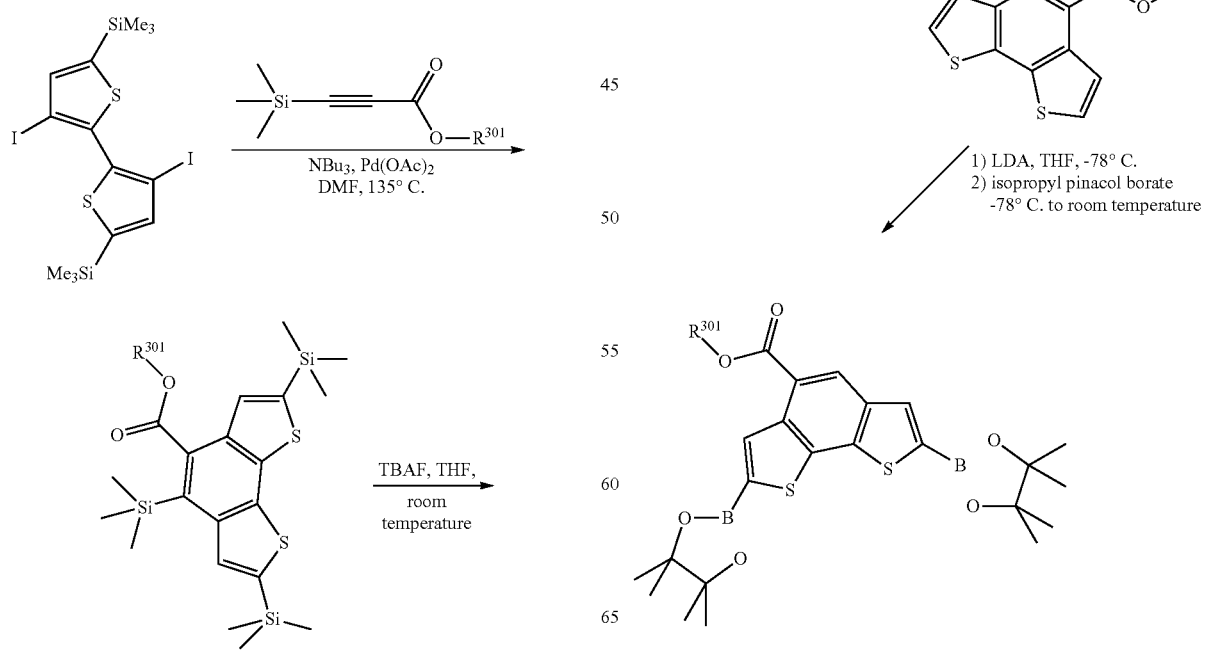

Further modifications of the ester group could be achieved from the carboxylic acid, as described below:
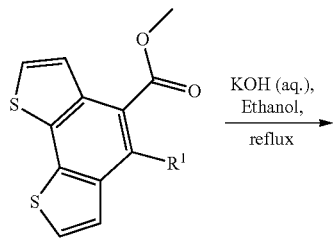
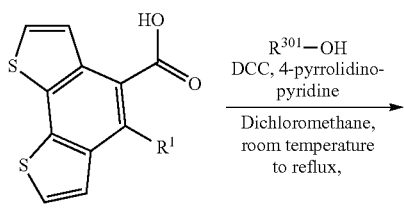
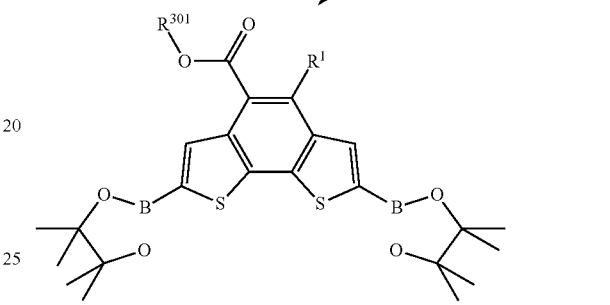
Monomers, wherein $R^2$ is a —CN group may be prepared via the following route:
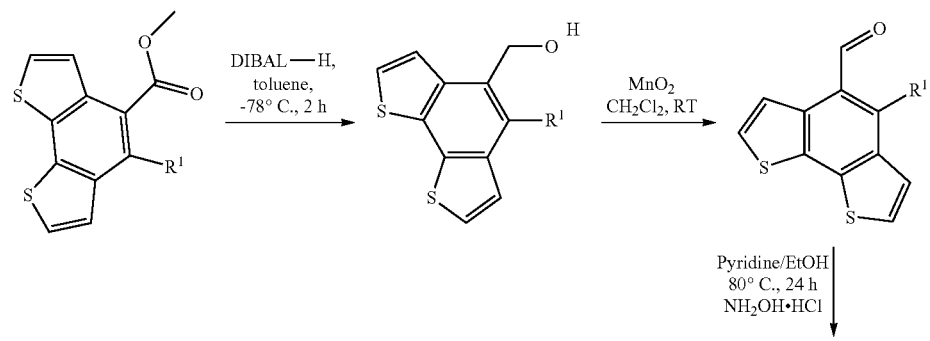
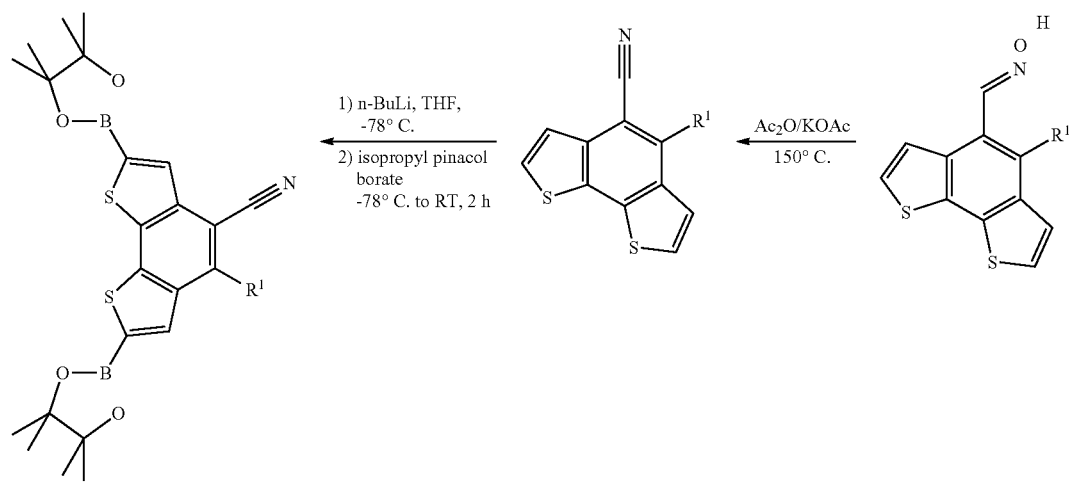

A possible synthesis route for monomers useful in the preparation of polymers, comprising repeating units of formula (I), wherein $R^2$ is a ketone, is shown below:

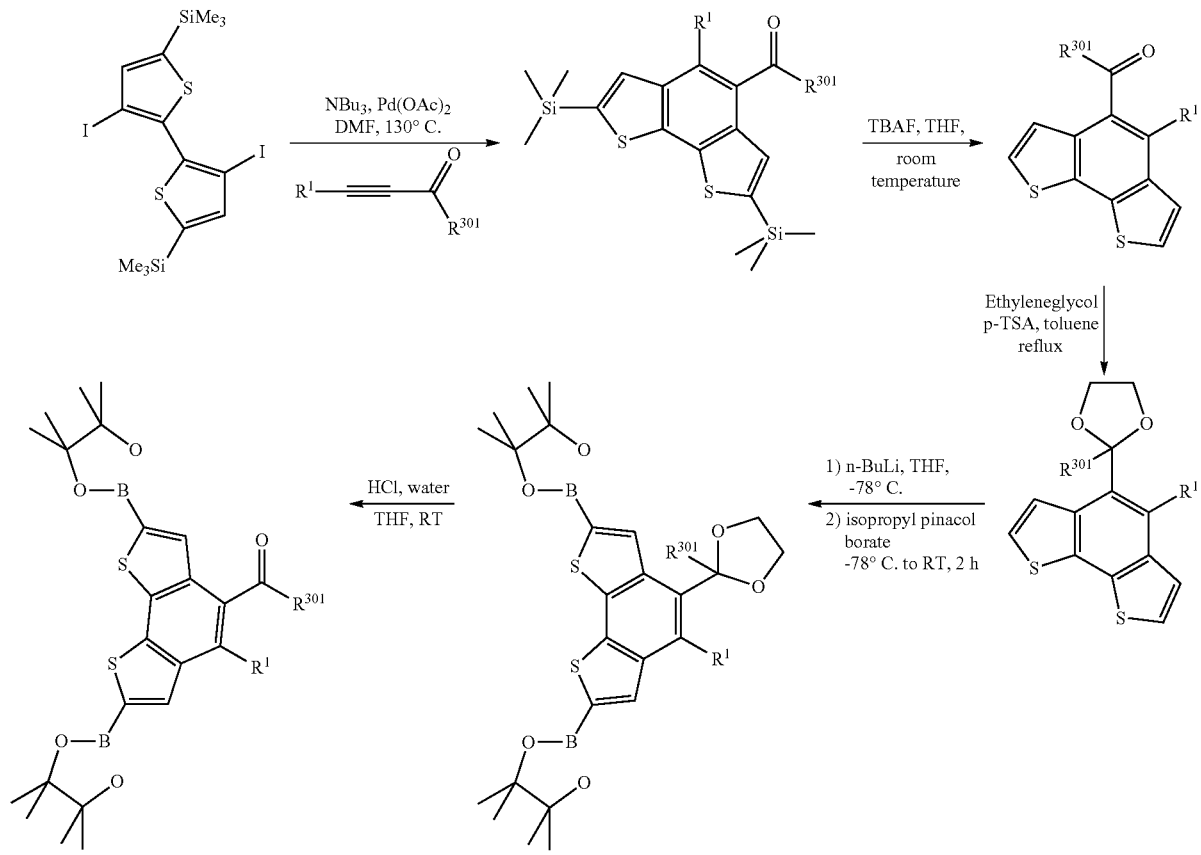

Halogen is fluorine, chlorine, bromine and iodine.

The $C_1$-$C_{100}$alkyl group is preferably a $C_1$-$C_{38}$alkyl group, especially a $C_1$-$C_{25}$alkyl group. Reference is made to the definition of $R^{201}$.

$C_1$-$C_{25}$alkyl ($C_1$-$C_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl or pentacosyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_2$-$C_{25}$alkenyl ($C_2$-$C_{18}$alkenyl) groups are straight-chain or branched alkenyl groups, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_{2-25}$alkynyl ($C_{2-18}$alkynyl) is straight-chain or branched and preferably $C_{2-8}$ alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

A halogenated $C_1$-$C_{25}$alkyl group (halogenated $C_1$-$C_{18}$alkyl group) is a branched or unbranched radical, wherein all, or part of the hydrogen atoms of the corresponding alkyl group have been replaced by halogen atoms.

A cycloalkyl-alkyl group is an alkyl group substituted by a cycloalkyl group, e.g. cyclohexyl-methyl.

A "cycloalkenyl group" means an unsaturated alicyclic hydrocarbon group containing one or more double bonds, such as cyclopentenyl, cyclopentadienyl, cyclohexenyl and the like, which may be unsubstituted or substituted by one or more aliphatic and/or cycloaliphatic hydrocarbon groups and/or condensed with phenyl groups.

$C_1$-$C_{25}$alkoxy groups ($C_1$-$C_{18}$alkoxy groups) are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy and 2-ethylhexoxy, preferably $C_1$-$C_4$alkoxy such as typically methoxy, ethoxy, n-propoxy, isopropoxy, n-butoxy, sec.-butoxy, isobutoxy, tert.-butoxy. The term "alkylthio group" means the same groups as the alkoxy groups, except that the oxygen atom of the ether linkage is replaced by a sulfur atom.

The $C_1$-$C_{100}$fluoroalkyl group is typically a $C_1$-$C_{25}$fluoroalkyl group, especially a $C_1$-$C_{18}$fluoroalkyl group. $C_1$-$C_{18}$fluoroalkyl, especially $C_1$-$C_4$fluoroalkyl, is a branched or unbranched radical, wherein all, or part of the hydrogen atoms of the corresponding alkyl group have been replaced by fluorine atoms, such as for example —$CF_3$, —$CF_2CF_3$, —$CF_2CF_2CF_3$, —$CF(CF_3)_2$, —$(CF_2)_3CF_3$, and —$C(CF_3)_3$.

The term "carbamoyl group" is typically a $C_{1-18}$carbamoyl radical, preferably $C_{1-8}$carbamoyl radical, which may be unsubstituted or substituted, such as, for example, carbamoyl, methylcarbamoyl, ethylcarbamoyl, n-butylcarbamoyl, tert-butylcarbamoyl, dimethylcarbamoyloxy, morpholinocarbamoyl or pyrrolidinocarbamoyl.

A cycloalkyl group is typically $C_3$-$C_{12}$cycloalkyl, such as, for example, cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted. The cycloalkyl group, in particular a cyclohexyl group, can be condensed one or two times by phenyl which can be substituted one to three times with $C_1$-$C_4$-alkyl, halogen and cyano. Examples of such condensed cyclohexyl groups are:

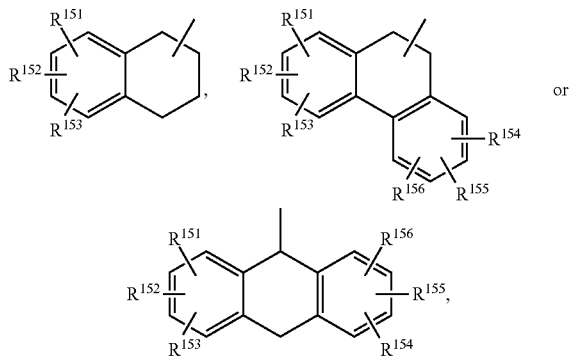

in particular

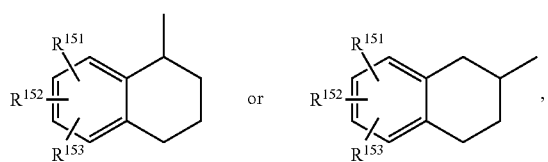

wherein $R^{151}$, $R^{152}$, $R^{153}$, $R^{154}$, $R^{155}$ and $R^{156}$ are independently of each other $C_1$-$C_8$-alkyl, $C_1$-$C_8$-alkoxy, halogen and cyano, in particular hydrogen.

$C_6$-$C_{24}$aryl ($C_6$-$C_{18}$aryl) is typically phenyl, indenyl, azulenyl, naphthyl, biphenyl, as-indacenyl, s-indacenyl, acenaphthylenyl, fluorenyl, phenanthryl, fluoranthenyl, triphenlenyl, chrysenyl, naphthacen, picenyl, perylenyl, pentaphenyl, hexacenyl, pyrenyl, or anthracenyl, preferably phenyl, 1-naphthyl, 2-naphthyl, 4-biphenyl, 9-phenanthryl, 2- or 9-fluorenyl, 3- or 4-biphenyl, which may be unsubstituted or substituted. Examples of $C_6$-$C_{12}$aryl are phenyl, 1-naphthyl, 2-naphthyl, 3- or 4-biphenyl, 2- or 9-fluorenyl or 9-phenanthryl, which may be unsubstituted or substituted.

$C_7$-$C_{25}$aralkyl ($C_7$-$C_{25}$arylalkyl) is typically benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably $C_7$-$C_{18}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7$-$C_{12}$aralkyl such as benzyl, 2-benzyl-2-propyl, β-phenyl-ethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted. Preferred examples are benzyl, 2-phenylethyl, 3-phenylpropyl, naphthylethyl, naphthylmethyl, and cumyl.

Heteroaryl is typically $C_2$-$C_{20}$heteroaryl, i.e. a ring with five to seven ring atoms or a condensed ring system, wherein nitrogen, oxygen or sulfur are the possible hetero atoms, and is typically an unsaturated heterocyclic group with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl or phenoxazinyl, which can be unsubstituted or substituted.

The term "silyl group" means a group of formula —$SiR^{501}R^{502}R^{503}$, especially —$Si(R^{501})_3$, wherein $R^{501}$, $R^{502}$ and $R^{503}$ are independently of each other a $C_1$-$C_8$alkyl group, in particular a $C_1$-$C_4$ alkyl group, a $C_6$-$C_{24}$aryl group, or a $C_7$-$C_{12}$aralkylgroup, such as a trimethylsilyl group.

Possible substituents of the above-mentioned groups are $C_1$-$C_8$alkyl, a hydroxyl group, a mercapto group, $C_1$-$C_8$alkoxy, $C_1$-$C_8$alkylthio, halogen, especially F; halo-$C_1$-$C_8$alkyl, especially fluoro-$C_1$-$C_8$alkyl, a cyano group, a carbamoyl group, a nitro group or a silyl group, especially $C_1$-$C_8$alkyl, $C_1$-$C_8$alkoxy, $C_1$-$C_8$alkylthio, halogen, halo-$C_1$-$C_8$alkyl, or a cyano group.

$C_1$-$C_{25}$alkyl ($C_1$-$C_{18}$alkyl) interrupted by one or more O is, for example, $(CH_2CH_2O)_{1-9}$—$R^x$, where $R^x$ is H or $C_1$-$C_{10}$alkyl, $CH_2$—$CH(OR^{y'})$—$CH_2$—O—$R^y$, where $R^y$ is $C_1$-$C_{18}$alkyl, and $R^{y'}$ embraces the same definitions as $R^y$ or is H.

If a substituent, such as, for example $R^3$, occurs more than one time in a group, it can be different in each occurrence.

The present invention also relates to the use of the polymers, or compounds in an organic, electronic device.

The organic, electronic device is, for example, an organic electroluminescent device (OLED), a polymeric electroluminescent device (PLED), an organic integrated circuit (O-IC), an organic field-effect transistor (O-FET), an organic thin-film transistor (O-TFT), an organic light-emitting transistor (O-LET), an organic solar cell (O-SC), an organic optical detector, an organic photoreceptor, an organic field-quench device (O-FQD), a light-emitting electrochemical cell (LEC), or an organic laser diode (O-laser).

For the purposes of the present invention, it is preferred for the polymer according to the invention to be in the form of a layer (or to be present in a layer) in the electronic device. The polymer according to the invention can be present in the form of a hole-transport, hole-injection, emitter, electron-transport, electron-injection, charge-blocking and/or chargegeneration layer. The polymers according to the invention may be, for example, employed as emitting material in an emitting layer.

It may additionally be preferred to use the polymer not as the pure substance, but instead as a mixture (blend) together with further polymeric, oligomeric, dendritic or low-molecular-weight substances of any desired type. These may, for example, improve the electronic properties.

A mixture containing a polymer of the present invention results in a semi-conducting layer comprising a polymer of the present invention (typically 5% to 99.9999% by weight, especially 20 to 85% by weight) and at least another material. The other material can be, but is not restricted to a fraction of the same polymer of the present invention with different molecular weight, another polymer of the present invention, a semi-conducting polymer, organic small molecules, carbon nanotubes, a fullerene derivative, inorganic particles (quantum dots, quantum rods, quantum tripods, TiO$_2$, ZnO etc.), conductive particles (Au, Ag etc.), insulator materials like the ones described for the gate dielectric (PET, PS etc.).

The polymers of the present invention can be blended with small molecules described, for example, in WO2009/047104, WO2010108873, WO09/047104, U.S. Pat. No. 6,690,029, WO2007082584, and WO2008107089:
  WO2007082584:

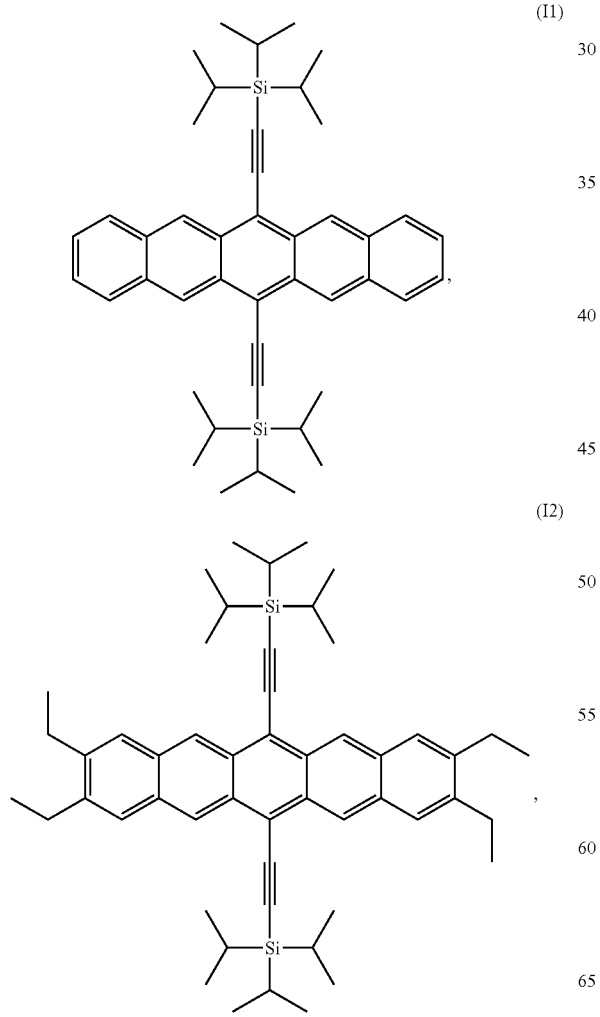

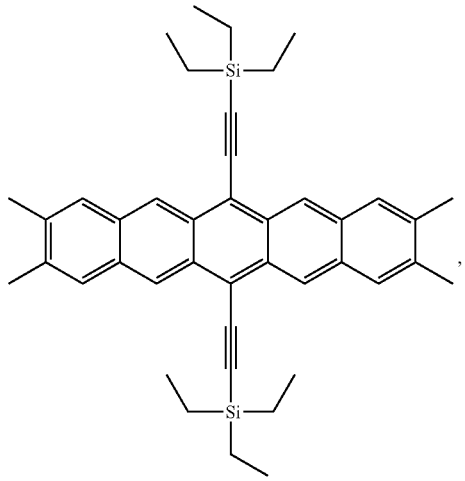

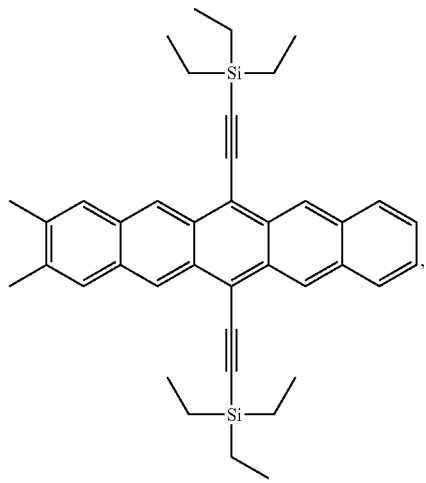

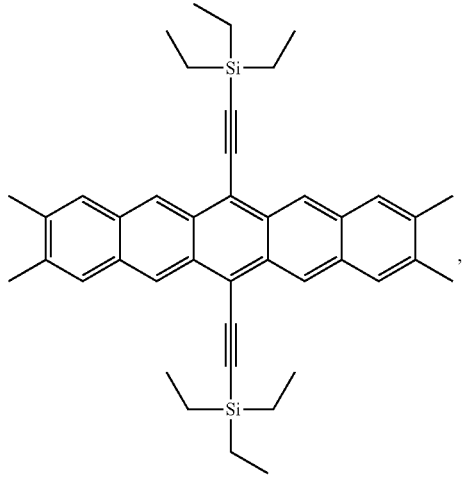

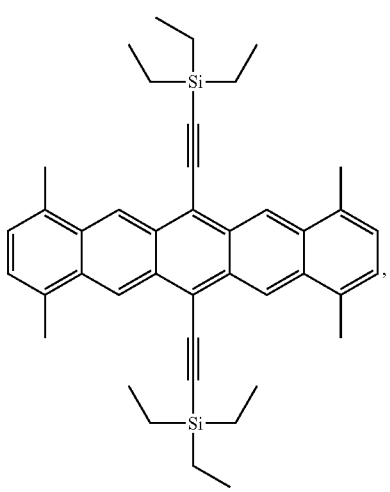 (I6)

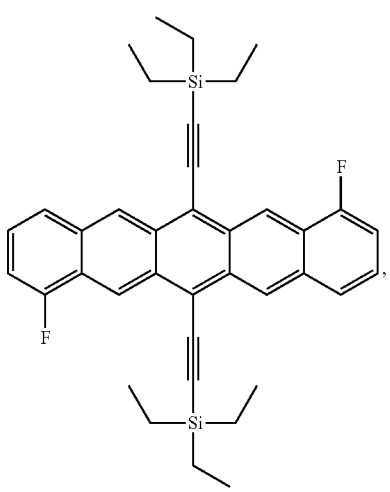 (I7)

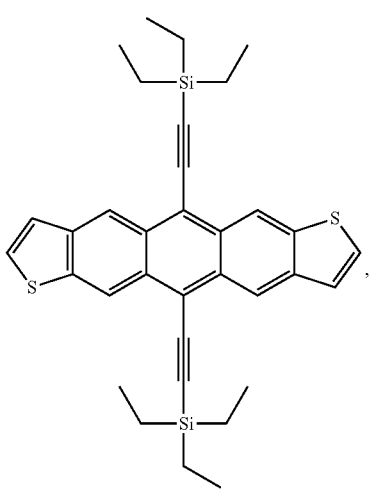 (I8)

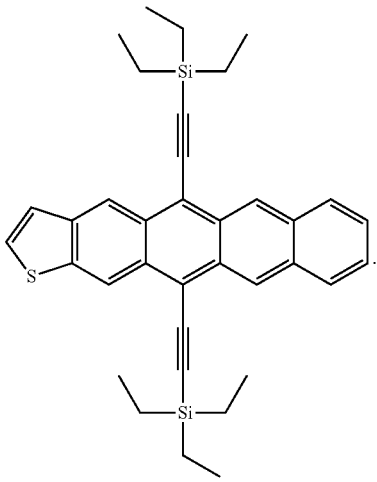 (I9)

WO2008107089:

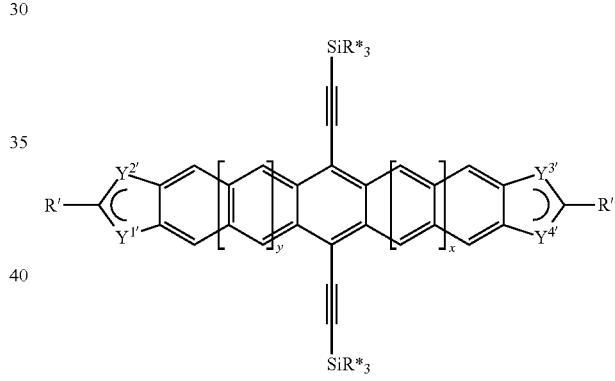

wherein one of $Y^{1'}$ and $Y^{2'}$ denotes —CH= or =CH— and the other denotes —X*—, one of $Y^{3'}$ and $Y^{4'}$ denotes —CH= or =CH— and the other denotes —X*—, X* is —O—, —S—, —Se— or —NR'''—, R* is cyclic, straight-chain or branched alkyl or alkoxy having 1 to 20 C-atoms, or aryl having 2-30 C-atoms, all of which are optionally fluorinated or perfluorinated, R' is H, F, Cl, Br, I, CN, straight-chain or branched alkyl or alkoxy having 1 to 20 C-atoms and optionally being fluorinated or perfluorinated, optionally fluorinated or perfluorinated aryl having 6 to 30 C-atoms, or CO₂R", with R" being H, optionally fluorinated alkyl having 1 to 20 C-atoms, or optionally fluorinated aryl having 2 to 30 C-atoms, R''' is H or cyclic, straight-chain or branched alkyl with 1 to 10 C-atoms, y is 0, or 1, x is 0, or 1.

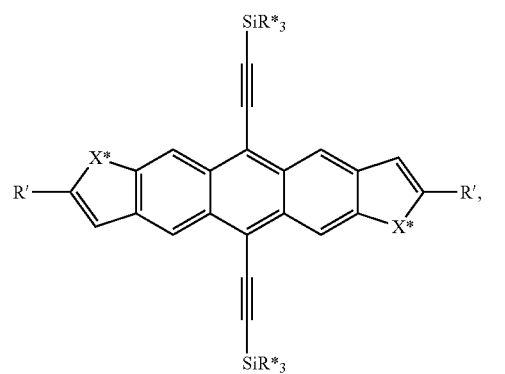

A1

A2

B1

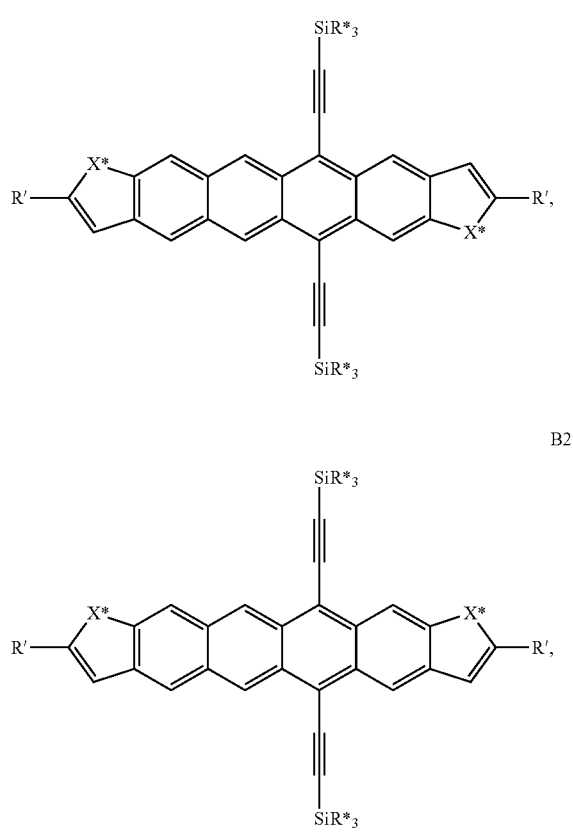

B2

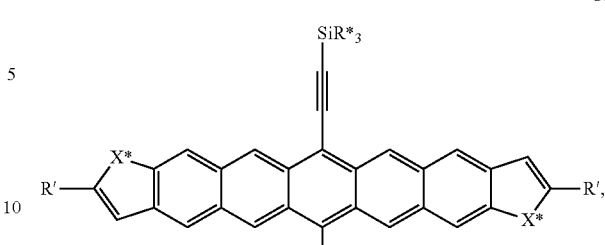

C1

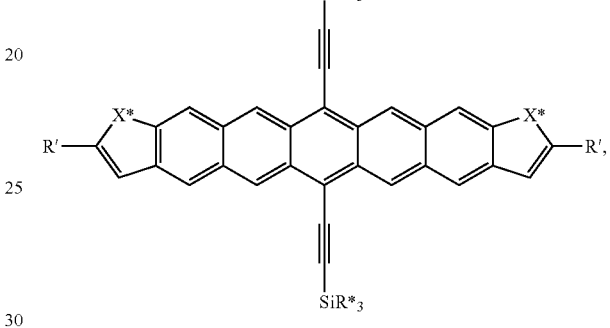

C2

The polymer can contain a small molecule, or a mixture of two, or more small molecule compounds.

Accordingly, the present invention also relates to an organic semiconductor material, layer or component, comprising a polymer according to the present invention.

The polymers of the invention can be used as the semiconductor layer in semiconductor devices. Accordingly, the present invention also relates to semiconductor devices, comprising a polymer of the present invention, or an organic semiconductor material, layer or component. The semiconductor device is especially an organic photovoltaic (PV) device (solar cell), a photodiode, or an organic field effect transistor.

The polymer of the (present) invention is a polymer, comprising repeating units of formula (I), especially (Ia), or (Ib). The polymer of the invention is more preferred a polymer of formula (III) and most preferred a polymer of formula (IIIa-1), (IIIa-2), (IIIa-3), (IIIa-4), (IIIb-1), (IIIb-2), (IIIb-3), or (IIIb-4).

The polymers of the invention can be used alone or in combination as the organic semiconductor layer of the semiconductor device. The layer can be provided by any useful means, such as, for example, vapor deposition (for materials with relatively low molecular weight) and printing techniques. The compounds of the invention may be sufficiently soluble in organic solvents and can be solution deposited and patterned (for example, by spin coating, dip coating, ink jet printing, gravure printing, flexo printing, offset printing, screen printing, microcontact (wave)-printing, drop or zone casting, or other known techniques).

The polymers of the invention can be used in integrated circuits comprising a plurality of OTFTs, as well as in various electronic articles. Such articles include, for example, radiofrequency identification (RFID) tags, backplanes for flexible displays (for use in, for example, personal computers, cell phones, or handheld devices), smart cards, memory devices, sensors (e.g. light-, image-, bio-, chemo-, mechanical- or temperature sensors), especially photodiodes, or security devices and the like.

A further aspect of the present invention is an organic semiconductor material, layer or component comprising one or more polymers of the present invention. A further aspect is the use of the polymers or materials of the present invention in an organic photovoltaic (PV) device (solar cell), a photodiode, or an organic field effect transistor (OFET). A further aspect is an organic photovoltaic (PV) device (solar cell), a photodiode, or an organic field effect transistor (OFET) comprising a polymer or material of the present invention.

The polymers of the present invention are typically used as organic semiconductors in form of thin organic layers or films, preferably less than 30 microns thick. Typically the semiconducting layer of the present invention is at most 1 micron (=1 µm) thick, although it may be thicker if required. For various electronic device applications, the thickness may also be less than about 1 micron thick. For example, for use in an OFET the layer thickness may typically be 100 nm or less. The exact thickness of the layer will depend, for example, upon the requirements of the electronic device in which the layer is used.

For example, the active semiconductor channel between the drain and source in an OFET may comprise a layer of the present invention.

An OFET device according to the present invention preferably comprises:
  a source electrode,
  a drain electrode,
  a gate electrode,
  a semiconducting layer,
  one or more gate insulator layers, and
  optionally a substrate, wherein the semiconductor layer comprises one or more polymers of the present invention.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

Preferably the OFET comprises an insulator having a first side and a second side, a gate electrode located on the first side of the insulator, a layer comprising a polymer of the present invention located on the second side of the insulator, and a drain electrode and a source electrode located on the polymer layer.

The OFET device can be a top gate device or a bottom gate device.

Suitable structures and manufacturing methods of an OFET device are known to the person skilled in the art and are described in the literature, for example in WO03/052841.

The gate insulator layer may comprise for example a fluoropolymer, like e.g. the commercially available Cytop 809M®, or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont), or Fluoropel® (from Cytonix) or the perfluorosolvent FC 43® (Acros, No. 12377).

The semiconducting layer comprising a polymer of the present invention may additionally comprise at least another material. The other material can be, but is not restricted to another polymer of the present invention, a semi-conducting polymer, a polymeric binder, organic small molecules different from a polymer of the present invention, carbon nanotubes, a fullerene derivative, inorganic particles (quantum dots, quantum rods, quantum tripods, $TiO_2$, ZnO etc.), conductive particles (Au, Ag etc.), and insulator materials like the ones described for the gate dielectric (PET, PS etc.).

As stated above, the semiconductive layer can also be composed of a mixture of one or more polymers of the present invention and a polymeric binder. The ratio of the polymers of the present invention to the polymeric binder can vary from 5 to 95 percent. Preferably, the polymeric binder is a semicristalline polymer such as polystyrene (PS), high-density polyethylene (HDPE), polypropylene (PP) and polymethylmethacrylate (PMMA). With this technique, a degradation of the electrical performance can be avoided (cf. WO2008/001123A1).

The polymers of the present invention are advantageously used in organic photovoltaic (PV) devices (solar cells). Accordingly, the invention provides PV devices comprising a polymer according to the present invention. A device of this construction will also have rectifying properties so may also be termed a photodiode. Photoresponsive devices have application as solar cells which generate electricity from light and as photodetectors which measure or detect light.

The PV device comprise in this order:
  (a) a cathode (electrode),
  (b) optionally a transition layer, such as an alkali halogenide, especially lithium fluoride,
  (c) a photoactive layer,
  (d) optionally a smoothing layer,
  (e) an anode (electrode),
  (f) a substrate.

The photoactive layer comprises the polymers of the present invention. Preferably, the photoactive layer is made of a conjugated polymer of the present invention, as an electron donor and an acceptor material, like a fullerene, particularly a functionalized fullerene PCBM, as an electron acceptor. As stated above, the photoactive layer may also contain a polymeric binder. The ratio of the polymers of formula I to the polymeric binder can vary from 5 to 95 percent. Preferably, the polymeric binder is a semicristalline polymer such as polystyrene (PS), high-density polyethylene (HDPE), polypropylene (PP) and polymethylmethacrylate (PMMA).

For heterojunction solar cells the active layer comprises preferably a mixture of a polymer of the present invention and a fullerene, such as, for example, [60]PCBM (=6,6-phenyl-$C_{61}$-butyric acid methyl ester), or [70]PCBM, in a weight ratio of 1:1 to 1:3. The fullerenes useful in this invention may have a broad range of sizes (number of carbon atoms per molecule). The term fullerene as used herein includes various cage-like molecules of pure carbon, including Buckminsterfullerene ($C_{60}$) and the related "spherical" fullerenes as well as carbon nanotubes. Fullerenes may be selected from those known in the art ranging from, for example, $C_{20}$-$C_{1000}$. Preferably, the fullerene is selected from the range of $C_{60}$ to $C_{96}$. Most preferably the fullerene is $C_{60}$ or $C_{70}$, such as [60]PCBM, or [70]PCBM. It is also permissible to utilize chemically modified fullerenes, provided that the modified fullerene retains acceptor-type and electron mobility characteristics. The acceptor material can also be a material selected from the group consisting of any semi-conducting polymer, such as, for example, a polymer of the present invention, provided that the polymers retain acceptor-type and electron mobility characteristics, organic small molecules, carbon nanotubes, inorganic particles (quantum dots, quantum rods, quantum tripods, $TiO_2$, ZnO etc.).

The photoactive layer is made of a polymer of the present invention as an electron donor and a fullerene, particularly functionalized fullerene PCBM, as an electron acceptor. These two components are mixed with a solvent and applied as a solution onto the smoothing layer by, for example, the spin-coating method, the drop casting method, the Langmuir-Blodgett ("LB") method, the ink jet printing method and the dripping method. A squeegee or printing method could also be used to coat larger surfaces with such a photoactive layer. Instead of toluene, which is typical, a dispersion agent such as chlorobenzene is preferably used as a solvent. Among these methods, the vacuum deposition method, the spin-coating method, the ink jet printing method and the casting method are particularly preferred in view of ease of operation and cost.

In the case of forming the layer by using the spin-coating method, the casting method and ink jet printing method, the coating can be carried out using a solution and/or dispersion prepared by dissolving, or dispersing the composition in a concentration of from 0.01 to 90% by weight in an appropriate organic solvent such as benzene, toluene, xylene, tetrahydrofurane, methyltetrahydrofurane, N,N-dimethylformamide, acetone, acetonitrile, anisole, dichloromethane, dimethylsulfoxide, chlorobenzene, 1,2-dichlorobenzene and mixtures thereof.

The photovoltaic (PV) device can also consist of multiple junction solar cells that are processed on top of each other in order to absorb more of the solar spectrum. Such structures are, for example, described in App. Phys. Let. 90, 143512 (2007), Adv. Funct. Mater. 16, 1897-1903 (2006) and WO2004/112161.

A so called 'tandem solar cell' comprise in this order:
(a) a cathode (electrode),
(b) optionally a transition layer, such as an alkali halogenide, especially lithium fluoride,
(c) a photoactive layer,
(d) optionally a smoothing layer,
(e) a middle electrode (such as Au, Al, ZnO, $TiO_2$ etc.)
(f) optionally an extra electrode to match the energy level,
(g) optionally a transition layer, such as an alkali halogenide, especially lithium fluoride,
(h) a photoactive layer,
(i) optionally a smoothing layer,
(j) an anode (electrode),
(k) a substrate. The polymer of the present invention is comprised by one of the photoactive layers.

The PV device can also be processed on a fiber as described, for example, in US20070079867 and US 20060013549.

Due to their excellent self-organising properties the materials or films comprising the polymers of the present invention can also be used alone or together with other materials in or as alignment layers in LCD or OLED devices, as described for example in US2003/0021913.

The following examples are included for illustrative purposes only and do not limit the scope of the claims. Unless otherwise stated, all parts and percentages are by weight. Weight-average molecular weight (Mw) and polydispersity (Mw/Mn=PD) are determined by High Temperature Gel Permeation Chromatography (HT-GPC) [Apparatus: GPC PL 220 from Agilent Technologies (Santa Clara, Calif., USA) yielding the responses from refractive index (RI), Chromatographic conditions: Column: 3 "PLgel Mixed B" columns from Agilent Technologies (Santa Clara, Calif., USA); with an average particle size of 10 μm (dimensions 300×7.5 mm I.D.) Mobile phase: 1,2,4-trichlorobenzene (for GPC, AppliChem, Darmstadt, Germany) stabilised by butylhydroxytoluene (BHT, 1 g/l), Chromatographic temperature: 150° C.; Mobile phase flow: 1 ml/min; Solute concentration: about 1 mg/ml; Injection volume: 200 μl; Detection: RI, Procedure of molecular weight calibration: Relative calibration is done by use of a EasiVial calibration kit from Agilent Technologies (Santa Clara, Calif., USA) containing 12 narrow polystyrene calibration standards spanning the molecular weight range from 6,035,000 Da-162 Da, i.e., PS 6,035,000, PS 3,053,000, PS 915,000, PS 483,000, PS 184,900, PS 60,450, PS 19,720, PS 8,450, PS 3,370, PS 1,260, PS 580, PS 162 Da. A polynomic calibration is used to calculate the molecular weight.

All polymer structures given in the examples below are idealized representations of the polymer products obtained via the polymerization procedures described. If more than two components are copolymerized with each other sequences in the polymers can be either alternating or random depending on the polymerisation conditions.

EXAMPLES

Example 1

Synthesis of Polymer P-1

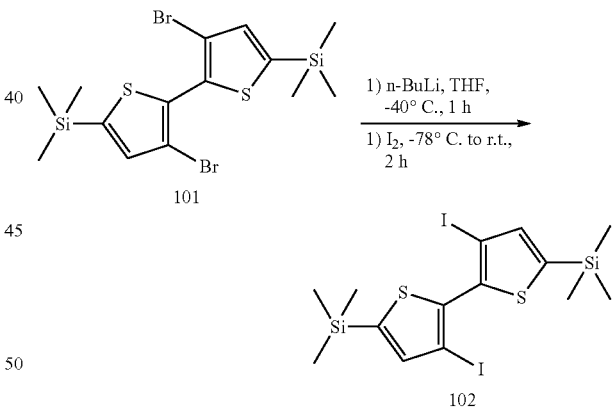

a) In a 250 mL flask previously flushed with nitrogen and equipped with a condenser and a nitrogen bubbler, is introduced [4-bromo-5-(3-bromo-5-trimethylsilyl-2-thienyl)-2-thienyl]-trimethyl-silane 101 (10.0 g, 21.3 mmol) and tetrahydrofuran (THF, 120 mL). The solution is cooled to −78° C. and n-Butyllithium (2.7 M in heptane, 17.4 mL, 47.0 mmol) is added dropwise. The mixture is stirred 1 h at −78° C. and then 30 minutes at 0° C. After that time the solution is cooled to −78° C. again and iodine (11.92 g, 47.0 mmol) is added in a single portion. The mixture is stirred 30 minutes at −78° C. and then left to warm to room temperature over 2 h. After that time a saturated aqueous solution of sodium thiosulphate (100 ml) is added and the product is extracted with tert-butyl-methyl-ether (TBME) and dichloromethane. The organic layers are then dried over sodium sulphate. The solvent is then evaporated on rotary evaporator. The product can then be recrystallized from ethanol: The crude brown solid is dissolved in hot ethanol and then cooled to −78° C., where a beige solid precipitates. The solid is filtered, washed with cold ethanol and dried at 70° C. under reduced pressure for 4 h. This affords the desired compound as a beige solid (9.2 g, 77% yield).

NMR: $^1$H (400.1 MHz, CDCl$_3$), δ=7.23 (2H, s), 0.34 (18H, s); $^{13}$C (100.1 MHz, CDCl$_3$), δ=145.0 (2C), 141.8 (2C), 139.9 (2C), 85.7 (2C), −0.3 (6C).

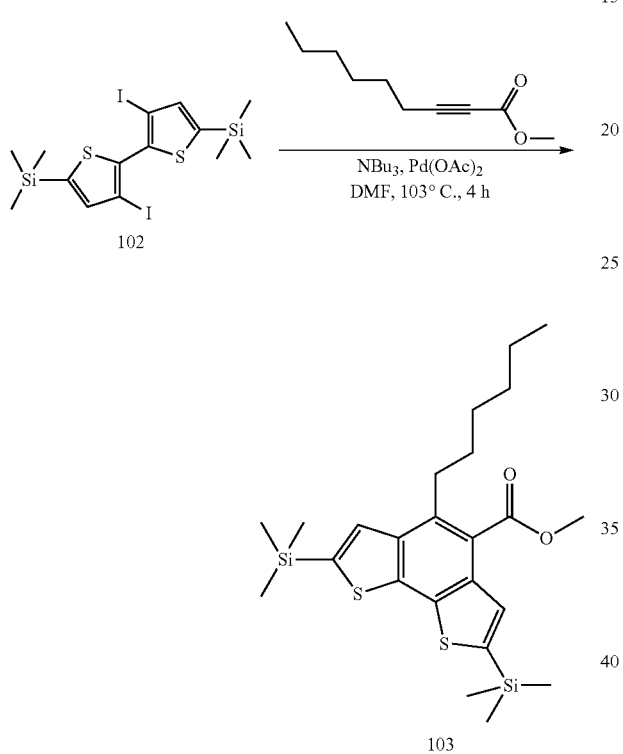

b) In a 1 liter flask is introduced compound 102 (51.18 g, 91.00 mmol). Dimethyl formamide (450 mL) is added under argon and the solution is degassed with argon. After, methyl-2-nonynoate (33.46 mL, 182.0 mmol) is added under argon at room temperature, followed by tributylamine (45.53 mL, 191.1 mmol) and Pd(OAc)$_2$ (2.043 g, 9.10 mmol). The reaction mixture is then heated to 130° C. for 4 h. After that time the solution was cooled to room temperature and concentrated on rotary evaporator. Water (500 mL), and tert-butyl-methyl ether (TBME, 500 mL) are added. The phases are separated and the water phase is extracted with TBME (300 mL). The combined organic phases are washed with water (500 mL) and brine (400 mL) and dried over sodium sulphate, filtered and the solvent was evaporated on rotary evaporator to give a dark brown oil. The crude oil is purified by flash chromatography (Silica gel, toluene/hexane 1:2) to afford the desired product 103 (orange oil, 15.81 g, 24% yield).

NMR: $^1$H (400.1 MHz, CDCl$_3$), δ=7.62 (1H, s), 7.59 (1H, s), 4.05 (3H, s), 3.14 (2H, t, J=8.0 Hz), 1.74 (2H, quint., J=8.0 Hz), 1.49-1.44 (2H, m), 1.39-1.34 (4H, m), 0.92 (3H, t, J=7.0 Hz), 0.43 (9H, s), 0.41 (9H, s).

c) In a 50 mL round bottom flask, equipped with a condenser is introduced compound 103 (2.38 g, 5.00 mmol). The flask is flushed with argon and dry and degassed tetrahydrofuran (THF, 14 mL) is added. Tetrabutylammonium fluoride trihydrate (TBAF, 3.47 g, 11.0 mmmol) is then added slowly added at room temperature as a solution in THF (11 mL). The resulting solution is then stirred overnight at room temperature. After that time tert-butyl-methyl-ether (TBME, 25 mL) is added and the organic phase is washed with water (2×50 mL) and brine (40 mL). The aqueous phases are then extracted with TBME (30 mL). The combined organic fractions are then dried over sodium sulphate, filtered and the solvent is evaporated on rotary evaporator to obtain a brown oil. The crude oil is then purified by flash column chromatography (Silica gel, toluene/cyclohexane 1:2, then 1:1) to obtain compound 104 (yellow oil, 1.455 g, 87% yield).

NMR: $^1$H (400.1 MHz, CDCl$_3$), δ=7.54 (1H, d, J=5.5 Hz), 7.53 (1H, d, J=5.5 Hz), 7.44 (1H, d, J=5.5 Hz), 7.42 (1H, d, J=5.5 Hz), 4.04 (3H, s), 3.13 (2H, t, J=8.0 Hz), 1.78-1.70 (2H, m), 1.49-1.42 (2H, m), 1.37-1.32 (4H, m), 0.91 (3H, t, J=7.0 Hz); $^{13}$C (100.1 MHz, CDCl$_3$), δ=169.5, 136.7, 135.6, 135.0, 134.7, 132.0, 124.7, 124.6, 124.4, 123.8, 123.7, 52.1, 31.9, 31.6, 31.6 29.6, 22.6, 14.0. GC/MS: (CI pos.): 333.14 (MH$^+$).

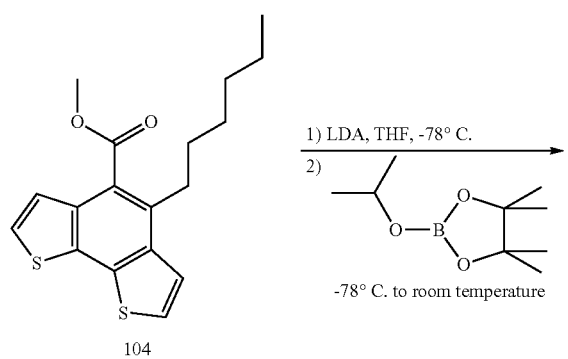

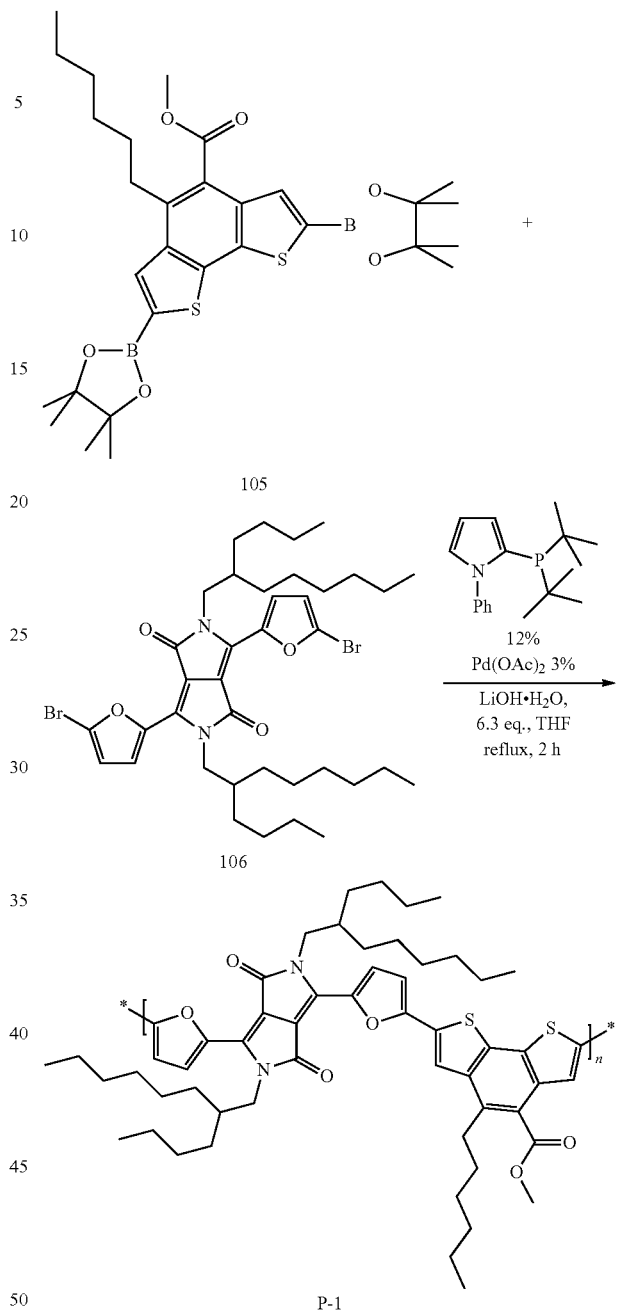

d) In a 3-neck flask equipped with a condenser and an addition funnel are introduced, under nitrogen, compound 104 (2.493 g, 7.50 mmol) and tetrahydrofuran (THF, 25 mL) followed by isopropoxypinacolborane (3.070 g, 16.50 mmol). The resulting solution is then cooled to −78° C. and a previously prepared lithium diisopropylamide solution (LDA, 15.37 mmol in 15 mL THF) is added dropwise. The reaction mixture is left to stir 1 h at −78° C. and is then allowed to warm to room temperature and stir for 3 additional hours at room temperature. After that time the reaction mixture is poured in 125 mL of HCl 2N and extracted with tert-butyl-methyl ether (TBME, 2×100 mL). The combined organic layers are washed with 100 mL water and 100 mL brine, then dried over sodium sulphate, filtered and the sokvent is evaporated on rotary evaporator to obtain compound 105 (beige powder, 4.25 g, 96% yield).

NMR: $^1$H (400.1 MHz, CDCl$_3$), δ=8.05 (1H, s), 8.00 (1H, s), 4.03 (3H, s), 3.12 (2H, t, J=8.0 Hz), 1.74-1.67 (2H, m), 1.40 (12H, s), 1.38 (12H, s), 1.45-1.20 (6H, m), 0.90 (3H, t, J=7.0 Hz);

e) The synthesis of 1,4-bis(5-bromo-2-furyl)-2,5-bis(2-butyloctyl)pyrrolo[3,4-c]pyrrole-3,6-dione 106 is, for example, described in patent application WO2011/144566.

In a 200 mL flask equipped with a condenser, a mechanical stirrer, an argon inlet and a thermometer is introduced compound 105 (600 mg, 1.03 mmol) and 1,4-bis(5-bromo-2-furyl)-2,5-bis(2-butyloctyl)pyrrolo[3,4-c]pyrrole-3,6-dione 106 (746 mg, 0.98 mmol). The flask is flushed with argon and dry THF (50 mL) is added by syringe. The resulting red solution is heated to reflux and a previously prepared solution of palladium(II) acetate (6.59 mg, 0.029 mmol) and 2-(di-tert-butylphosphino)-1-phenylpyrrole (33.7 mg, 0.117 mmol) in 5 mL THF is added at 50° C. The resulting mixture is stirred for 5 minutes at reflux temperature. After that time finely crushed lithium hydroxide monohydrate (258 mg, 6.16 mmol) is added in a single portion at 60° C. and is stirred at reflux temperature for 2 hours. After that time, the heating is stopped and water (75 mL) is added. The polymer is filtered, and washed with water.

The filtered solid is then put in a flask containing 70 mL chloroform and 75 mL of a 3% sodium cyanide aqueous solution and is heated under vigorous stirring at 55° C. overnight. The phases are separated, and the organic phase is washed with water (3×80 mL), and two thirds of the chloroform is then evaporated. Ethanol (150 mL) is added to precipitate the product, which is filtered on a Büchner funnel. The dried solid is then purified by soxhlet extraction, first with cyclohexane (160 mL, 19 h). The fraction soluble in cyclohexane is discarded and the remaining solid is then subjected to soxhlet extraction with tetrahydrofuran (160 mL, 3 h). The solution is concentrated, the product is precipitated in ethanol, filtered and dried under reduced pressure to afford the polymer P-1 (700 mg, yield 77%).

High temperature GPC: $M_w$=41500, PD 2.20.

Example 2

Synthesis of Polymer P-2

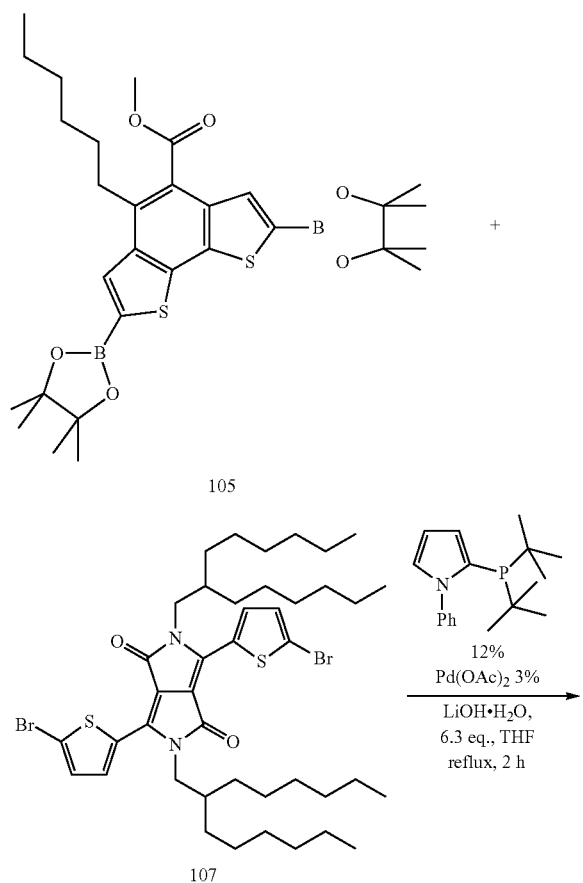

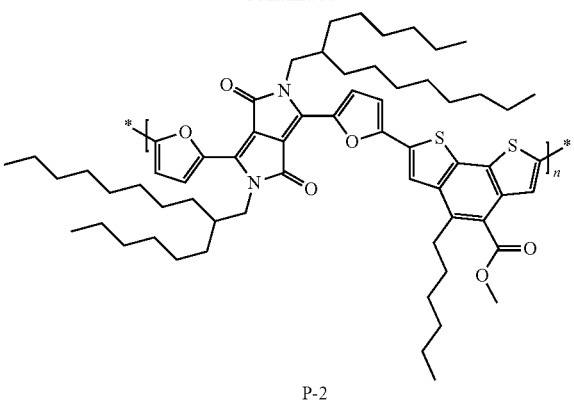

P-2

The synthesis of 3,6-bis(5-bromothiophen-2-yl)-2,5-bis (2-hexyldecyl)pyrrolo[3,4-c]pyrrole-1,4(2H,5H)-dione 107 is, for example, described in WO2008/000664 and Y. Geerts; Tetrahedron 66 (2010) 1837-1845. In a 200 mL flask equipped with a condenser, a mechanical stirrer, an argon inlet and a thermometer is introduced compound 105 (614 mg, 1.05 mmol) and 3,6-bis(5-bromothiophen-2-yl)-2,5-bis (2-hexyldecyl)pyrrolo[3,4-c]pyrrole-1,4(2H,5H)-dione 107 (907 mg, 1.00 mmol). The flask is flushed with argon and dry THF (50 mL) is added by syringe. The resulting red solution is heated to reflux and a previously prepared solution of palladium(II) acetate (6.7 mg, 0.030 mmol) and 2-(di-tert-butylphosphino)-1-phenylpyrrole (34.5 mg, 0.120 mmol) in 5 mL THF is added at 50° C. The resulting mixture is stirred for 5 minutes at reflux temperature. After that time finely crushed lithium hydroxide monohydrate (264 mg, 6.30 mmol) is added in a single portion at 60° C. and is stirred at reflux temperature for 2 hours. After that time, the heating is stopped and water (75 mL) is added. The polymer is filtered, and washed with water.

The filtered solid is then put in a flask containing 70 mL chloroform and 75 mL of a 3% sodium cyanide aqueous solution and is heated under vigorous stirring at 55° C. overnight. The organic phase is washed with water (3×80 mL), and two thirds of the chloroform is then evaporated. Ethanol (150 mL) is added to precipitate the product, which is filtered on a Büchner funnel. The dried solid is then purified by soxhlet extraction, first with cyclohexane (160 mL, 2 h), and then with tetrahydrofuran (160 mL, 4 h). The fractions soluble in cyclohexane and tetrahydrofuran are discarded and the remaining solid is then subjected to soxhlet extraction with chloroform (160 mL, 3 h). The solution is concentrated, the product is precipitated in ethanol, filtered and dried under reduced pressure to afford the polymer P-2 (1000 mg, yield 92%).

High temperature GPC: $M_w$=49200, PD 2.12.

Example 3

Synthesis of Polymer P-3

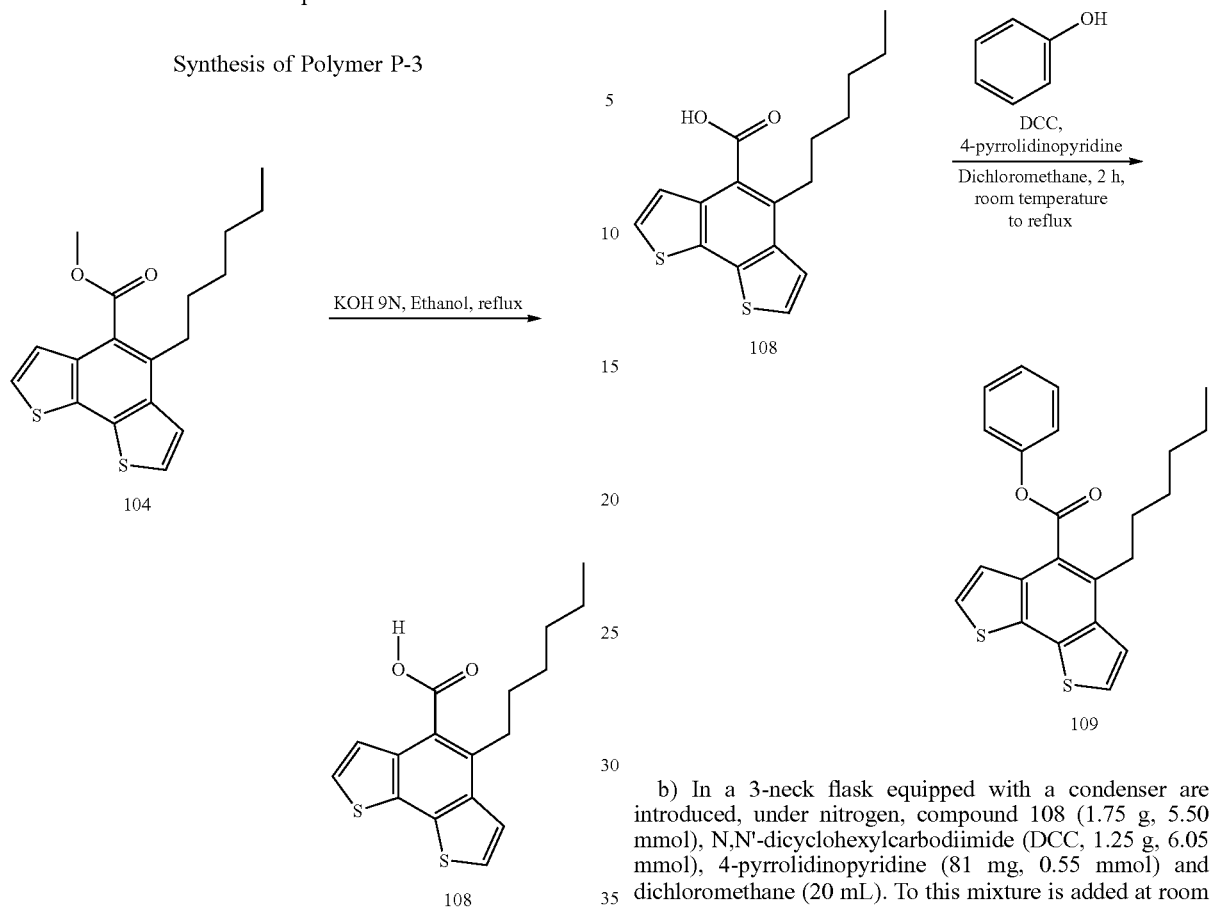

a) In a flask, equipped with a condenser, is introduced under argon compound 104 (4.99 g, 15.0 mmol), ethanol (40 mL) and 9N KOH in water (8.33 mL, 75.0 mmol). The resulting mixture is stirred 1 h at room temperature and 2 h at reflux. As the conversion is incomplete 8.33 mL of 9N KOH in water and 50 mL ethanol are added again, and the resulting solution is heated at reflux for 5 h. After that time the solvent is removed on rotary evaporator, tert-butyl-methyl ether (100 mL) is added followed by 100 mL of a 2N HCl (aq.) solution. Phases are separated and the aqueous phase is extracted with 75 mL of tert-butyl-methyl ether. The combined organic phases are then washed with water (100 mL) and brine (100 mL), then dried over sodium sulphate, filtered and the solvent is evaporated on rotary evaporator. The crude is then recrystallized from chloroform (22 mL), and the obtained crystals are then washed with cold chloroform and dried under vacuum to obtain the pure product 108 (beige crystals, 4.098 g, yield: 85%).

NMR: $^1$H (400.1 MHz, CDCl$_3$), δ=7.86 (1H, d, J=5.5 Hz), 7.60 (1H, d, J=5.5 Hz), 7.48 (2H, d, J=5.2 Hz), 3.32 (2H, t, J=8.0 Hz), 1.85-1.77 (2H, m), 1.55-1.48 (2H, m), 1.42-1.33 (4H, m), 0.90 (3H, t, J=7.0 Hz); $^{13}$C (100.1 MHz, CDCl$_3$), δ=174.5, 136.9, 136.8, 136.6, 135.4, 132.3, 125.1, 124.9, 124.8, 124.0, 122.0, 32.1, 31.7, 31.6, 29.7, 22.6, 14.1.

b) In a 3-neck flask equipped with a condenser are introduced, under nitrogen, compound 108 (1.75 g, 5.50 mmol), N,N'-dicyclohexylcarbodiimide (DCC, 1.25 g, 6.05 mmol), 4-pyrrolidinopyridine (81 mg, 0.55 mmol) and dichloromethane (20 mL). To this mixture is added at room temperature phenol (569 mg, 6.05 mmol). After one hour at room temperature, the mixture is stirred at reflux for 1 h. The white suspension is then filtered over Hyflo, and washed with dichloromethane. The filtrate is concentrated on rotary evaporator to get 2.97 g of crude beige crystals. The crude is then purified by flash chromatography (gradient, Toluene/cyclohexane from 0:100 to 25:75) to obtain the pure product 109 (white crystals, 1.88 g, yield: 87%).

NMR: $^1$H (400.1 MHz, CDCl$_3$), δ=7.76 (1H, d, J=5.5 Hz), 7.59 (1H, d, J=5.5 Hz), 7.53-7.47 (4H, m), 7.36-7.32 (3H, m), 3.30 (2H, t, J=8.0 Hz), 1.86-1.79 (2H, m), 1.53-1.48 (2H, m), 1.36-1.31 (4H, m), 0.89 (3H, t, J=7.0 Hz); $^{13}$C (100.1 MHz, CDCl$_3$), δ=167.3, 150.8, 136.8, 136.1, 135.6, 135.1, 132.2, 129.6 (2C), 126.0, 125.0, 124.8, 124.4, 123.8, 122.7, 121.5 (2C), 32.1, 31.7, 31.6, 29.7, 22.5, 14.0.

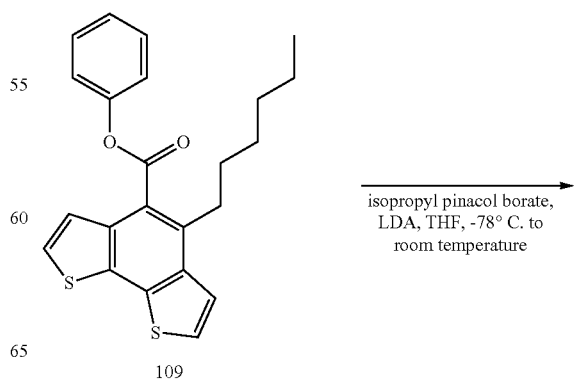

isopropyl pinacol borate, LDA, THF, -78° C. to room temperature

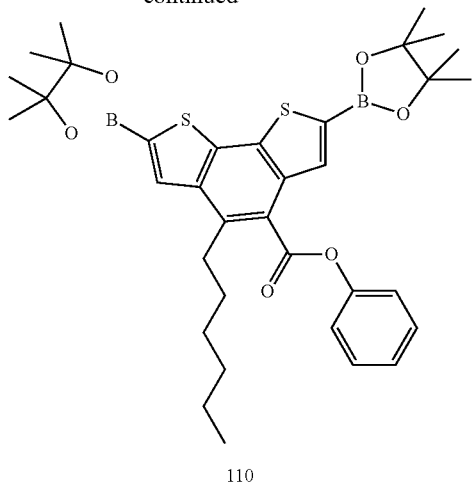

110 c) In a 3-neck flask equipped with a condenser and an addition funnel are introduced, under nitrogen, compound 109 (1.776 g, 4.50 mmol) and tetrahydrofuran (THF, 13 mL) followed by isopropoxypinacolborane (1.515 g, 8.14 mmol). The resulting solution is then cooled to −78° C. and a previously prepared lithium diisopropylamide solution (LDA, 1.73 mmol in 7 mL THF) is added dropwise. The reaction mixture is left to stir 1 h at −78° C. and is then allowed to warm to room temperature and stir for 1 additional hour at room temperature. After that time the reaction mixture is poured in 50 mL of HCl 2N and extracted with tert-butyl-methyl ether (TBME, 2×50 mL). The combined organic layers are washed with 50 mL water and 50 mL brine, then dried over sodium sulphate, filtered and the solvent is evaporated on rotary evaporator. The crude is then recrystallized from diisopropylether, and the obtained crystals are then washed with diisopropylether and dried under vacuum to obtain the pure product 110 (white crystals, 1.325 g, yield: 45%).

NMR: $^1$H (400.1 MHz, CDCl$_3$), δ=8.20 (1H, s), 8.10 (1H, s), 7.52-7.48 (2H, m), 7.37-7.30 (3H, m), 3.30 (2H, t, J=8.0 Hz), 1.83-1.77 (2H, m), 1.53-1.45 (2H, m), 1.42 (12H, s), 1.38 (12H, s), 1.34-1.27 (4H, m), 0.86 (3H, t, J=7.2 Hz).

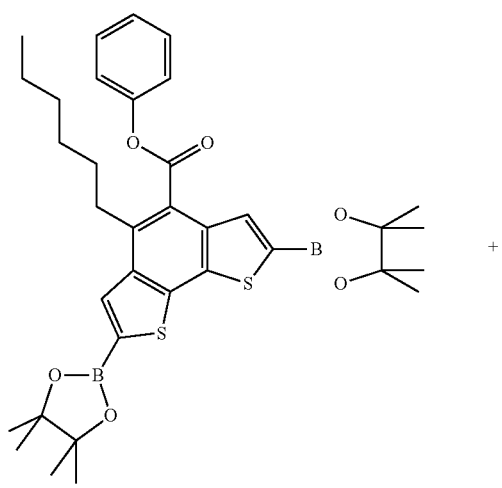

110

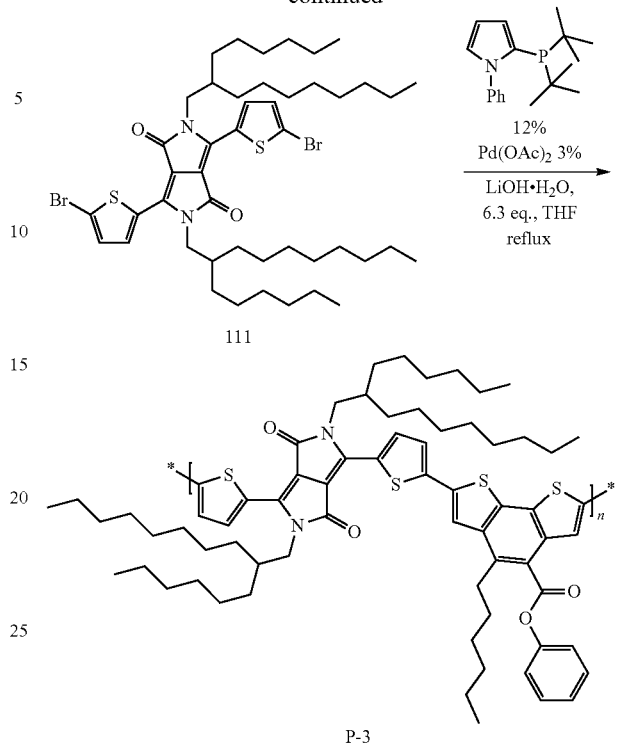

111

P-3

The synthesis of 3,6-bis(5-bromothiophen-2-yl)-2,5-bis(2-hexyldecyl)pyrrolo[3,4-c]pyrrole-1,4(2H,5H)-dione is, for example, described in WO2008/000664 and Y. Geerts; Tetrahedron 66 (2010) 1837-1845. In a 200 mL flask equipped with a condenser, a mechanical stirrer, an argon inlet and a thermometer is introduced the bis-boronic ester 110 (557 mg, 0.861 mmol) and 3,6-bis(5-bromothiophen-2-yl)-2,5-bis(2-hexyldecyl)pyrrolo[3,4-c]pyrrole-1,4(2H,5H)-dione 111 (744 mg, 0.82 mmol). The flask is flushed with argon and dry THF (50 mL) is added by syringe. The resulting red solution is heated to reflux and a previously prepared solution of palladium(II) acetate (5.52 mg, 0.025 mmol) and 2-(di-tert-butylphosphino)-1-phenylpyrrole (28.3 mg, 0.098 mmol) in 5 mL THF is added at 50° C. The resulting mixture is stirred for 5 minutes at reflux temperature. After that time finely crushed lithium hydroxide monohydrate (218 mg, 5.17 mmol) is added in a single portion at 60° C. and is stirred at reflux temperature for 3 hours. After that time, the heating is stopped and water (75 mL) is added. The polymer is filtered, and washed with water.

The filtered solid is then put in a flask containing 70 mL chloroform and 75 mL of a 3% sodium cyanide aqueous solution and is heated under vigorous stirring at 55° C. overnight. The phases are separated and the organic phase is washed with water (3×80 mL), and two thirds of the chloroform is then evaporated. Ethanol (150 mL) is added to precipitate the product, which is filtered on a Büchner funnel. The dried solid is then purified by soxhlet extraction, first with cyclohexane (160 mL, 18 h) and with tetrahydrofuran (160 mL, 8 h). The fractions soluble in cyclohexane and tetrahydrofuran are discarded and the remaining solid is then subjected to soxhlet extraction with chloroform (160 mL, 3 h). The solution is concentrated, the product is precipitated in ethanol, filtered and dried under reduced pressure to afford the polymer P-3 (780 mg, yield 84%).

High temperature GPC: $M_w$=82800, PD 1.98.

Example 4

Synthesis of Polymer P-4

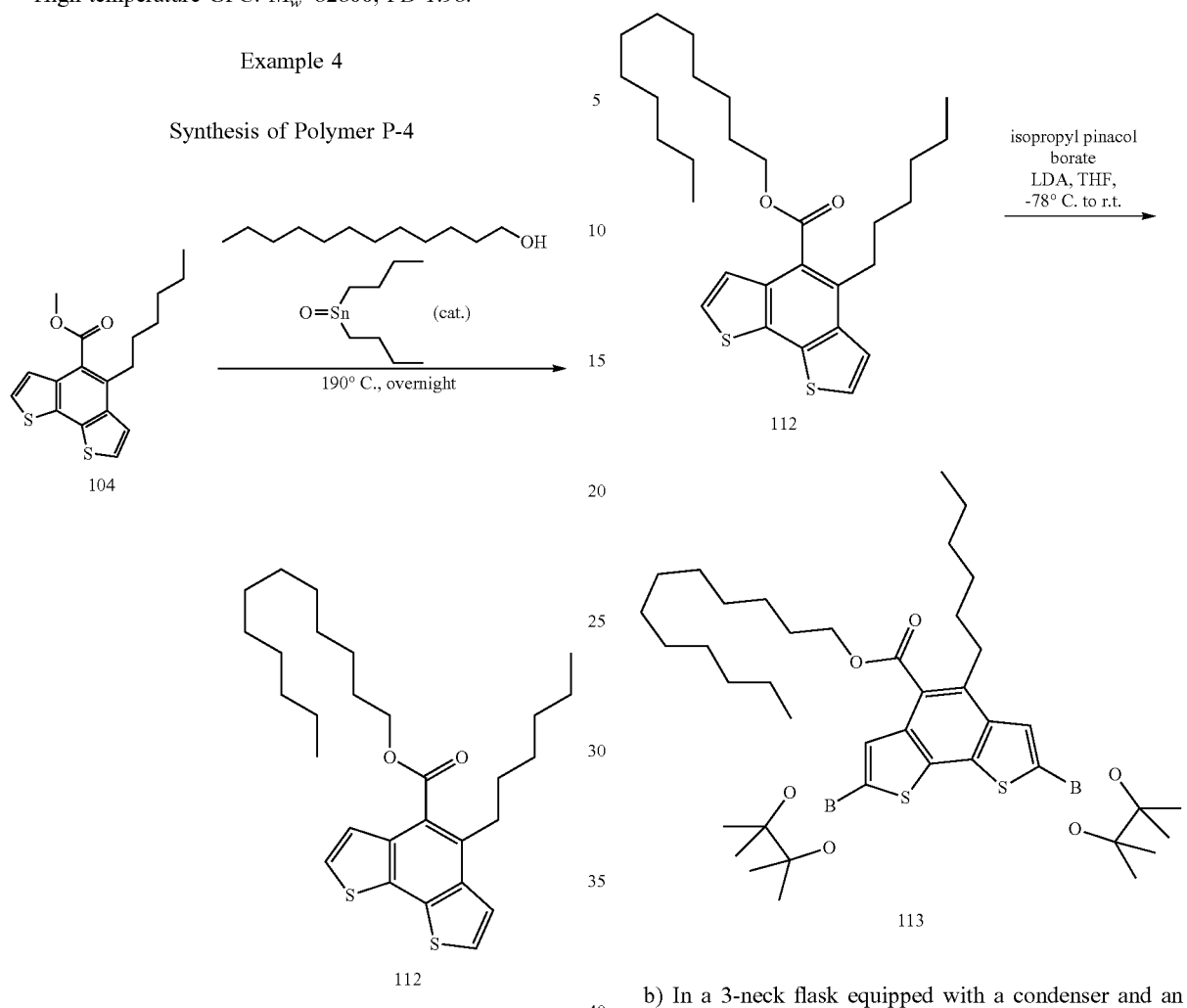

a) In a flask equipped with a condenser and an addition funnel are introduced compound 104 (1.33 g, 4.00 mmol) and 1-dodecanol (11.18 g, 60 mmol). The flask is flushed with argon and dibutyloxostannane (99.5 mg, 0.40 mmol) are added under argon at room temperature. The resulting solution is then heated to 190° C. under reduced pressure (200 mbar). After one hour an additional amount of 200 mg of dibutyloxostannane were added and the mixture stirred overnight at 190° C. under reduced pressure. After that time cyclohexane (15 mL) is added and the reaction mixture is directly purified by flash chromatography (eluent: toluene/cyclohexane 2:3) to get the pure product 112 (yellow oil, 1.606 g, yield: 82%).

NMR: $^1$H (400.1 MHz, CDCl$_3$), δ=7.54 (1H, d, J=5.5 Hz), 7.53 (1H, d, J=5.5 Hz), 7.45 (1H, d, J=5.5 Hz), 7.42 (1H, d, J=5.5 Hz), 4.45 (2H, t, J=7.0 Hz), 3.13 (2H, d, J=8.0 Hz), 1.82 (2H, quint., J=7.0 Hz), 1.76-1.70 (2H, m), 1.50-1.42 (4H, m), 1.38-1.23 (20H, m), 0.92 (6H, m); $^{13}$C (100.1 MHz, CDCl$_3$), δ=169.2, 136.7, 135.3, 135.0, 134.2, 131.9, 124.5, 124.5, 124.3, 124.2, 123.7, 65.5, 31.9, 31.8, 31.7 (2C), 29.8, 29.6 (4C), 29.5, 29.3, 29.2, 28.7, 26.1, 22.6, 14.1 (2C).

b) In a 3-neck flask equipped with a condenser and an addition funnel are introduced, under nitrogen, compound 112 (1.801 g, 3.70 mmol) and tetrahydrofuran (THF, 13 mL) followed by isopropoxypinacolborane (1.515 g, 8.14 mmol). The resulting solution is then cooled to −78° C. and a previously prepared lithium diisopropylamide solution (LDA, 7.58 mmol in 7 mL THF) is added dropwise. The reaction mixture is left to stir 1 h at −78° C. and is then allowed to warm to room temperature and stir for 3 additional hours at room temperature. After that time the reaction mixture is poured in 50 mL of HCl 2N and extracted with tert-butyl-methyl ether (TBME, 2×50 mL). The combined organic layers are washed with 50 mL water and 50 mL brine, then dried over sodium sulphate, filtered and the solvent is evaporated on rotary evaporator. The crude is then triturated in warm isopropanol, filtered, and the obtained crystals are then washed with isopropanol and dried under vacuum to obtain the pure product 113 (white crystals, 1.836 g, yield: 67%).

NMR: $^1$H (400.1 MHz, CDCl$_3$), δ=8.05 (1H, s), 8.01 (1H, s), 4.44 (2H, t, J=6.8 Hz), 3.12 (2H, d, J=8.0 Hz), 1.81 (2H, quint., J=6.8 Hz), 1.74-1.69 (2H, m), 1.48-1.21 (24H, m), 1.40 (12H, s), 1.37 (12H, s), 0.91-0.85 (6H, m).

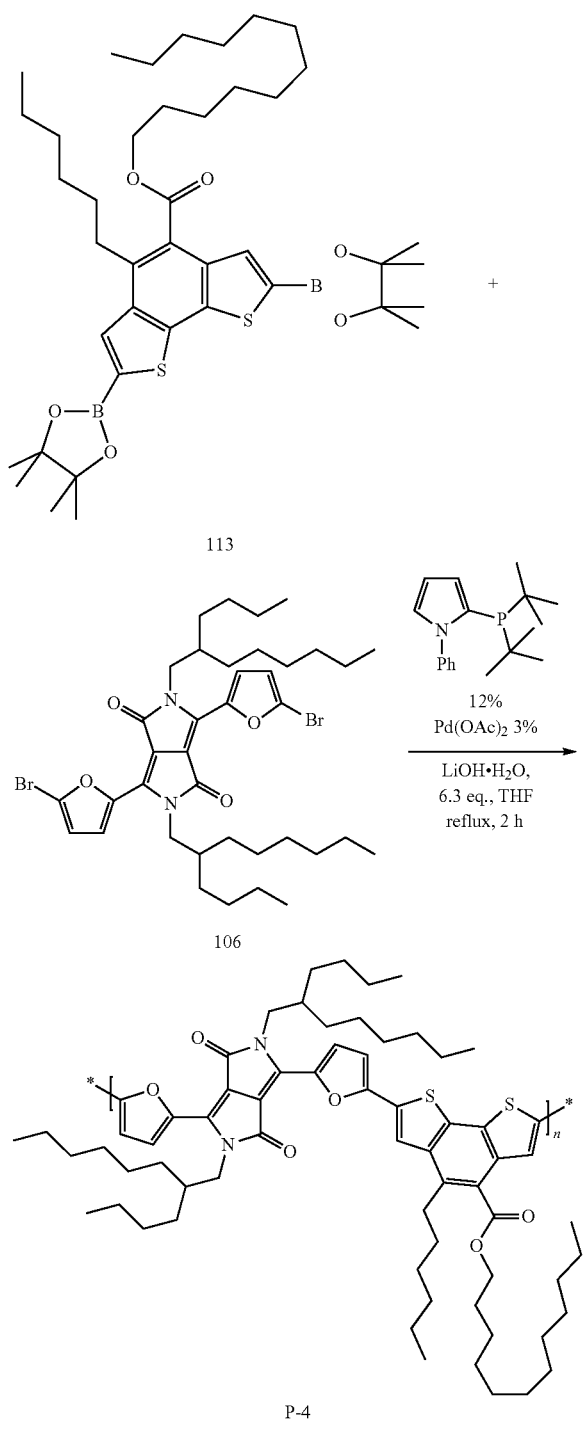

P-4

The synthesis of 1,4-bis(5-bromo-2-furyl)-2,5-bis(2-butyloctyl)pyrrolo[3,4-c]pyrrole-3,6-dione 106 is, for example, described in WO2011/144566.

c) In a 200 mL flask equipped with a condenser, a mechanical stirrer, an argon inlet and a thermometer is introduced the bis-boronic ester 113 (550 mg, 0.74 mmol) and 1,4-bis(5-bromo-2-furyl)-2,5-bis(2-butyloctyl)pyrrolo[3,4-c]pyrrole-3,6-dione 106 (541 mg, 0.71 mmol). The flask is flushed with argon and dry tetrahydrofuran (THF, 50 mL) is added by syringe. The resulting solution is heated to reflux and a previously prepared solution of palladium(II) acetate (4.78 mg, 0.021 mmol) and 2-(di-tert-butylphosphino)-1-phenylpyrrole (24.5 mg, 0.085 mmol) in 5 mL THF is added at 50° C. The resulting mixture is stirred for 5 minutes at reflux temperature. After that time finely crushed lithium hydroxide monohydrate (187 mg, 4.47 mmol) is added in a single portion at 55° C. and is stirred at reflux temperature for 2 hours. After that time, the heating is stopped and water (75 mL) is added. The polymer is filtered, and washed with water. The filtered solid is then put in a flask containing 70 mL chloroform and 75 mL of a 3% sodium cyanide aqueous solution and is heated under vigorous stirring at 55° C. overnight. The phases are separated and the organic phase is washed with water (3×80 mL), and two thirds of the chloroform is then evaporated. Ethanol (100 mL) is added to precipitate the product, which is filtered on a Büchner funnel. The dried solid is then purified by soxhlet extraction, first with cyclohexane (160 mL, 20 h). The fraction soluble in cyclohexane is discarded and the remaining solid is then subjected to soxhlet extraction with tetrahydrofuran (160 mL, 5 h). The solution is concentrated, the product is precipitated in ethanol, filtered and dried under reduced pressure to afford the polymer P-4 (524 mg, yield 70%).

High temperature GPC: $M_w$=61700, PD 1.88.

Example 5

Synthesis of Polymer P-5

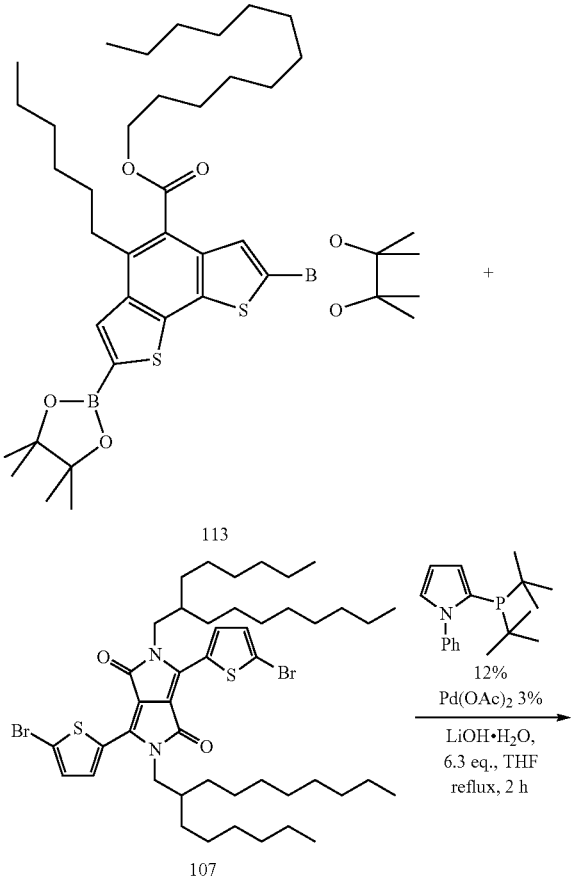

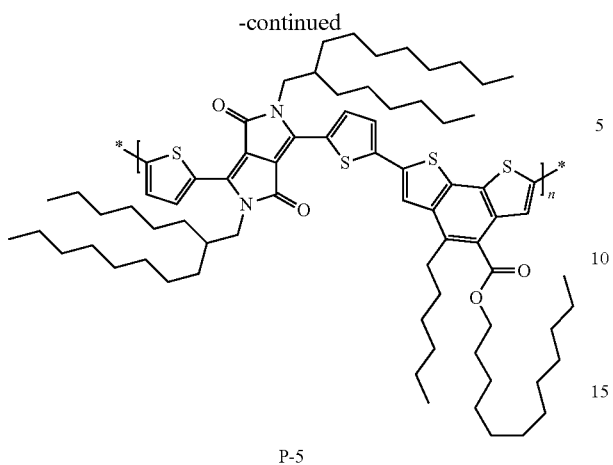

P-5

The synthesis of 3,6-bis(5-bromothiophen-2-yl)-2,5-bis (2-hexyldecyl)pyrrolo[3,4-c]pyrrole-1,4(2H,5H)-dione is, for example, described in WO2008/000664 and Y. Geerts; Tetrahedron 66 (2010) 1837-1845. In a 200 mL flask equipped with a condenser, a mechanical stirrer, an argon inlet and a thermometer is introduced the bis-boronic ester 113 (665 mg, 0.90 mmol) and 3,6-bis(5-bromothiophen-2-yl)-2,5-bis(2-hexyldecyl)pyrrolo[3,4-c]pyrrole-1,4(2H,5H)-dione 107 (777 mg, 0.86 mmol). The flask is flushed with argon and dry tetrahydrofuran (THF, 55 mL) is added by syringe. The resulting red solution is heated to reflux and a previously prepared solution of palladium(II) acetate (5.77 mg, 0.026 mmol) and 2-(di-tert-butylphosphino)-1-phenylpyrrole (29.6 mg, 0.103 mmol) in 5 mL THF is added at 50° C. The resulting mixture is stirred for 5 minutes at reflux temperature. After that time finely crushed lithium hydroxide monohydrate (227 mg, 5.40 mmol) is added in a single portion at 55° C. and is stirred at reflux temperature for 2 hours. After that time, the heating is stopped and water (75 mL) is added. The polymer is filtered, and washed with water. The filtered solid is then put in a flask containing 50 mL chloroform and 75 mL of a 2.5% sodium cyanide aqueous solution and is heated under vigorous stirring at 55° C. for 3 h. The organic phase is separated, and the organic fraction is treated again with 75 mL of a 2.5% sodium cyanide aqueous solution at 55° C. for 2.5 h. The organic phase is then separated and washed 3 times with water. Two thirds of the chloroform is then evaporated. Ethanol (150 mL) is added to precipitate the product, which is filtered on a Büchner funnel and washed with ethanol. The dried solid is then purified by soxhlet extraction, first with acetone (160 mL, 1 h), cyclohexane (160 mL, 16 h) and with tetrahydrofuran (160 mL, 3 h). The fractions soluble in acetone, cyclohexane and tetrahydrofuran are discarded and the remaining solid is then subjected to soxhlet extraction with chloroform (160 mL, 2.5 h). The solution is concentrated, the product is precipitated in ethanol, filtered and dried under reduced pressure to afford the polymer P-5 (870 mg, yield 83%).

High temperature GPC: $M_w$=41000, PD 1.80.

Example 6

Synthesis of Polymer P-6

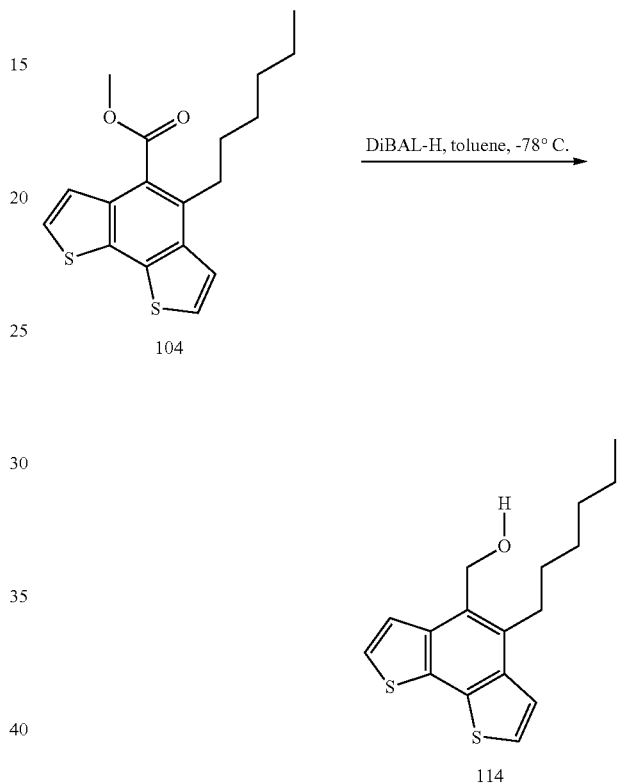

a) In a 500 mL flask equipped with a condenser is introduced, under nitrogen, methyl 5-hexylthieno[3,2-g]benzothiophene-4-carboxylate 104 (2.95 g, 8.88 mmol) and toluene (200 mL). Diisobutylaluminum hydride (DIBAL-H, 1.0 M in heptane, 17.2 mL, 17.2 mmol) is then slowly added at −78° C., and the resulting mixture is stirred 2 h at −78° C. The reaction mixture is then poured into 1M HCl (200 mL), and extracted with tert-butyl-methyl-ether (TBME, 100 mL) and dichloromethane (2×200 mL). The combined organic fractions are dried over sodium sulphate, filtered and the solvent was evaporated on rotary evaporator to obtain 2.45 g of a yellow oil which crystallized upon cooling. The crude is then purified by column chromatography (Silica gel, Hexane/EtOAc/dichloromethane 6:2:1) to obtain the product 114 (yellow solid, 2.05 g, yield: 77%).

NMR: $^1$H (400.1 MHz, CDCl$_3$), δ=7.65 (1H, d, J=5.5 Hz), 7.51 (1H, d, J=5.5 Hz), 7.45 (1H, d, J=5.5 Hz), 7.42 (1H, d, J=5.5 Hz), 5.12 (2H, s), 3.14 (2H, t, J=8.0 Hz), 1.72-1.64 (2H, m), 1.52-1.45 (2H, m), 1.37-1.31 (4H, m), 0.91 (3H, t, J=7.0 Hz); $^{13}$C (100.1 MHz, CDCl$_3$), δ=137.4, 137.3, 133.7, 133.5, 132.0, 128.6, 124.4, 124.0, 123.7, 123.3, 60.2, 32.3, 31.7, 30.4, 29.7, 22.7, 14.1.

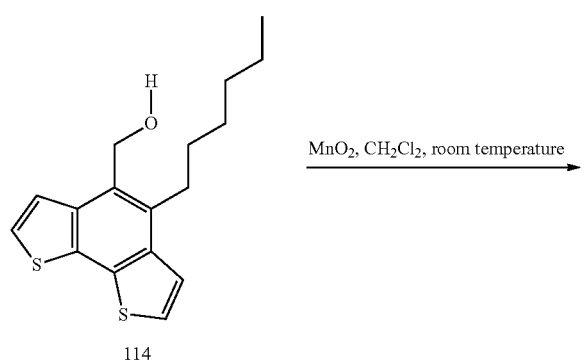

114

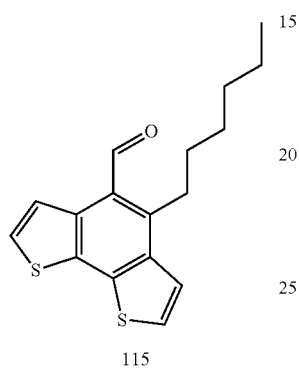

115 b) In a 500 mL flask equipped with a condenser is introduced compound 114 (2.05 g, 6.73 mmol) and dichloromethane (250 mL). MnO$_2$ (5.85 g, 67.3 mmol) is then slowly added at room temperature, and the resulting mixture is stirred 5 days at room temperature. Upon completion of the reaction, the product is filtered over a pad of silica to remove manganese salts. The filtrate is concentrated on rotary evaporator and the crude dark brown oil is purified by column chromatography (Silica gel, Hexanes/EtOAC 10:1, r.f. 0.6). This affords compound 115 as a yellow oil which slowly crystallizes (1.65 g, yield: 81%).

NMR: $^1$H (400.1 MHz, CDCl$_3$), δ=10.81 (1H, s), 8.48 (1H, d, J=5.5 Hz), 7.61 (1H, d, J=5.5 Hz), 7.55 (1H, d, J=5.3 Hz), 7.48 (1H, d, J=4.3 Hz), 3.45 (2H, t, J=8.0 Hz), 1.81-1.73 (2H, m), 1.53-1.44 (2H, m), 1.36-1.29 (4H, m), 0.90 (3H, t, J=7.0 Hz); $^{13}$C (100.1 MHz, CDCl$_3$), δ=191.4, 141.9, 139.2, 136.9, 135.1, 133.3, 126.6, 125.0, 124.9, 124.8, 123.6, 33.2, 31.6, 29.5, 29.2, 22.6, 14.1; GC/MS: (CI pos.): 303.18 (MH$^+$).

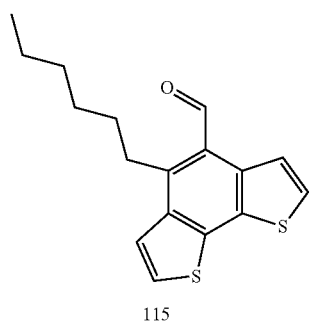

115

NH$_2$OH·HCl
Pyridine/EtOH
80° C., overnight

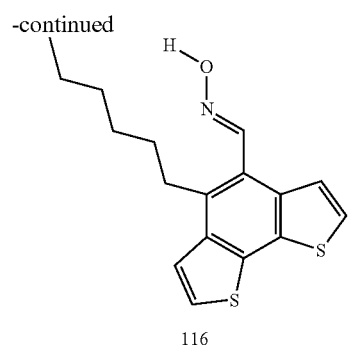

116 c) In a 500 mL flask equipped with a condenser is introduced under nitrogen compound 115 (1.65 g, 5.45 mmol) and hydroxylamine hydrochloride (569 mg, 8.18 mmol), pyridine (100 mL) and ethanol (100 mL). The yellow solution is then heated at 80° C. overnight. After that time, the mixture is cooled to room temperature, solvents are evaporated on rotary evaporator, chloroform (300 mL) is added, and the organic phase is washed with water (2×200 mL). The organic layer is then dried over sodium sulphate, and the solvent was evaporated on rotary evaporator. The crude is then purified by column chromatography (eluent: Hexane/EtoAc/CH$_2$Cl$_2$ 10:1:1, rf=0.5) to afford product 116 as a 20:1 mixture of isomers (white solid, 1.45 g, yield: 84%).

NMR: $^1$H (400.1 MHz, CDCl$_3$), δ=8.80 (1H, s), 8.09 (1H, d, J=5.5 Hz), 7.52 (1H, d, J=5.5 Hz), 7.43 (1H, d, J=5.5 Hz), 7.42 (1H, d, J=5.5 Hz), 3.13 (2H, t, J=8.0 Hz), 1.71-1.64 (2H, m), 1.50-1.42 (2H, m), 1.37-1.28 (4H, m), 0.90 (3H, m); $^{13}$C (100.1 MHz, CDCl$_3$), δ=149.5, 137.0, 135.4, 135.0, 132.6, 125.8, 124.6, 124.3, 123.6, 123.4, 120.9, 31.8, 31.7, 30.6, 29.5, 22.6, 14.1.

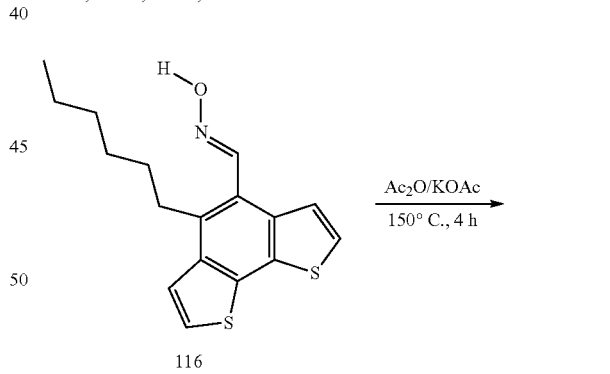

116

Ac$_2$O/KOAc
150° C., 4 h

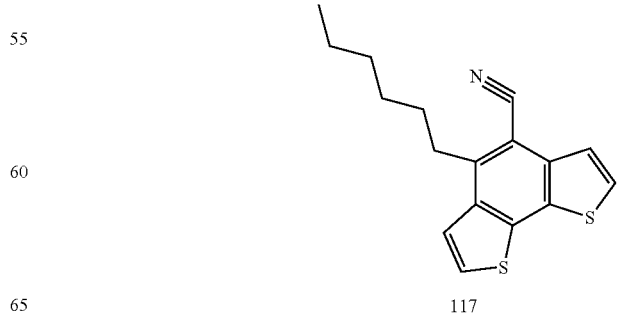

117 d) In a 500 mL round bottom flask equipped with a condenser is introduced, under nitrogen, compound 116 (1.30 g, 4.09 mmol), KOAc (100 mg) and acetic anhydride (100 mL). The yellow mixture is then heated at 150° C. for 4 h. After that time, the mixture is cooled to room temperature, and water (100 mL) is added followed by 5% NaOH solution. The product is then extracted with $Et_2O$ (3×200 mL). The combined organic layers are dried over sodium sulphate, and the solvent is evaporated on rotary evaporator to obtain a brown oil. The crude is then purified by column chromatography (Silica, hexanes/ethyl acetate 90:10, Rf=0.75). This affords product 117 (colorless to yellow oil, 1.15 g, yield: 94%).

NMR: $^1$H (400.1 MHz, $CDCl_3$), δ=7.63 (1H, d, J=5.5 Hz), 7.56 (1H, d, J=5.5 Hz), 7.54 (1H, d, J=5.5 Hz), 7.51 (1H, d, J=5.5 Hz), 3.27 (2H, t, J=7.8 Hz), 1.81-1.73 (2H, m), 1.51-1.43 (2H, m), 1.37-1.25 (4H, m), 0.90 (3H, m); $^{13}$C (100.1 MHz, $CDCl_3$), δ=141.3, 137.7, 137.1, 136.1, 132.0, 126.6, 125.7, 123.5, 123.4, 117.7, 103.3, 33.2, 31.6, 31.3, 29.3, 22.6, 14.1; GC/MS: (CI pos.): 300.19 ($MH^+$).

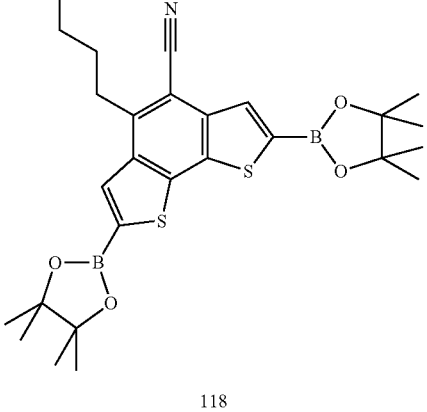

e) In a 100 mL flask equipped with a condenser is introduced, under nitrogen, compound 117 (1.1 g, 3.67 mmol as a solution in 20 mL tetrahydrofuran). Under nitrogen, more tetrahydrofuran (THF, 80 mL) is then added. The yellow solution is cooled to −78° C. and n-butyllithium solution (2.7 M in heptane, 3.4 mL, 9.19 mmol) is added dropwise. The resulting yellow mixture is stirred for 1 h 20 at −78° C. After that time isopropoxy pinacol borane (2.05 g, 11.0 mmol) is added at −78° C. The mixture turns to a clear yellow solution. After 20 minutes at −78° C., the reaction mixture is allowed to warm to room temperature and is stirred 2 hours at room temperature. Then, water is added at 0° C. and the product is extracted with tert-butyl-methyl-ether (TBME, 100 mL) and dichloromethane (2×100 mL). The combined organic fractions are dried over $Na_2SO_4$, filtered, concentrated on rotary evaporator. The crude yellow oil is recrystallized in acetonitrile and the powder is filtered and washed with cold acetonitrile to obtain product 118 (white powder, 1.81 g, yield: 89%).

NMR: $^1$H (400.1 MHz, $CDCl_3$), δ=8.16 (1H, s); 8.05 (1H, s), 3.28 (2H, t, J=7.8 Hz), 1.77 (2H, q, J=7.8 Hz), 1.55-1.25 (6H, m), 1.41 (12H, s), 1.39 (12H, s), 0.89 (3H, t, J=6.8 Hz).

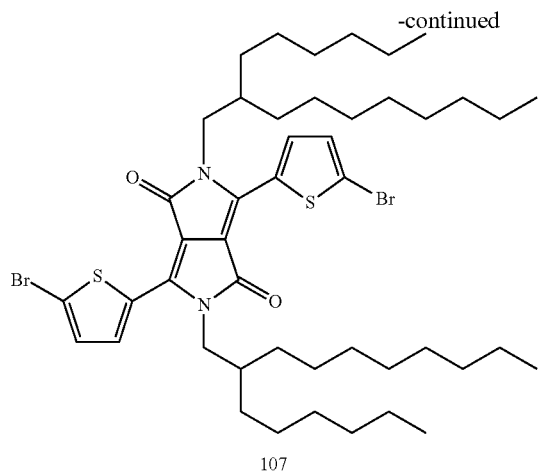
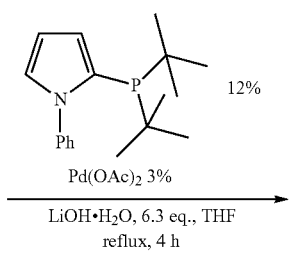

107

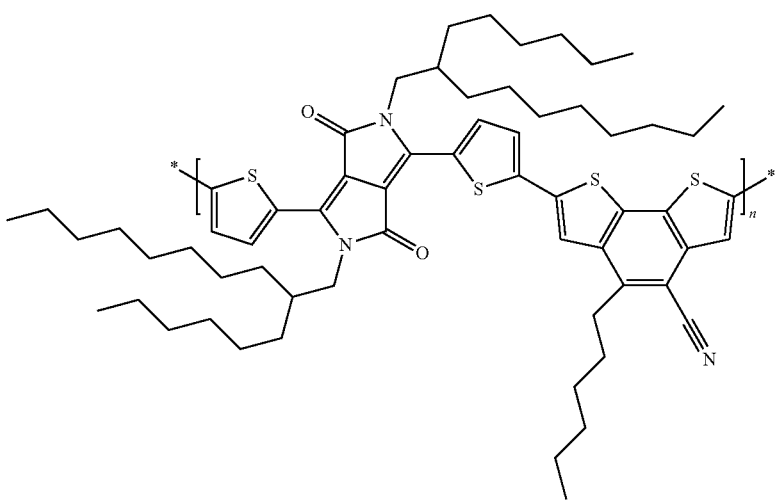

P-6 f) The synthesis of 3,6-bis(5-bromothiophen-2-yl)-2,5-bis (2-hexyldecyl)pyrrolo[3,4-c]pyrrole-1,4(2H,5H)-dione 107 is, for example, described in WO2008/000664 and Y. Geerts; Tetrahedron 66 (2010) 1837-1845. In a 250 mL flask equipped with a condenser, a mechanical stirrer, a nitrogen bubbler and a thermometer is introduced bis-boronic ester 118 (469 mg, 0.85 mmol) and 3,6-bis(5-bromothiophen-2-yl)-2,5-bis(2-hexyldecyl)pyrrolo[3,4-c]pyrrole-1,4(2H,5H)-dione 107 (739 mg, 0.81 mmol). The flask is flushed with nitrogen and dry THF (40 mL) is added by syringe. The resulting red solution is heated to 60° C. and a solution of palladium(II) acetate (5.5 mg, 0.024 mmol) and 2-(di-tert-butylphosphino)-1-phenylpyrrole (27.9 mg, 0.097 mmol) in 10 mL THF is added. The resulting mixture is stirred for 5 minutes at reflux temperature. After that time finely crushed lithium hydroxide monohydrate (214 mg, 5.10 mmol) is added in a single portion at 60° C. and is stirred at reflux temperature for 4 hours. The reaction mixture is poured into ethanol (300 mL) and the precipitate is filtered on a Büchner funnel. The solid is then washed with 200 mL ethanol and 200 mL deionised water. The filtered solid is then put in a flask containing 200 mL chloroform and 200 mL of a 2% sodium cyanide aqueous solution and is heated under vigorous stirring at 60° C. overnight. The phases are separated, and the organic phase is washed with 100 mL water, and two thirds of the chloroform is then evaporated. Ethanol is added to precipitate the product, which is filtered on a Büchner funnel, washed with 300 mL ethanol and dried in the oven. The treatment with sodium cyanide is then repeated a second time. The dried solid is then purified by soxhlet extraction, first with tetrahydrofuran (200 mL, 5 h). The fraction soluble in tetrahydrofuran is discarded and the remaining solid is then subjected to soxhlet extraction with chloroform (200 mL, 4 h). The green solution is concentrated, the product is precipitated in ethanol, filtered and dried under reduced pressure to afford the polymer P-6 (696 mg, yield 82%).

High temperature GPC: $M_w$=45600, $M_n$=19400, PD 2.34.

Example 7

Synthesis of Polymer P-7

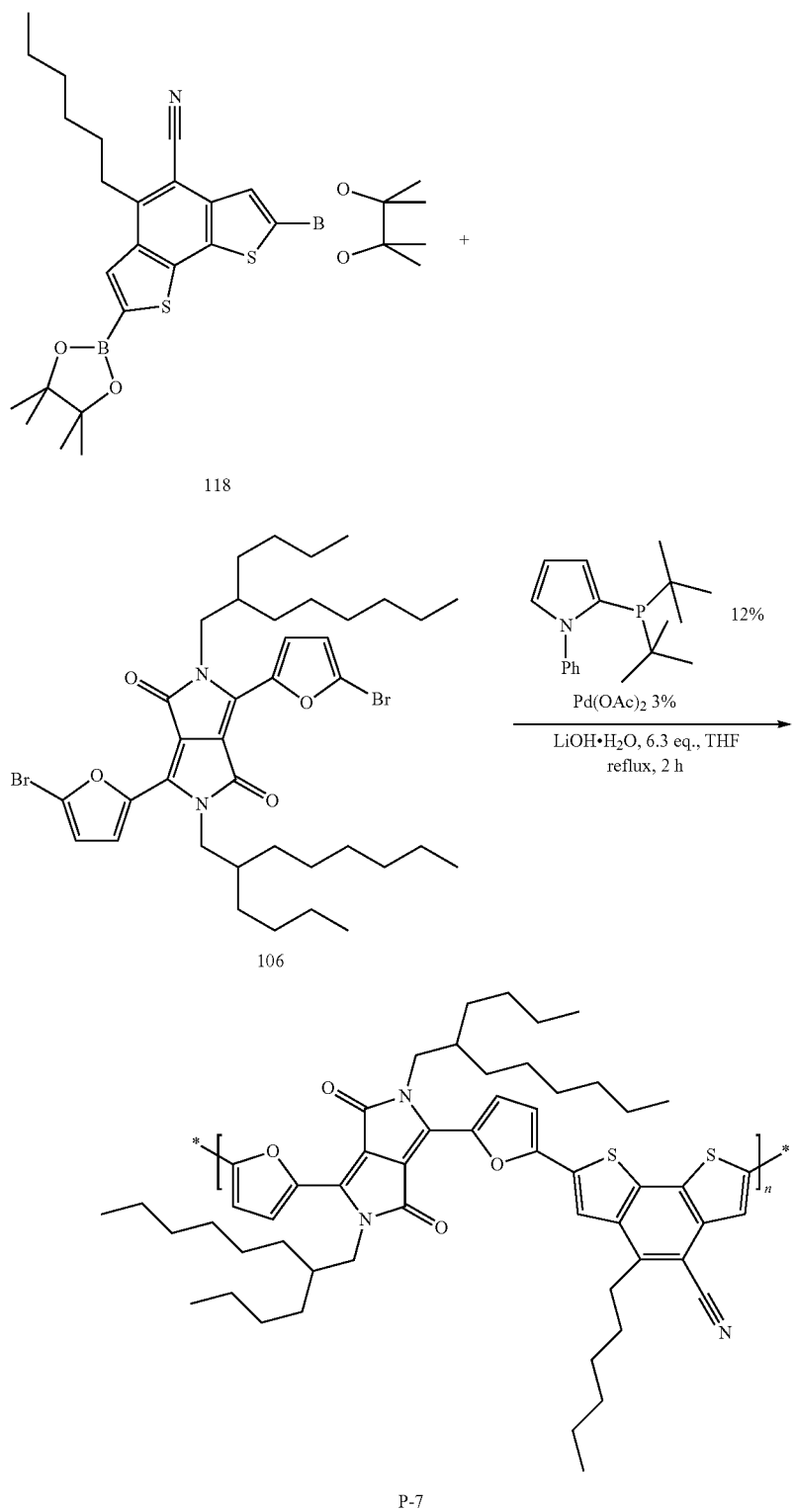

The synthesis of 1,4-bis(5-bromo-2-furyl)-2,5-bis(2-butyloctyl)pyrrolo[3,4-c]pyrrole-3,6-dione 106 is, for example, described in WO2011/144566.

In a 20 mL flask equipped with a condenser, a mechanical stirrer, an argon inlet and a thermometer is introduced the bis-boronic ester 118 (492 mg, 0.89 mmol) and 1,4-bis(5-bromo-2-furyl)-2,5-bis(2-butyloctyl)pyrrolo[3,4-c]pyrrole-3,6-dione 106 (648 mg, 0.85 mmol). The flask is flushed with argon and dry THF (45 mL) is added by syringe. The resulting solution is heated to reflux and a previously prepared solution of palladium(II) acetate (5.72 mg, 0.026 mmol) and 2-(di-tert-butylphosphino)-1-phenylpyrrole (29.3 mg, 0.102 mmol) in 5 mL THF is added at 50° C. The resulting mixture is stirred for 5 minutes at reflux temperature. After that time finely crushed lithium hydroxide monohydrate (225 mg, 5.36 mmol) is added in a single portion at 60° C. and is stirred at reflux temperature for 2 hours. After that time, the heating is stopped and water (75 mL) is added. The polymer is filtered, and washed with water. The filtered solid is then put in a flask containing 70 mL chloroform and 75 mL of a 3% sodium cyanide aqueous solution and is heated under vigorous stirring at 55° C. overnight. The phases are separated, and the organic phase is washed with water (3×80 mL), and two thirds of the chloroform is then evaporated. Ethanol (150 mL) is added to precipitate the product, which is filtered on a Büchner funnel. The dried solid is then purified by soxhlet extraction, first with cyclohexane (160 mL, 21 h). The fraction soluble in cyclohexane is discarded and the remaining solid is then subjected to soxhlet extraction with tetrahydrofuran (160 mL, 24 h). The solution is concentrated, the product is precipitated in ethanol, filtered and dried under reduced pressure to afford a first fraction of polymer P-6 (410 mg, yield 53%, $M_w$=66400, PD=2.01). The remaining solid is then subjected to another soxhlet extraction with chloroform (160 mL, 2.5 h). The solution is concentrated, the product is precipitated in ethanol, filtered and dried under reduced pressure to afford the higher molecular weight fraction of polymer P-7 (258 mg, yield 34%, $M_w$=81600, PD=2.39).

High temperature GPC: Chloroform fraction: $M_w$=81600, PD 2.39.

Example 8

Synthesis of Polymer P-8

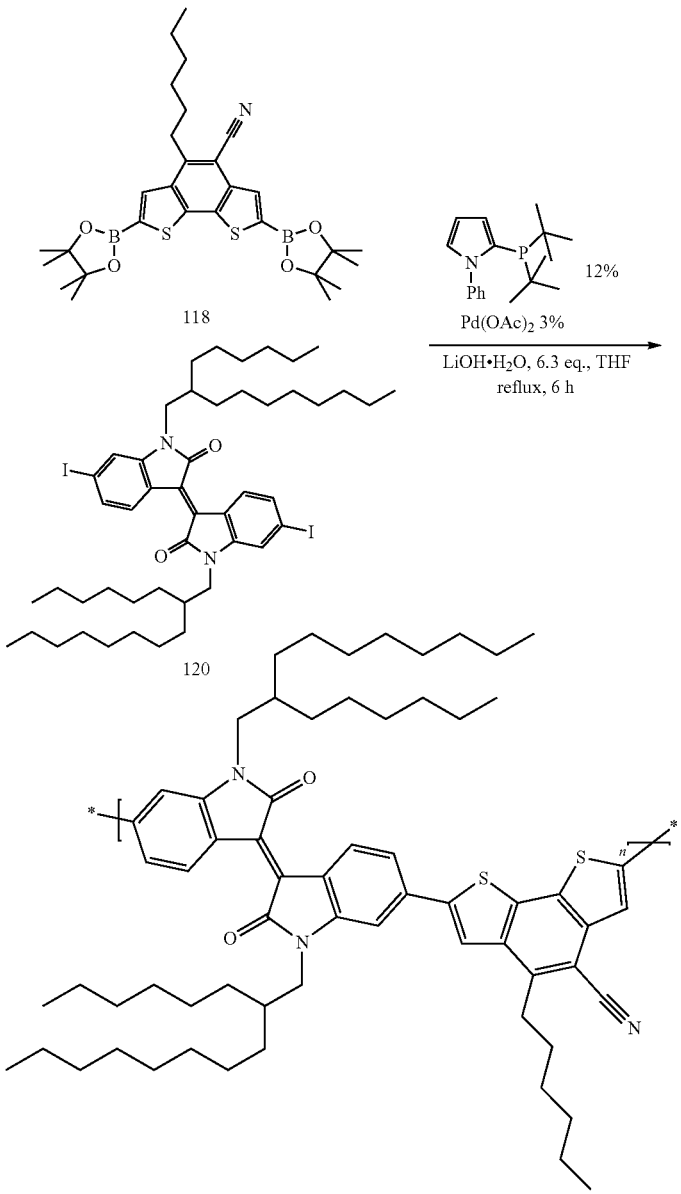

P-8 a) Compound 120 can be for example prepared from ((6,6'-dibromo-N,N'-(2-hexyldecanyl)isoindigo) using similar method to the one described in Klapars, A.; Buchwald, S. L.; *J. Am. Chem. Soc.,* 2002, 124, 14844-14845.

In a 200 mL flask equipped with a condenser, a mechanical stirrer, a nitrogen bubbler and a thermometer is introduced bis-boronic ester 118 (434 mg, 0.79 mmol) and compound 120 (722 mg, 0.75 mmol), and dry THF (40 mL) is added by syringe. The resulting red solution is heated to 60° C. and a solution of palladium(II) acetate (5.1 mg, 0.022 mmol) and 2-(di-tert-butylphosphino)-1-phenylpyrrole (25.9 mg, 0.090 mmol) in 10 mL THF is added. The resulting mixture is stirred for 5 minutes at reflux temperature. After that time finely crushed lithium hydroxide monohydrate (198 mg, 4.72 mmol) is added in a single portion at 60° C. and is stirred at reflux temperature for 6 hours. The reaction mixture is poured into ethanol (400 mL) and the precipitate is filtered on a Büchner funnel. The solid is then washed with 200 mL ethanol and 200 mL deionised water. The filtered solid is then put in a flask containing 150 mL chloroform and 150 mL of a 3% sodium cyanide aqueous solution and is heated under vigorous stirring at 60° C. overnight. The phases are then separated, and the organic phase is washed with water (3×100 mL), and the chloroform is then evaporated. Ethanol is added to precipitate the product, which is filtered on a Büchner funnel, washed with water (200 mL) and ethanol (50 mL) and dried in the oven. The treatment with sodium cyanide is then repeated a second time. The dried solid is then purified by soxhlet extraction, first with acetone (200 mL, 5 h). The fraction soluble in acetone is discarded and the remaining solid is then subjected to soxhlet extraction with cyclohexane (200 mL, 7 h). The solvent is then evaporated, and the product is precipitated in ethanol, filtered and dried under reduced pressure to afford the polymer P-8 (640 mg, yield 85%).

High temperature GPC: $M_w$=19500, PD=1.38.

Example 9

Synthesis of Monomer 125

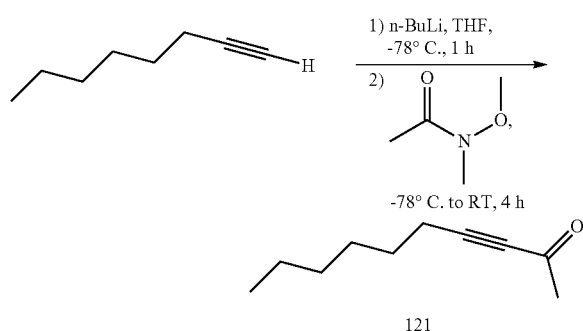

a) To a solution of 1-octyne in tetrahydrofuran (THF, 180 mL) previously cooled to −78° C. is added under nitrogen n-buyllithium (2.5 M solution in hexane, 33.2 mL, 83 mmol). The colorless mixture is stirred 1 h and is then treated with N-methoxy-methylacetamide in THF (20 mL). The reaction mixture is stirred at room temperature for 4 h. After that time 3M HCl solution (100 mL) is added. Tert-butyl-methyl ether (TBME) is added and the reaction mixture is extracted with TBME (3×100 mL). The combined organic layers are washed with saturated $NaHCO_3$, dried over magnesium sulphate and the volatiles are removed on rotary evaporator. The residue is then purified by flash column chromatography (eluent: ethyl acetate/hexane 1:10) to obtain product 121 (colorless oil, 6.2 g, yield: 64%).

NMR: $^1$H (400.1 MHz, $CDCl_3$), δ=2.35 (2H, t, J=7.2 Hz), 2.31 (3H, s), 1.57 (2H, quint., J=7.2 Hz), 1.43-1.35 (2H, m), 1.33-1.25 (4H, m), 0.89 (3H, t, J=7.0 Hz); $^{13}$C (100.1 MHz, $CDCl_3$), δ=184.9, 94.2, 81.4, 32.7, 31.2, 28.5, 27.6, 22.4, 18.9, 14.0.

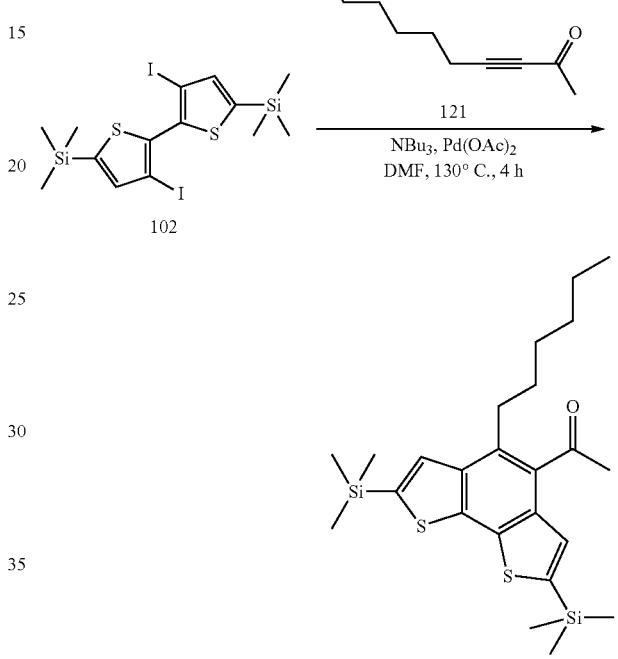

b) In a 500 mL flask equipped with a condenser is introduced compound 102 (8.87 g, 15.76 mmol) and dimethyl formamide (DMF, 150 mL) under nitrogen. After, compound 121 (4.8 g, 31.53 mmol) is added under nitrogen at room temperature, followed by and $Pd(OAc)_2$ (354 mg, 1.58 mmol) and tributylamine (5.84 g, 31.53 mmol). The reaction mixture is then heated to 130° C. for 4 h. After that time the solution is cooled to room temperature and poured into water (200 mL). Dichloromethane is added and the aqueous phase is extracted with dichloromethane (2×200 mL). The combined organic phases are dried over magnesium sulphate, filtered and the solvent was evaporated on rotary evaporator to give a dark brown oil. The crude dark brown oil is purified by two successive flash column chromatographies: first with hexanes/ethyl acetate 20:1 as eluent, and then with cyclohexane/toluene 1:1 as eluent to obtain product 122 (oil, 3.45 g, 47% yield).

NMR: $^1$H (400.1 MHz, $CDCl_3$), δ=7.58 (1H, s), 7.33 (1H, s), 2.97 (2H, t, J=8.0 Hz), 2.68 (3H, s), 1.75-1.66 (2H, m), 1.47-1.41 (2H, m), 1.37-1.31 (4H, m), 0.90 (3H, t, J=7.0 Hz); $^{13}$C (100.1 MHz, $CDCl_3$), δ=206.7, 141.5, 141.0, 138.1, 137.9, 135.9, 134.5, 133.3, 130.1, 130.0, 129.2, 33.1, 31.8, 31.5, 29.7, 29.6, 22.6, 14.0, −0.2 (6C); GC/MS: (CI pos.): 461.36 ($MH^+$).

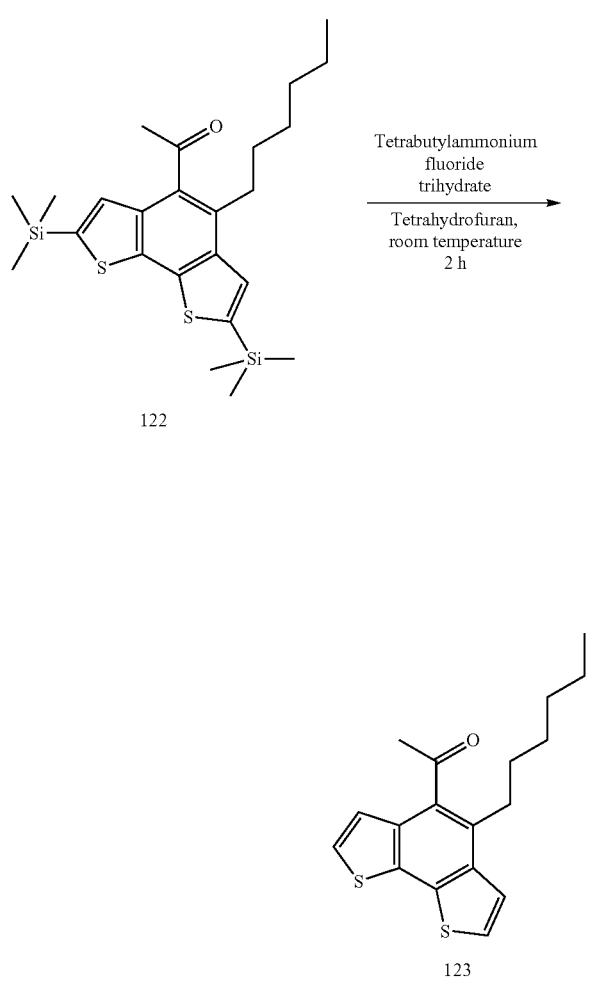

122

123 c) In a 500 mL flask, equipped with a condenser, is introduced under nitrogen atmosphere compound 122 (3.40 g, 7.38 mmol) and THF (100 mL). Tetrabutyl ammonium fluoride (TBAF, 5.12 g, 16.23 mmol) is then slowly added at room temperature as a THF solution, and the resulting solution is stirred 2 h at room temperature. After that time the solution is poured into water (300 mL), and extracted with tert-butyl-methyl-ether (1×200 mL) and dichloromethane (2×200 mL). The combined organic fractions are dried over sodium sulphate, filtered and the solvent is evaporated on rotatory evaporator. The crude dark brown oil is purified by column chromatography (Silica gel, cyclohexane/toluene, 60:40 then 40:60, Rf=0.45 in cyclohexane/toluene 60:40. This affords the desired product 123 (dark yellow oil, 2.1 g, yield: 90%).

NMR: $^1$H (400.1 MHz, CDCl$_3$), δ=7.52 (1H, d, J=5.5 Hz), 7.47 (1H, d, J=5.3 Hz), 7.44 (1H, d, J=5.5 Hz), 7.27 (1H, d, J=5.3 Hz), 2.96 (2H, m), 2.67 (3H, s), 1.74-1.66 (2H, m), 1.47-1.40 (2H, m), 1.36-1.29 (4H, m), 0.90 (3H, m); $^{13}$C (100.6 MHz, CDCl$_3$), δ=206.1, 136.6, 134.4, 133.6, 133.1, 132.1, 130.4, 125.1, 124.7, 123.5, 122.8, 32.9, 31.9, 31.6 (2C), 29.7, 22.6, 14.0; GC/MS: (CI pos.): 317.14 (MH$^+$).

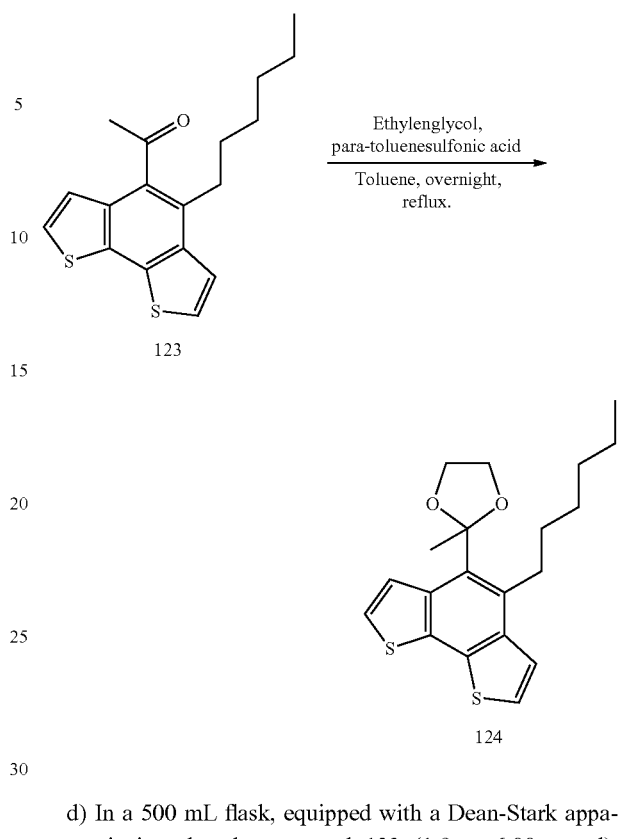

123

124 d) In a 500 mL flask, equipped with a Dean-Stark apparatus, is introduced compound 123 (1.9 g, 6.00 mmol), p-toluenesulfonic acid (230 mg, 1.20 mmol), ethyleneglycol (0.82 g, 13.21 mmol) and toluene (200 mL). The resulting solution is heated at reflux for 3 days. After that time, approximately ⅔ of the start. material has reacted. The reaction is stopped. The mixture is left to cool to room temp. Water is added (200 mL) followed by tert-butyl-methylether (150 mL). The phases are separated and the organic phase is washed with a saturated NaHCO$_3$ aqueous solution (100 mL). The combined organic fractions are dried over anhydrous sodium sulfate and filtered. The solvents are removed on rotatory evaporated to get the crude material (yellow oil). The crude is then further purified by column chromatography (Silica, eluent: cyclohexane/toluene 40:60) to afford the product as a yellow oil (1.12 g) and unreacted starting material (630 mg). The unreacted starting material is reacted again under similar conditions for 72 h. After purification, another fraction of product is collected (462 mg, yellow oil). Total amount of product 124 obtained after purification: 1.58 g (yellow oil, 73% yield).

NMR: $^1$H (400.1 MHz, CDCl$_3$), δ=8.2 (1H, d, J=5.5 Hz), 7.50 (1H, d, J=5.5 Hz), 7.39 (1H, d, J=5.5 Hz), 7.34 (1H, d, J=5.5 Hz), 4.06 (2H, m), 3.73 (2H, m), 3.27 (2H, m), 1.88 (3H, s), 1.76-1.70 (2H, m), 1.60-1.55 (2H, m), 1.44-1.37 (4H, m), 0.95 (3H, m); $^{13}$C (100.6 MHz, CDCl$_3$), δ=138.3, 135.1, 133.5, 133.4, 132.6, 132.2, 127.1, 124.1, 123.7, 122.7, 111.0, 64.1 (2C), 32.4, 31.9, 31.7, 30.3, 27.8, 22.7, 14.1; GC/MS: (CI pos.): 361.15 (MH$^+$).

Example 10

Synthesis of Polymer P-9

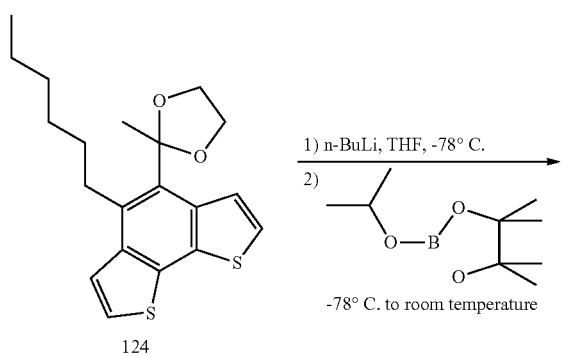

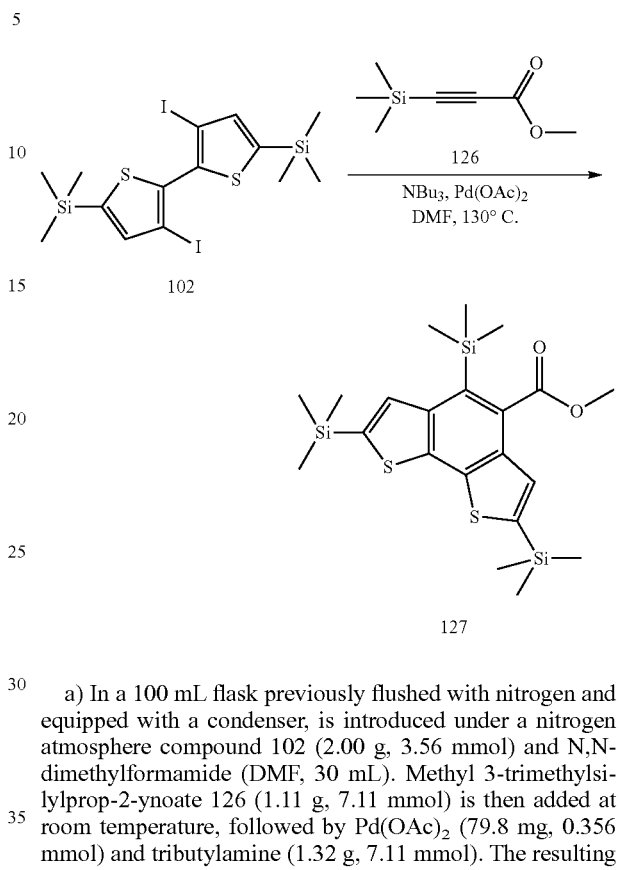

e) In a 250 mL flask is introduced under a nitrogen atmosphere compound 124 (as a solution in 20 mL tetrahydrofuran) and tetrahydrofuran (80 mL). The yellow solution is then cooled to −78° C. and n-butyllithium (2.5 M solution, 2.68 mL, 6.71 mmol) is added dropwise under nitrogen. The resulting mixture is stirred for 1 h 20 at −78° C. After that time isopropoxy pinacol borane is added at −78° C. The mixture turns to a clear yellow solution. After 20 minutes at −78° C., the mixture is allowed to warm to room temperature and stirred 2 hours at room temperature. Then, water is added at 0° C., followed by 1 M HCl (15 mL). Phases are separated and the aqueous phase is extracted with tert-butyl-methyl ether (TBME, 100 mL) and dichloromethane (2×100 mL). The combined organic fractions are then dried over $Na_2SO_4$, filtered, concentrated on rotavap. The crude yellow oil is then treated several times with active charcoal (500 mg) in hexanes and filtered to remove side products. Solvent is then evaporated to obtain compound 125 (yellow solid, 789 mg, yield: 42%)

NMR: $^1$H (400.1 MHz, CDCl$_3$), □=8.68 (1H, s), 8.00 (1H, s), 4.05 (2H, m), 3.73 (2H, m), 3.27 (2H, m), 1.87 (3H, s), 1.73-1.67 (2H, m), 1.58-1.52 (2H, m), 1.44-1.23 (4H, m), 1.39 (12H, s), 1.37 (12H, s) 0.93 (3H, m).

a) In a 100 mL flask previously flushed with nitrogen and equipped with a condenser, is introduced under a nitrogen atmosphere compound 102 (2.00 g, 3.56 mmol) and N,N-dimethylformamide (DMF, 30 mL). Methyl 3-trimethylsilylprop-2-ynoate 126 (1.11 g, 7.11 mmol) is then added at room temperature, followed by Pd(OAc)$_2$ (79.8 mg, 0.356 mmol) and tributylamine (1.32 g, 7.11 mmol). The resulting solution is then heated at 135° C. for 5 h. After that time the solution is cooled to room temperature and poured into water (200 mL) and extracted with dichloromethane (2×200 mL). The combined organic fractions are dried over sodium sulphate, filtered and the solvent is evaporated on rotary evaporator to obtain a dark brown oil. The crude is then further purified by column chromatography (Cyclohexane/toluene 2:1) to obtain product 127 (white solid, 0.50 g, yield: 30%).

NMR: $^1$H (400.1 MHz, CDCl$_3$), δ=7.79 (1H, s), 7.53 (1H, s), 4.00 (3H, s), 0.46 (9H, s), 0.42 (9H, s), 0.40 (9H, s); $^{13}$C (100.1 MHz, CDCl$_3$), δ=171.0, 141.6, 141.1, 140.2, 138.8, 138.6, 135.3, 133.1, 131.8, 130.1, 129.8, 52.2, 1.4 (3C), −0.2 (3C), −0.3 (3C); GC/MS: (CI pos.): 465.16 (MH$^+$).

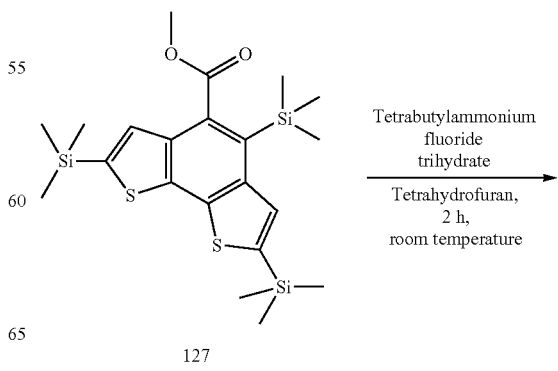

-continued

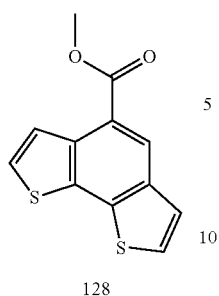

128 b) In a 500 mL flask is introduced, under a nitrogen atmosphere compound 127 (350 mg, 0.75 mmol) and tetrahydrofurane (THF, 10 mL). A solution of tetrabutylammonium fluoride trihydrate (0.83 g, 2.64 mmol) in tetrahydrofurane (10 mL) is then slowly added at room temperature. The resulting solution is stirred 2 h at room temperature. After that time the solution is poured into water (100 mL), and extracted with tert-butyl-methyl ether (1×100 mL) and dichloromethane (2×100 mL). The combined organic fractions are dried over sodium sulphate, filtered and the solvent is evaporated on rotary evaporator. The crude is then purified by column chromatography (cyclohexane/toluene 1:1) to obtain compound 128 (white solid, 177 mg, yield: 95%).

NMR: $^1$H (400.1 MHz, CDCl$_3$), δ=8.57 (1H, s), 8.32 (1H, d, J=5.5 Hz), 7.53 (1H, d, J=5.5 Hz), 7.49 (1H, d, J=5.5 Hz), 7.45 (1H, d, J=5.5 Hz), 4.02 (3H, s); $^{13}$C (100.1 MHz, CDCl$_3$), δ=167.3, 138.0, 136.1, 135.5, 134.8, 125.7, 125.6, 125.2, 125.1, 124.3, 121.9, 52.0; GC/MS: (CI pos.): 249.05 (MH$^+$).

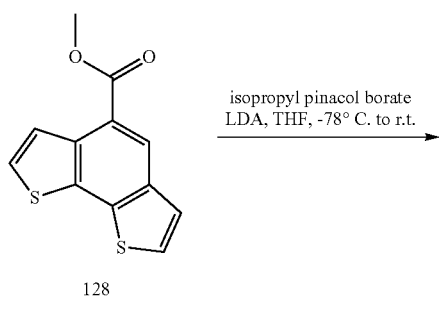

128 isopropyl pinacol borate
LDA, THF, -78° C. to r.t.
→

-continued

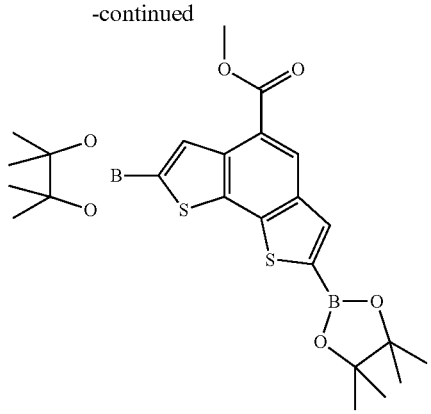

129 c) In a 3-neck flask equipped with a condenser and an addition funnel are introduced, under nitrogen, compound 128 (1.614 g, 6.5 mmol) and tetrahydrofuran (THF, 12.5 mL) followed by isopropoxypinacolborane (2.660 g, 14.3 mmol). The resulting solution is then cooled to −78° C. and a previously prepared lithium diisopropylamide solution (LDA, 13.32 mmol in 12.5 mL THF) is added dropwise. The reaction mixture is left to stir 1 h at −78° C. and is then allowed to warm to room temperature and stir for 1 hour at room temperature. After that time the reaction mixture is poured in 50 mL of HCl 2N and extracted with tert-butyl-methyl ether (TBME, 2×35 mL). The combined organic layers are washed with 50 mL water and 50 mL brine, then dried over sodium sulphate, filtered and the solvent is evaporated on rotary evaporator. The crude is then recrystallised from warm diisopropylether, filtered, and the obtained crystals are then washed with diisopropylether and dried under vacuum to obtain the pure product 129 (beige crystals, 2.420 g, yield: 73%).

NMR: $^1$H (400.1 MHz, CDCl$_3$), δ=8.79 (1H, s), 8.55 (1H, s), 8.01 (1H, s), 4.03 (3H, s), 1.39 (24H, s).

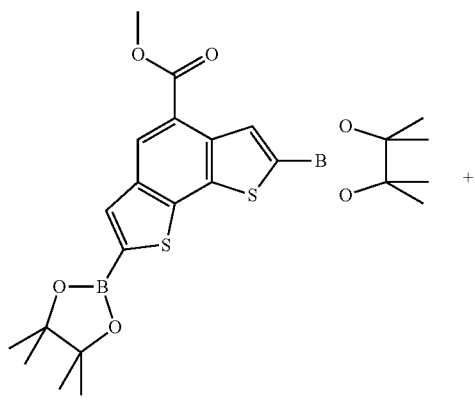

129

-continued

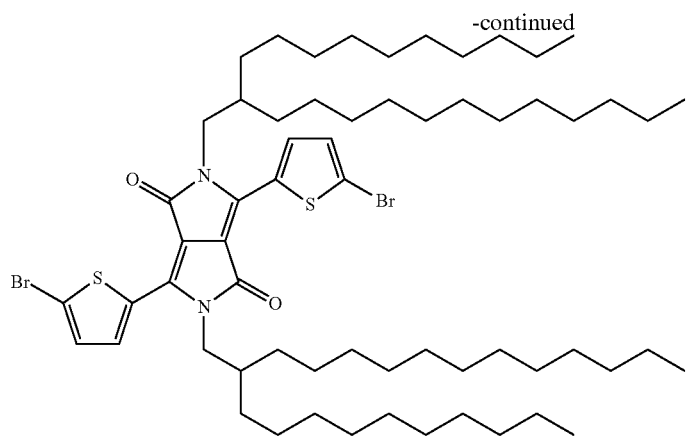

130

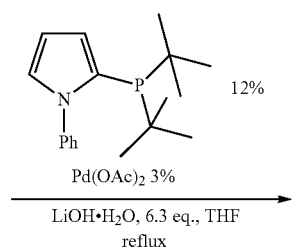

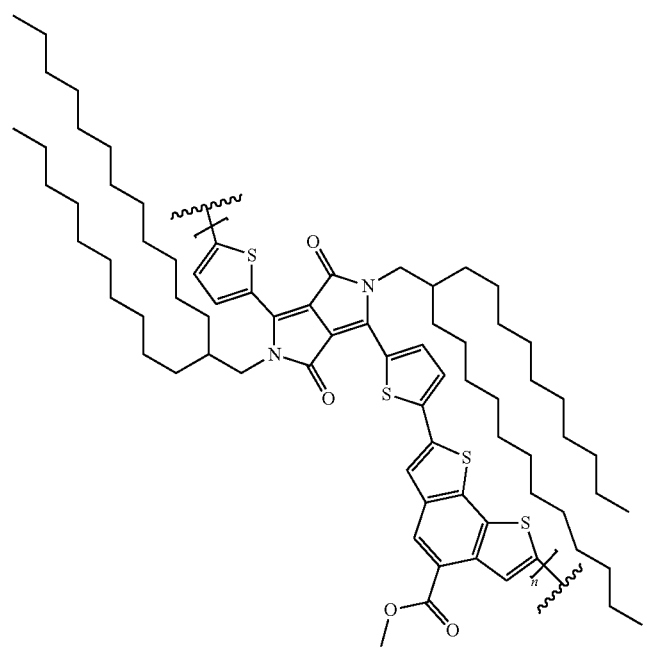

P-9 d) The synthesis of 3,6-bis(5-bromothiophen-2-yl)-2,5-bis(2-decyltetradecyl)pyrrolo[3,4-c]pyrrole-1,4(2H,5H)-dione 130 is, for example, described in Lee, J.; Cho, S.; Yang, C.; *J. Mater. Chem.*, 2011, 21, 8528-8531.

In a 200 mL flask equipped with a condenser, a mechanical stirrer, an argon inlet and a thermometer is introduced the bis-boronic ester 129 (400 mg, 0.800 mmol) and 3,6-bis(5-bromothiophen-2-yl)-2,5-bis(2-decyltetradecyl)pyrrolo[3,4-c]pyrrole-1,4(2H,5H)-dione 130 (862 mg, 0.762 mmol). The flask is flushed with argon and dry THF (40 mL) is added by syringe. The resulting red solution is heated to reflux and a previously prepared solution of palladium(II) acetate (5.1 mg, 0.023 mmol) and 2-(di-tert-butylphosphino)-1-phenylpyrrole (26.2 mg, 0.091 mmol) in 10 mL THF is added at 60° C. The resulting mixture is stirred for 5 minutes at reflux temperature. After that time finely crushed lithium hydroxide monohydrate (201 mg, 4.80 mmol) is added in a single portion at 60° C. and is stirred at reflux temperature for 2.5 hours. After that time, the heating is stopped and the mixture is poured in methanol (400 mL) to precipitate the product. The polymer is filtered, and washed with water. The filtered solid is then put in a flask containing 150 mL chloroform and 150 mL of a 3% sodium cyanide aqueous solution and is heated under vigorous stirring at 55° C. for 4 h. The phases are separated and the organic phase is washed with water (3×100 mL). Chloroform is then evaporated, and methanol is added to precipitate the product, which is filtered on a Büchner funnel, washed with water (200 mL) and methanol (50 mL) and dried in the oven. The treatment with sodium cyanide is then repeated a second time. The dried solid is then purified by soxhlet extraction, first with THF (200 mL, 4 h). The fraction soluble in tetrahydrofuran is discarded and the remaining solid is then subjected to soxhlet extraction with chloroform (200 mL, 8 h). The solution is concentrated, the product is precipitated in methanol, filtered and dried under reduced pressure to afford the polymer P-9 (812 mg, yield 82%). High temperature GPC: $M_w$=83300, PD 2.98.

APPLICATION EXAMPLES

Photovoltaic Application of the Semiconducting Polymers

The solar cell has the following structure: Al electrode/ LiF layer/organic layer, including compound of the invention/[poly(3,4-ethylenedioxy-thiophene) (PEDOT)/poly (styrenesulfonic acid) (PSS)]/ITO electrode/glass substrate. The solar cells are made by spin coating a layer of the PEDOT-PSS on a pre-patterned ITO on glass substrate. Then a 1:X mixture of the semiconducting polymer (1% by weight): [70]PCBM (a substituted $C_{70}$ fullerene) is spin coated (organic layer). LiF and Al are sublimed under high vacuum through a shadow-mask.

Solar Cell Performance

The solar cell is measured in homemade solar light simulator with Osram Xenon Short Arc XBO 450W lamp. Then with the External Quantum Efficiency (EQE) graph the current is estimated under AM1.5 conditions. The OPV performances of Semiconducting polymers are shown in the table below:

| Example | Polymer | Solvent | Polymer:70PCBM ratio | Voc, V | Jsc, mA/cm² | FF, % | η, % |
|---|---|---|---|---|---|---|---|
| 1 | P-1 | 3-Methylthiophene/1-Methylnaphtalene (8:2) | 1:2 | 0.84 | −3.29 | 53.81 | 1.49 |
| 2 | P-2 | CHCl₃/oDCB[1] (7:3) | 1:2.5 | 0.76 | −14.20 | 44.94 | 4.74 |
| 3 | P-3 | 3-Methylthiophene/1-Methylnaphtalene (8:2) | 1:2 | 0.82 | −9.50 | 62.98 | 4.87 |
| 4 | P-4 | CHCl₃/oDCB (8:2) | 1:2 | 0.8 | −3.21 | 57.02 | 1.46 |
| 5 | P-5 | Xylene/Tetraline (9:1) | 1:2 | 0.78 | −4.13 | 66.89 | 2.17 |
| 6 | P-6 | CHCl₃/oDCB (8:2) | 1:2 | 0.88 | −2.82 | 55.03 | 1.37 |
| 7 | P-7 | CHCl₃/oDCB (8:2) | 1:2 | 0.94 | −4.00 | 44.88 | 1.71 |
| 8 | P-8 | Xylene/Tetraline (8:2) | 1:2 | 1.00 | −0.20 | 29.02 | 0.06 |
| 9 | P-9 | CHCl₃/oDCB (8:2) | 1:2 | 0.80 | −9.25 | 68.47 | 5.14 |

[1] oDCB = ortho-dichlorobenzene.

OFET Application of the Semiconducting Polymers:

Semiconductor Film Deposition:

Siliconwafers (Si n⁻⁻(425±40 μm)) with a 230 nm thick $SiO_2$ dielectric and patterned indium tin oxide (15 nm)/gold (30 nm) contacts (L=20, 10, 5, 2.5 μm, W=0.01 m; Fraunhofer IPMS (Dresden)) are prepared by standard cleaning by washing with acetone and i-propanol followed by oxygen plasma treatment for 30 minutes.

The substrates are transferred in a glove box. An octyltrichlorsilane (OTS) monolayer is grown on the dielectric surface by putting the substrates in a 50 mM solution of octyltrichlorosilane (OTS) in trichloroethylene for 1 h. After monolayer growth, the substrates are washed with toluene to remove physisorbed silane.

The semiconductor is dissolved in a proper solvent in a concentration 0.75% by weight at 80° C. and spin-coated at 1500 rpms for 60 s onto the substrates.

OFET Measurement:

OFET transfer and output characteristics are measured on an Agilent 4155C semiconductor parameter analyzer. The devices are annealed in a glovebox at 150° C. for 15 minutes before the measurements are done in a glove box under a nitrogen atmosphere at room temperature. For p-type transistors the gate voltage ($V_g$) varies from 10 to −30 V and at drain voltage ($V_d$) equal to −3 and −30V for the transfer characterisation. For the output characterization $V_d$ is varied from 0 to −30V at $V_g$=0, −10, −20, −30 V.

| Example | Semiconductor | Solvent | Mobility, cm²/Vs | On/off |
|---|---|---|---|---|
| 10 | P-1 | oDCB | 8.90E−04 | 7.20E+04 |
| 11 | P-2 | oDCB | 5.90E−03 | 5.10E+05 |
| 12 | P-3 | oDCB | 3.70E−03 | 4.50E+04 |
| 13 | P-4 | oDCB | 1.40E−03 | 1.60E+04 |
| 14 | P-5 | oDCB | 1.50E−03 | 1.60E+04 |
| 15 | P-6 | oDCB | 3.40E−03 | 1.10E+06 |
| 16 | P-7 | oDCB | 3.60E−03 | 3.1E+05 |
| 17 | P-8 | oDCB | 3.10E−08 | 4.50E+04 |
| 18 | P-9 | oDCB | 2.10E−02 | 8.8E+04 |

When used in OPV cells, the polymers of the present invention show an improved short circuit voltage (Voc), while maintaining high short circuit current (Jsc) compared to polymers, wherein $R^1$ and $R^2$ are both hydrogen, or alkyl. The modifications of the benzodithiophene structure have a direct effect on Voc, as the introduction of electron withdrawing groups such as —COOR³⁰¹ or —CN modifies the HOMO level of the polymer. This leads to improved efficiencies.

As a comparison L. Huo et al. Macromolecules, 42 (2009) 6564-6571 obtained a $V_{oc}$ of 0.72 V and max. PCE of 4.45% with a polymer of formula

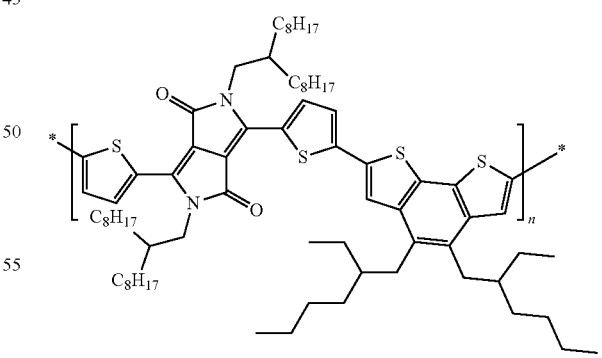

(PDPPBDP) and 70PCBM., comprising a benzodithiophene repeating unit with $R^1$=$R^2$=branched alkyl groups. Yuan et. al, Journal of Polymer Science Part A: Polymer Chemistry, 49 (2011) 701-711 obtained a maximum $V_{oc}$ of 0.76 V and PCE of 0.43% with

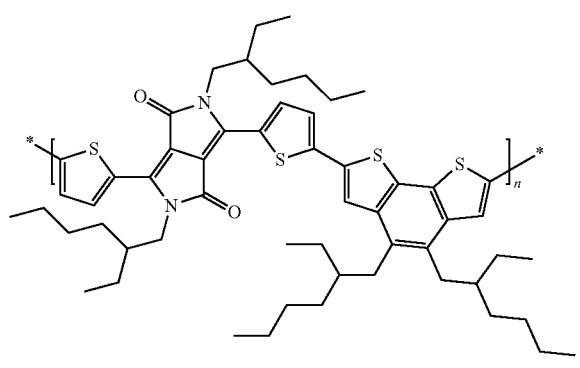

(PBDPDPP) and 70PCBM.

Another advantage of the polymers described in this invention is their very good solubility and film forming properties in common solvents, comprising non-halogenated solvents. Additionally, as $R^1$ and $R^2$ are not directly in the vicinity of the twistable bonds of the conjugated backbone the steric impact of modification of $R^{301}$, $R^{302}$, or $R^{303}$ (on their respective functional group) on the electronic properties are very limited and in most cases inexistent. In other words, in the case $R^2$=—$COOR^{301}$, for example, the solubility and film forming properties of the polymers can be independently adjusted by variations of the $R^{301}$ group. Thus you can decouple the tuning of the electronic properties from the tuning of the film morphology which can be a decisive advantage in the development of such polymers. Finally, the variation of $R^{301}$ and $R^{303}$ in particular can be done at a late stage of the synthesis which helps expediting the development.

The invention claimed is:

1. A polymer, comprising a repeating unit of the formula

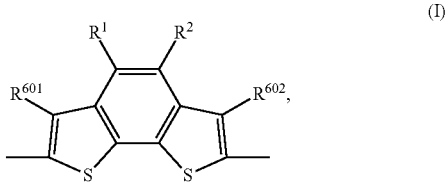

(I)

wherein $R^1$ is hydrogen, $C_1$-$C_{100}$alkyl, or a group of formula —$SiR^{501}R^{502}R^{503}$;

$R^2$ is —CN, —$CF_3$, a fluorine atom, or a group of the formula

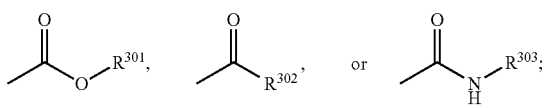

$R^{301}$, $R^{302}$ and $R^{303}$ are independently of each other $C_1$-$C_{18}$alkyl, $C_1$-$C_{18}$alkyl which is substituted by E' and/or interrupted by D', $C_1$-$C_{100}$fluoroalkyl, $C_3$-$C_{12}$cycloalkyl, $C_6$-$C_{24}$aryl, $C_6$-$C_{24}$aryl group, which is be substituted by G'; $C_2$-$C_{18}$alkenyl, $C_2$-$C_{18}$alkynyl, $C_7$-$C_{25}$aralkyl, or $C_7$-$C_{25}$aralkyl which is substituted by G'; $C_2$-$C_{20}$heteroaryl, or $C_2$-$C_{20}$heteroaryl, which is substituted by G';

$R^{601}$ and $R^{602}$ are independently of each other H, or $C_1$-$C_{25}$alkyl;

$R^{501}$, $R^{502}$ and $R^{503}$ are independently of each other $C_1$-$C_8$alkyl, $C_6$-$C_{24}$aryl, or $C_7$-$C_{12}$aralkyl;

D' is —CO—, —COO—, —S—, —SO—, —$SO_2$—, —O—, —$NR^{65}$—, —$SiR^{70}R^{71}$—, —$POR^{72}$—, —$CR^{63}$=$CR^{64}$—, or —C≡C—, and E' is —$OR^{69}$, —$SR^{69}$, —$NR^{65}R^{66}$, —$COR^{68}$, —$COOR^{67}$, —$CONR^{65}R^{66}$, —CN, $CF_3$, or halogen, G' is E', $C_1$-$C_{18}$alkyl, or $C_1$-$C_{18}$alkyl which is interrupted by —O—, $R^{63}$ and $R^{64}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^{65}$ and $R^{66}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—; or $R^{65}$ and $R^{66}$ together form a five or six membered ring, $R^{67}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl;

or $C_1$-$C_{18}$alkyl which is interrupted by —O—, $R^{68}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{69}$ is $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{70}$ and $R^{71}$ are independently of each other $C_1$-$C_{18}$alkyl, $C_6$-$C_{18}$aryl, or $C_6$-$C_{18}$aryl, which is substituted by $C_1$-$C_{18}$alkyl, and $R^{72}$ is $C_1$-$C_{18}$alkyl, $C_6$-$C_{18}$aryl, or $C_6$-$C_{18}$aryl, which is substituted by $C_1$-$C_{18}$alkyl.

2. The polymer according to claim 1, which is a polymer comprising a repeating unit of the formula

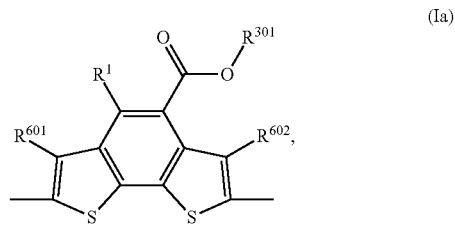

(Ia)

wherein $R^1$ is hydrogen, or $C_1$-$C_{100}$alkyl, $R^{301}$ is $C_1$-$C_{18}$alkyl, phenyl, phenyl, which is substituted by one, or more groups selected from $C_1$-$C_{18}$alkyl, halogen, $OR^{69}$, CN, or $CF_3$; wherein $R^{69}$ is $C_1$-$C_{18}$alkyl, or phenyl;

$R^{601}$ and $R^{602}$ are the same and are hydrogen or $C_1$-$C_{18}$alkyl.

3. The polymer according to claim 1, which is a polymer comprising a repeating unit of the formula (Ib)
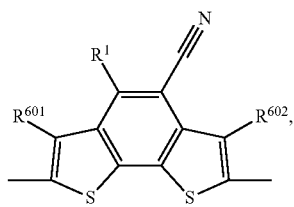

wherein

R¹ is hydrogen, or $C_1$-$C_{100}$alkyl, and $R^{601}$ and $R^{602}$ are the same and are hydrogen, or $C_1$-$C_{18}$alkyl.

4. The polymer according to claim 1, wherein the polymer is a polymer of formula

or a polymer, comprising repeating units of the formula

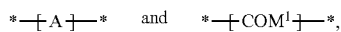

wherein n is in the range of 4 to 1000,

A is a repeating unit of formula (I), and

—COM1- is a repeating unit

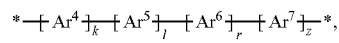

wherein k is 0, 1, 2, or 3; l is 1, 2, or 3; r is 0, 1, 2, or 3; z is 0, 1, 2, or 3;

$Ar^4$, $Ar^5$, $Ar^6$ and $Ar^7$ are independently of each other a group of formula and (XIa)
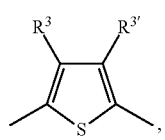

(XIb)
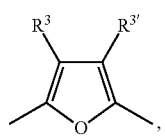

(XIc)
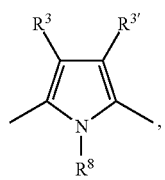

(XId)
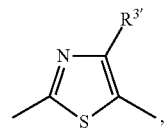

(XIe)
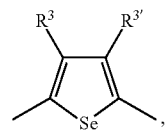

(XIf)
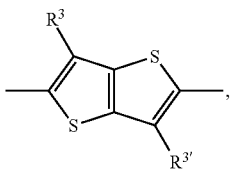

(XIg)
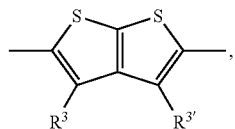

(XIh)
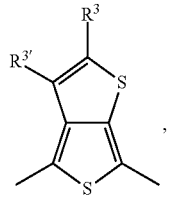

(XIi)
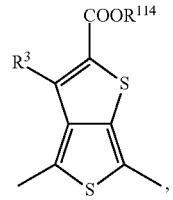

(XIj)
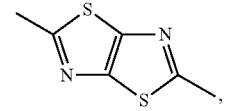

(XIk)
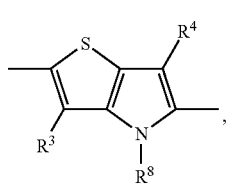

(XIl)
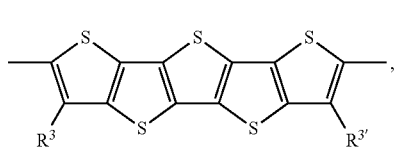

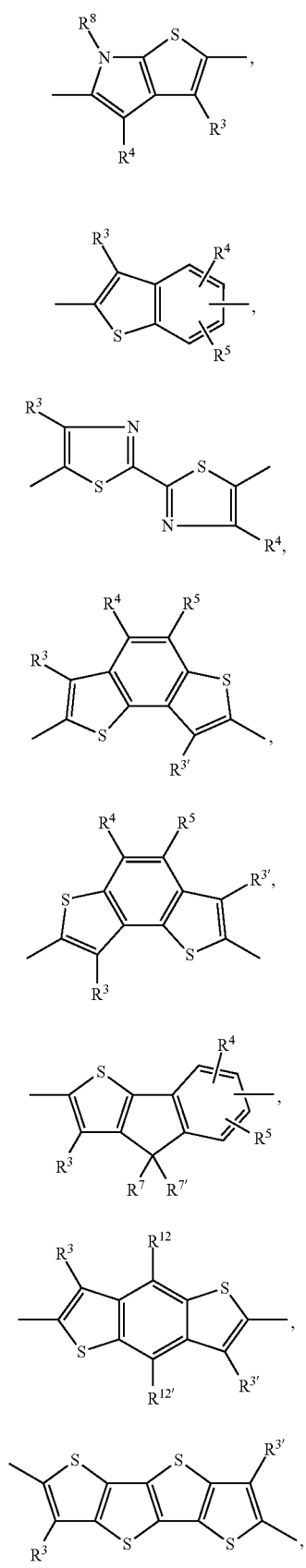
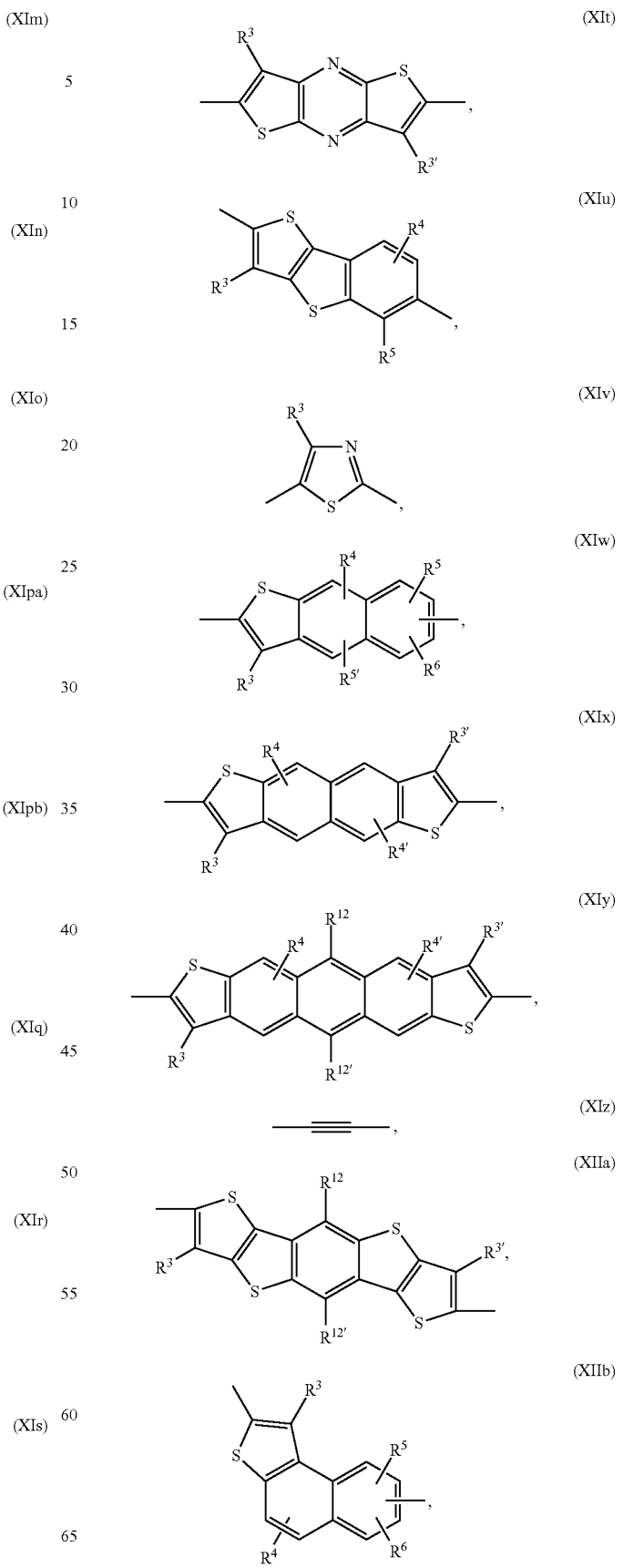

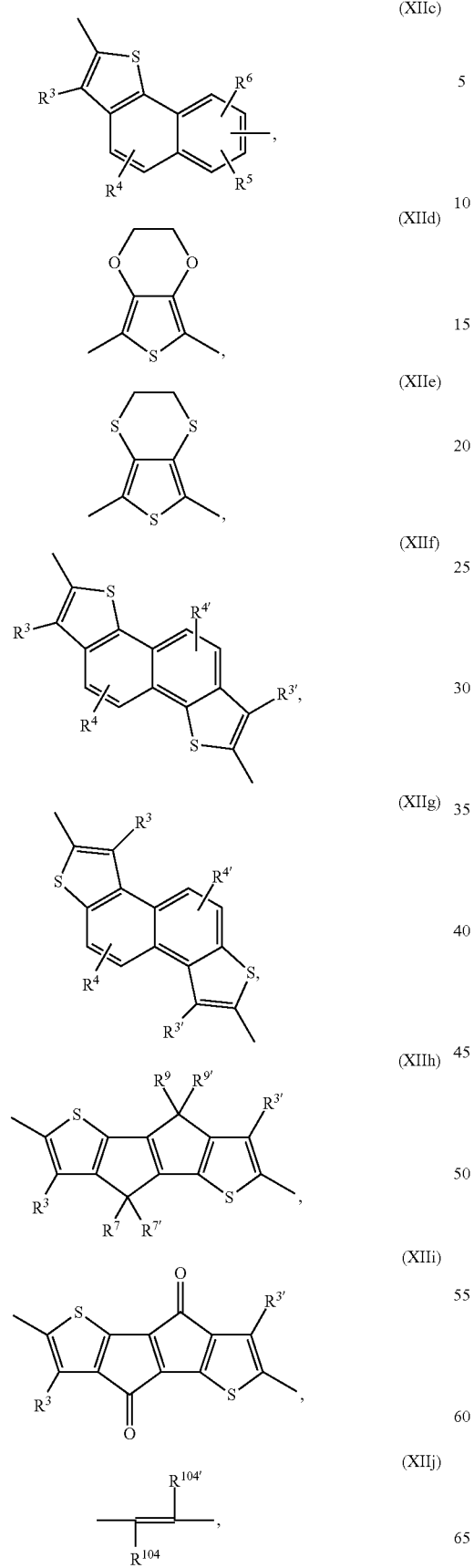

-continued
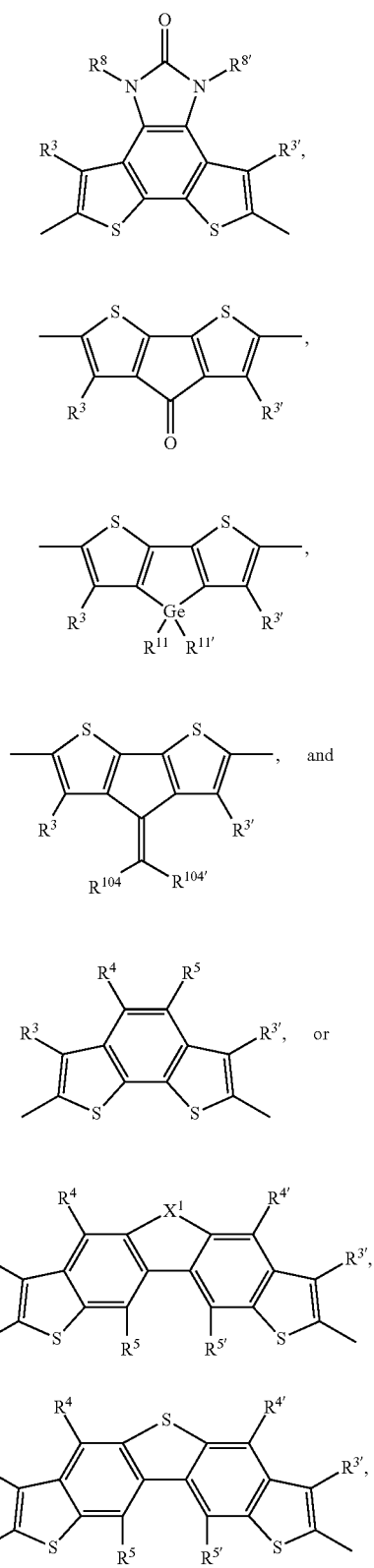
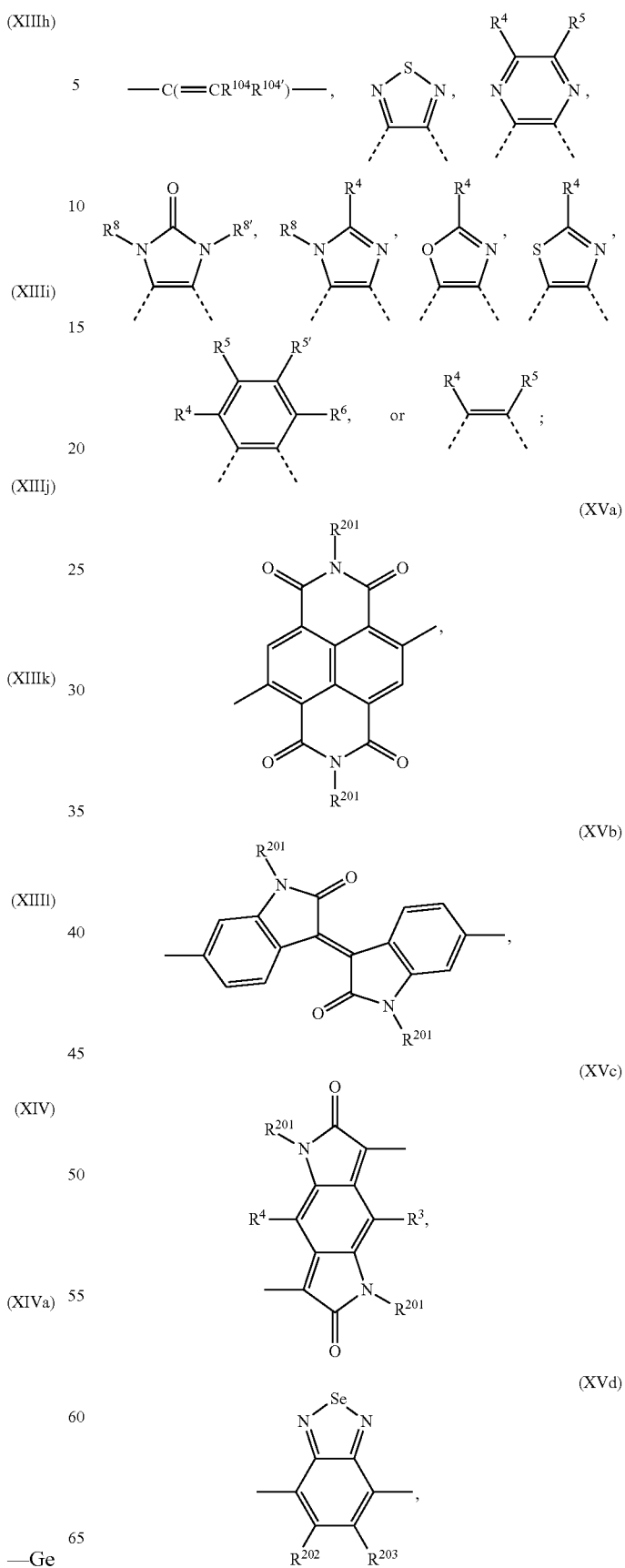
wherein
X is —O—, —S—, —NR[8]—, —Si(R[11])(R[11'])—, —Ge(R[11])(R[11'])—, —C(R[7])(R[7'])—, —C(=O)—, -continued
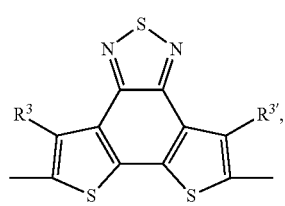 (XVe)
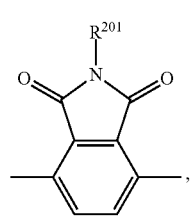 (XVf)
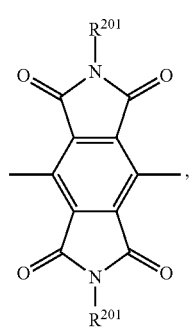 (XVg)
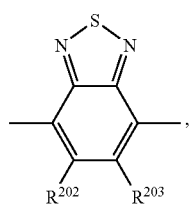 (XVh)
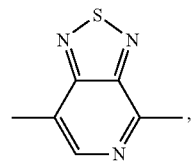 (XVi)
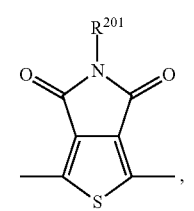 (XVj)
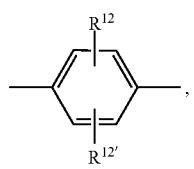 (XVk)
-continued
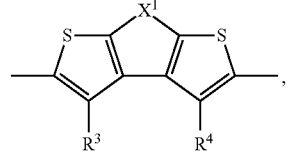 (XVl)
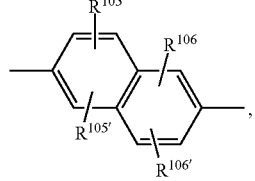 (XVm)
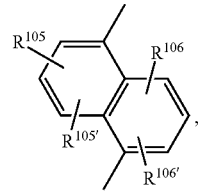 (XVn)
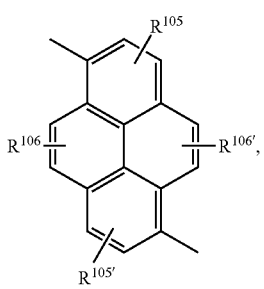 (XVo)
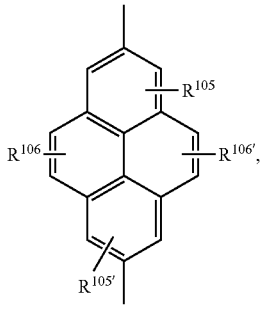 (XVp)
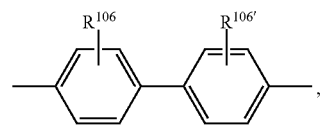 (XVq)
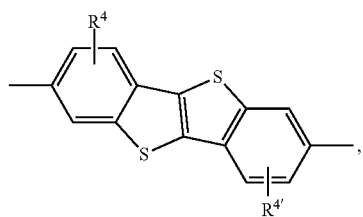 (XVr)

wherein
X¹' is S, O, NR¹⁰⁷—, —Si(R¹¹⁷)(R¹¹⁷')—, —Ge(R¹¹⁷)(R¹¹⁷')—, —C(R¹⁰⁸)(R¹⁰⁹)—, —C(=O)—, C(=CR¹⁰⁴R¹⁰⁴')—, or other heteroaryl groups as depicted, R³ and R³' are independently of each other hydrogen, halogen, halogenated $C_1$-$C_{25}$alkyl, cyano, $C_1$-$C_{25}$alkyl, which are optionally interrupted by one or more oxygen or sulphur atoms; $C_7$-$C_{25}$arylalkyl, or $C_1$-$C_{25}$alkoxy;

R¹⁰⁴ and R¹⁰⁴' are independently of each other hydrogen, cyano, COOR¹⁰³, a $C_1$-$C_{25}$alkyl group, or $C_6$-$C_{24}$aryl or $C_2$-$C_{20}$heteroaryl, R⁴, R⁴', R⁵, R⁵', R⁶, and R⁶' are independently of each other hydrogen, halogen, halogenated $C_1$-$C_{25}$alkyl, cyano, $C_1$-$C_{25}$alkyl, which are optionally interrupted by one or more oxygen or sulphur atoms; $C_7$-$C_{25}$arylalkyl, or $C_1$-$C_{25}$alkoxy;

R⁷, R⁷', R⁹ and R⁹' are independently of each other hydrogen, $C_1$-$C_{25}$alkyl, which are optionally interrupted by one, or more oxygen, or sulphur atoms; or $C_7$-$C_{25}$arylalkyl, R⁸ and R⁸' are independently of each other hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which are optionally interrupted by one or more oxygen or sulphur atoms; or $C_7$-$C_{25}$arylalkyl, R¹¹ and R¹¹' are independently of each other $C_1$-$C_{25}$alkyl group, $C_7$-$C_{25}$arylalkyl, or a phenyl group, which are optionally substituted one to three times with $C_1$-$C_8$alkyl and/or $C_1$-$C_8$alkoxy;

R¹² and R¹²' are independently of each other hydrogen, halogen, cyano, $C_1$-$C_{25}$alkyl, which are optionally interrupted by one, or more oxygen, or sulphur atoms, $C_1$-$C_{25}$alkoxy, $C_2$-$C_{25}$arylalkyl, or

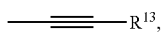=R$^{13}$, wherein R$^{13}$ is a C$_1$-C$_{10}$alkyl group, or a tri(C$_1$-C$_8$alkyl) silyl group;

R$^{104}$ and R$^{104'}$ are independently of each other hydrogen, C$_1$-C$_{18}$alkyl, C$_6$-C$_{10}$aryl, which are optionally substituted by G, or C$_2$-C$_8$ heteroaryl, which is optionally substituted by G, R$^{105}$, R$^{105'}$, R$^{106}$ and R$^{106'}$ are independently of each other hydrogen, halogen, cyano, C$_1$-C$_{25}$alkyl, which are optionally interrupted by one or more oxygen or sulphur atoms; C$_7$-C$_{25}$arylalkyl, or C$_1$-C$_{18}$alkoxy, R$^{107}$ is hydrogen, C$_7$-C$_{25}$arylalkyl, C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$perfluoroalkyl; C$_1$-C$_{25}$alkyl; which is optionally interrupted by —O—, or —S—; or —COOR$^{103}$;

R$^{108}$ and R$^{109}$ are independently of each other H, C$_1$-C$_{25}$alkyl, C$_1$-C$_{25}$alkyl which is substituted by E and/or interrupted by D, C$_7$-C$_{25}$arylalkyl, C$_6$-C$_{24}$aryl, C$_6$-C$_{24}$aryl which is substituted by G, C$_2$-C$_{20}$heteroaryl, C$_2$-C$_{20}$heteroaryl which is substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, or C$_7$-C$_{25}$aralkyl, or R$^{108}$ and R$^{109}$ together form a group of formula =CR$^{110}$R$^{111}$, wherein R$^{110}$ and R$^{111}$ are independently of each other H, C$_1$-C$_{18}$alkyl, C$_1$-C$_{18}$alkyl which is substituted by E and/or interrupted by D, C$_6$-C$_{24}$aryl, C$_6$-C$_{24}$aryl which is substituted by G, or C$_2$-C$_{20}$heteroaryl, or C$_2$-C$_{20}$heteroaryl which is substituted by G, or R$^{108}$ and R$^{109}$ together form a five or six membered ring, which optionally can be substituted by C$_1$-C$_{18}$alkyl, C$_1$-C$_{18}$alkyl which is substituted by E and/or interrupted by D, C$_6$-C$_{24}$aryl, C$_6$-C$_{24}$aryl which is substituted by G, C$_2$-C$_{20}$heteroaryl, C$_2$-C$_{20}$heteroaryl which is substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, or C$_7$-C$_{25}$aralkyl, D is —CO—, —COO—, —S—, —O—, or —NR$^{112'}$—, E is C$_1$-C$_8$thioalkoxy, C$_1$-C$_8$alkoxy, CN, —NR$^{112'}$R$^{113'}$, —CONR$^{112'}$R$^{113'}$, or halogen, G is E, or C$_1$-C$_{18}$alkyl, and R$^{112'}$ and R$^{113'}$ are independently of each other H; C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—, R$^{115}$ and R$^{115'}$ are independently of each other hydrogen, halogen, cyano, C$_1$-C$_{25}$alkyl, which are optionally interrupted by one, or more oxygen, or sulphur atoms, C$_1$-C$_{25}$alkoxy, C$_7$-C$_{25}$arylalkyl, or

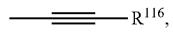=R$^{116}$, wherein R$^{116}$ is a C$_1$-C$_{18}$alkyl group, or a tri(C$_1$-C$_8$alkyl) silyl group;

R$^{117}$ and R$^{117'}$ are independently of each other C$_1$-C$_{25}$alkyl group, C$_7$-C$_{25}$arylalkyl, or a phenyl group, which are optionally substituted one to three times with C$_1$-C$_8$alkyl and/or C$_1$-C$_8$alkoxy;

R$^{118}$, R$^{119}$, R$^{120}$ and R$^{121}$ are independently of each other hydrogen, halogen, halogenated C$_1$-C$_{25}$alkyl, cyano, C$_1$-C$_{25}$alkyl, which are optionally interrupted by one or more oxygen or sulphur atoms; C$_7$-C$_{25}$arylalkyl, or C$_1$-C$_{25}$alkoxy;

R$^{122}$ and R$^{122'}$ are independently of each other hydrogen, C$_6$-C$_{18}$aryl; C$_6$-C$_{18}$aryl which is substituted by C$_1$-C$_{18}$alkyl, or C$_1$-C$_{18}$alkoxy; or C$_1$-C$_{25}$alkyl, which are optionally interrupted by one or more oxygen or sulphur atoms; or C$_7$-C$_{25}$arylalkyl;

R$^{201}$ is selected from hydrogen, a C$_1$-C$_{100}$alkyl group, —COOR$^{103}$, a C$_1$-C$_{100}$alkyl group substituted by one or more halogen atoms, hydroxyl groups, nitro groups, —CN, or C$_6$-C$_{18}$aryl groups and/or interrupted by —O—, —COO—, —OCO— or —S—; a C$_7$-C$_{25}$arylalkyl group, a carbamoyl group, a C$_5$-C$_{12}$cycloalkyl group, which are substituted one to three times with C$_1$-C$_{100}$alkyl and/or C$_1$-C$_{100}$alkoxy, a C$_6$-C$_{24}$aryl group, which are optionally substituted one to three times with C$_1$-C$_{100}$alkyl, C$_1$-C$_{100}$thioalkoxy, and/or C$_1$-C$_{100}$alkoxy; and pentafluorophenyl;

R$^{103}$ and R$^{114}$ are independently of each other C$_1$-C$_{25}$alkyl, which are optionally interrupted by one, or more oxygen, or sulphur atoms, R$^{202}$ and R$^{203}$ may be the same or different and are selected from H, F, —CN, C$_1$-C$_{100}$alkyl, which are optionally interrupted by one or more oxygen, or sulphur atoms; and C$_1$-C$_{100}$alkoxy.

5. The polymer according to claim 1, comprising repeating units of the formula

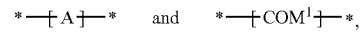

wherein

A is a repeating unit of formula (I), and

COM$^1$- is a repeating unit of formula

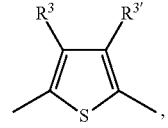

(XIa)

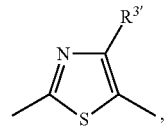

(XId)

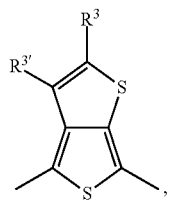

(XIh)

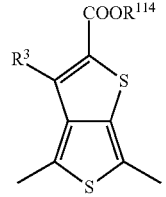

(XIi)

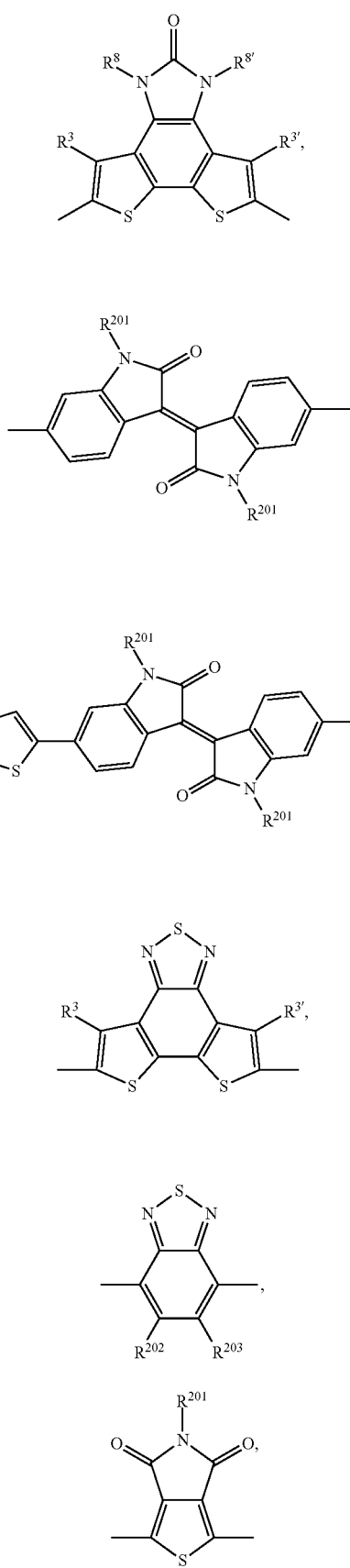
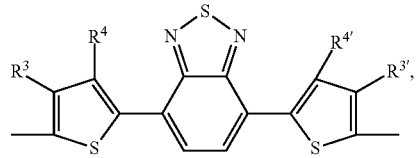
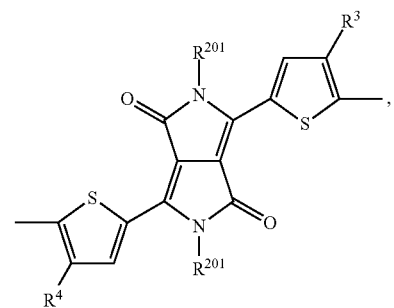
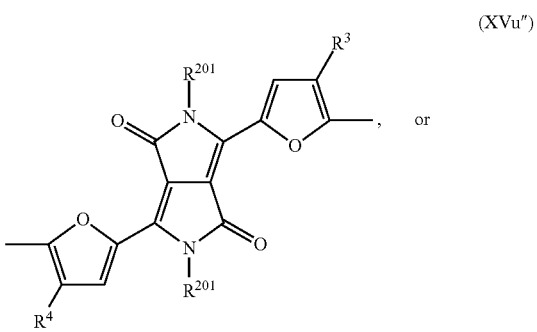
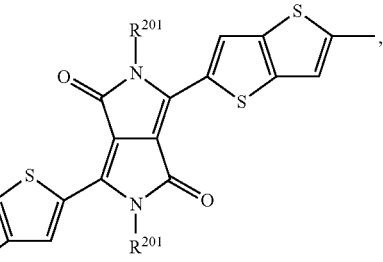
wherein
- $R^3$, $R^{3'}$, $R^4$ and $R^{4'}$ are independently of each other hydrogen, or $C_1$-$C_{25}$alkyl;
- $R^8$ and $R^{8'}$ are independently of each other hydrogen, or $C_1$-$C_{25}$alkyl;
- $R^{114}$ is a $C_1$-$C_{38}$alkyl group;
- $R^{201}$ is a $C_1$-$C_{38}$alkyl group; and
- $R^{202}$ and $R^{203}$ are independently of each other hydrogen or $C_1$-$C_{25}$alkyl.

6. The polymer according to claim 4, which is a polymer of formula

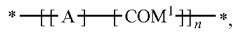 (III)

wherein n is 4 to 1000,

A is a repeating unit of formula

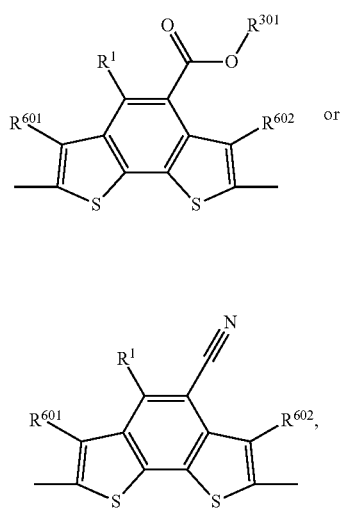

(Ia)

(Ib)

wherein $R^1$ is selected from hydrogen, or $C_1$-$C_{25}$alkyl, $R^{301}$ is $C_1$-$C_{18}$alkyl, phenyl, phenyl, which is substituted by one, or more groups selected from $C_1$-$C_{18}$alkyl, halogen, $OR^{69}$, CN, or $CF_3$; wherein $R^{69}$ is $C_1$-$C_{18}$alkyl, or phenyl;

$R^{601}$ and $R^{602}$ are hydrogen; and

is a group of formula

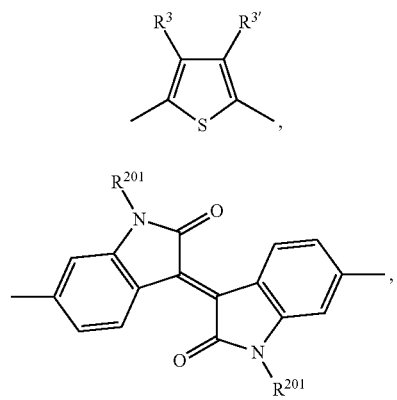

(XIa)

(XVb)

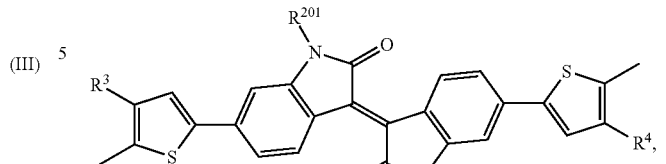 (XVb')

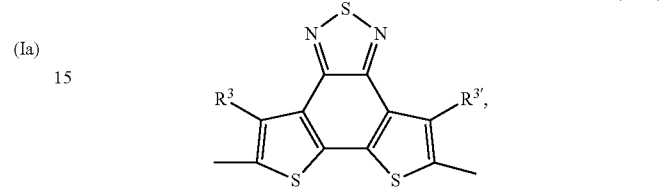 (XVe)

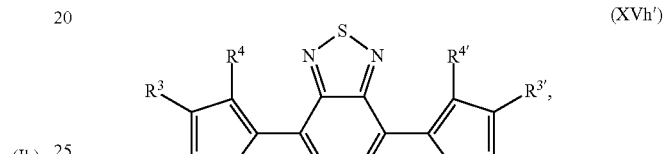 (XVh')

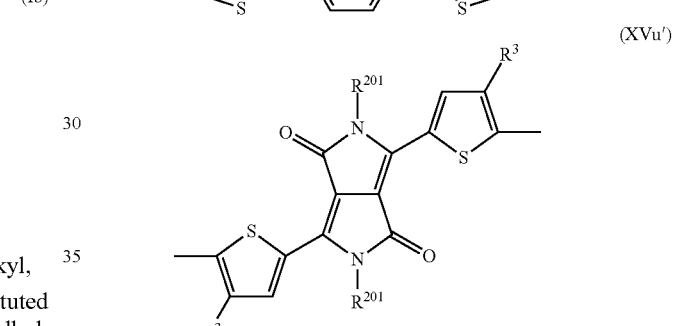 (XVu')

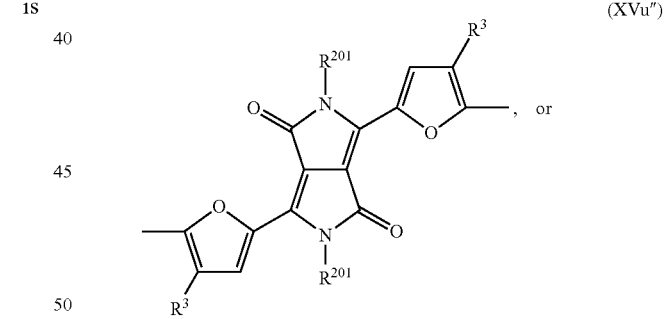 (XVu'')

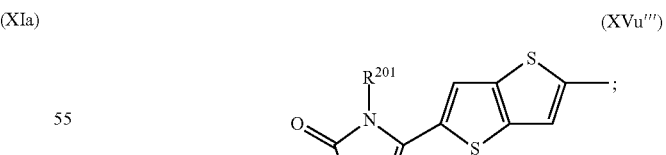 , or (XVu''')

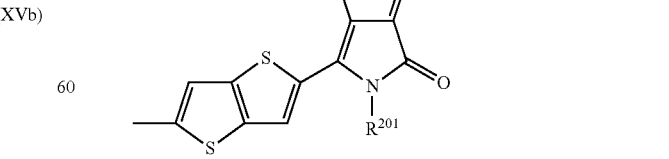 ;

wherein $R^3$, $R^{3'}$, $R^4$ and $R^{4'}$ are independently of each other hydrogen, or $C_1$-$C_{25}$alkyl; and $R^{201}$ is a $C_1$-$C_{38}$alkyl group.

7. The polymer according to claim 5, which is a polymer of the formula
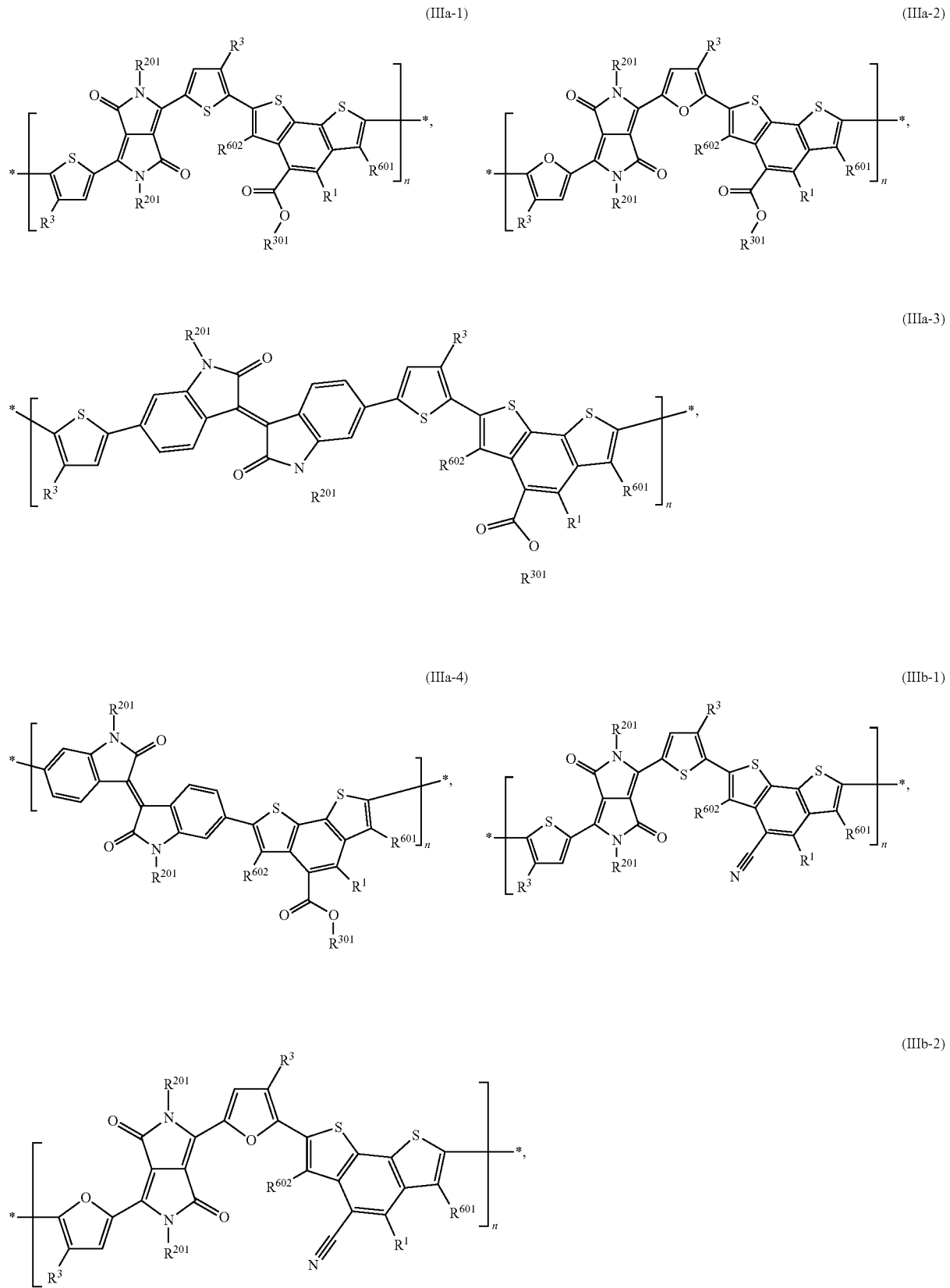

-continued

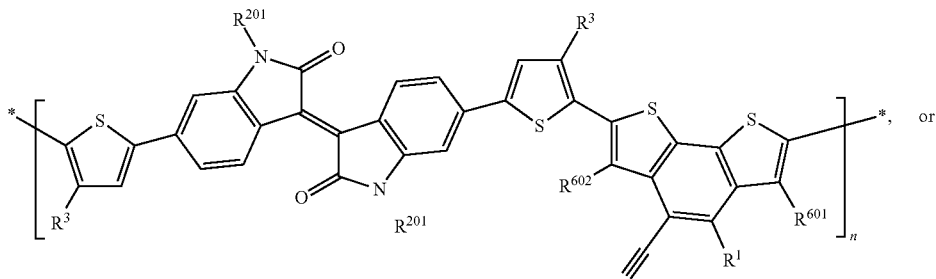

(IIIb-3)

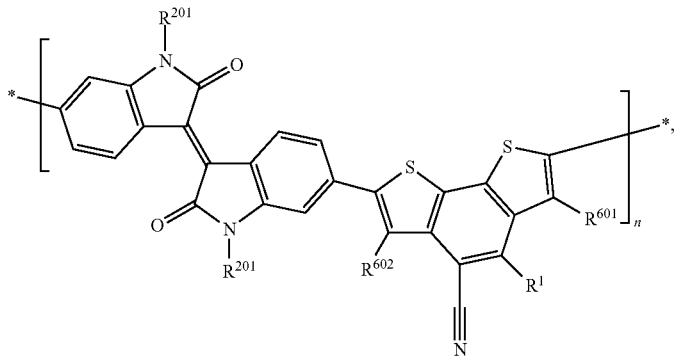

(IIIb-4)

wherein
n is 4 to 1000;
$R^1$ is hydrogen or $C_1$-$C_{100}$alkyl,
$R^3$ and $R^{3'}$ are independently of each other hydrogen or $C_1$-$C_{25}$alkyl;
$R^{201}$ is a $C_1$-$C_{38}$alkyl group,
$R^{301}$ is $C_1$-$C_{18}$alkyl, phenyl, phenyl, which is substituted by one, or more groups selected from $C_1$-$C_{18}$alkyl, halogen, $OR^{69}$, CN, or $CF_3$; wherein $R^{69}$ is $C_1$-$C_{18}$alkyl, or phenyl;
$R^{601}$ and $R^{602}$ are independently of each other hydrogen, or $C_1$-$C_{25}$alkyl.

8. An organic semiconductor material, layer or component, comprising the polymer according to claim 1.

9. An electronic device, comprising the polymer according to claim 1.

10. The electronic device according to claim 9, wherein the electronic device is an organic light emitting diode, an organic photovoltaic device, a photodiode, or an organic field effect transistor.

11. A process for the preparation of an electronic device, which process comprises applying a solution and/or dispersion of the polymer according to claim 1 in an organic solvent to a suitable substrate and removing the solvent.

12. A method comprising incorporating the polymer according to claim 1 into organic light emitting diodes, photovoltaic devices, photodiodes, or organic field effect transistors.

13. A compound of the formula $$X^2-A-X^{2'},$$ (V)

wherein
$X^2$ and $X^{2'}$ are independently of each other halogen, $ZnX^{12}$, —$SnR^{207}R^{208}R^{209}$, wherein $R^{207}$, $R^{208}$ and $R^{209}$ are identical or different and are H or $C_1$-$C_6$alkyl, wherein two radicals optionally form a common ring and these radicals are optionally branched or unbranched and $X^{12}$ is a halogen atom; $SiR^{210}R^{211}R^{212}$, wherein $R^{210}$, $R^{211}$ and $R^{212}$ are identical or different and are halogen, or $C_1$-$C_6$alkyl; —OS(O)$_2$CF$_3$, —OS(O)$_2$-aryl, —OS(O)$_2$CH$_3$, —B(OH)$_2$, —B(OY$^1$)$_2$,

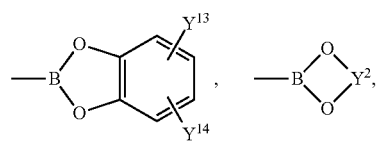

—BF$_4$Na or —BF$_4$K, wherein $Y^1$ is independently in each occurrence a $C_1$-$C_{10}$alkyl group and $Y^2$ is independently in each occurrence a $C_2$-$C_{10}$alkylene group and $Y^{13}$ and $Y^{14}$ are independently of each other hydrogen, or a $C_1$-$C_{10}$alkyl group; and A is a unit of the formula

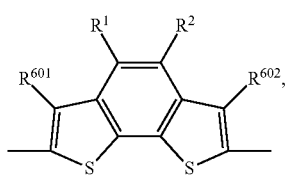

(I)

wherein
$R^1$ is hydrogen, $C_1$-$C_{100}$alkyl, or a group of formula —$SiR^{501}R^{502}R^{503}$;
$R^2$ is —CN, —CF$_3$, a fluorine atom, or a group of the formula

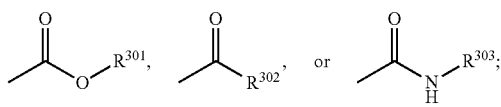

R$^{301}$, R$^{302}$ and R$^{303}$ are independently of each other C$_1$-C$_{18}$alkyl, C$_1$-C$_{18}$alkyl which is substituted by E' and/or interrupted by D', C$_1$-C$_{100}$fluoroalkyl, C$_3$-C$_{12}$cycloalkyl, C$_6$-C$_{24}$aryl, C$_6$-C$_{24}$aryl group, which is substituted by G'; C$_2$-C$_{18}$alkenyl, C$_2$-C$_{18}$alkynyl, C$_7$-C$_{25}$aralkyl, or C$_7$-C$_{25}$aralkyl which is substituted by G'; C$_2$-C$_{20}$heteroaryl, or C$_2$-C$_{20}$heteroaryl, which is substituted by G';

R$^{601}$ and R$^{602}$ are independently of each other H, or C$_1$-C$_{25}$alkyl;

R$^{501}$, R$^{502}$ and R$^{503}$ are independently of each other C$_1$-C$_8$alkyl, C$_6$-C$_{24}$aryl, or C$_7$-C$_{12}$aralkyl;

D' is —CO—, —COO—, —S—, —SO—, —SO$_2$—, —O—, —NR$^{65}$—, —SiR$^{70}$R$^{71}$—, —POR$^{72}$—, —CR$^{63}$=CR$^{64}$—, or —C≡C—, and E' is —OR$^{69}$, —SR$^{69}$, —NR$^{65}$R$^{66}$, —COR$^{68}$, —COOR$^{67}$, —CONR$^{65}$R$^{66}$, —CN, CF$_3$, or halogen, G' is E', C$_1$-C$_{18}$alkyl, or C$_1$-C$_{18}$alkyl which is interrupted by —O—, R$^{63}$ and R$^{64}$ are independently of each other C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—;

R$^{65}$ and R$^{66}$ are independently of each other C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—; or R' and R$^{66}$ together form a five or six membered ring, R$^{67}$ is C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—, R$^{68}$ is H; C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—, R$^{69}$ is C$_6$-C$_{18}$aryl; C$_6$-C$_{18}$aryl, which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—, R$^{70}$ and R$^{71}$ are independently of each other C$_1$-C$_{18}$alkyl, C$_6$-C$_{18}$aryl, or C$_6$-C$_{18}$aryl, which is substituted by C$_1$-C$_{18}$alkyl, and R$^{72}$ is C$_1$-C$_{18}$alkyl, C$_6$-C$_{18}$aryl, or C$_6$-C$_{18}$aryl, which is substituted by C$_1$-C$_{18}$alkyl.

14. A process for the preparation of a polymer of formula $$*\text{—}\!\!+\!\!\text{A}\!\!+\!\!\text{—}\!\!+\!\!\text{COM}^1\!\!+\!\!\text{—}_n\!\!*,\quad \text{(III)}$$

comprising reacting a dihalogenide of formula X$^{10}$-A-X$^{10}$ with an equimolar amount of a diboronic acid or diboronate corresponding to formula $$X^{11}\text{—}\!\!+\!\!\text{COM}^1\!\!+\!\!\text{—}X^{11},$$

or reacting a dihalogenide of formula $$X^{10}\text{—}\!\!+\!\!\text{COM}^1\!\!+\!\!\text{—}X^{10}$$

with an equimolar amount of a diboronic acid or diboronate corresponding to formula X$^{11}$-A-X$^{11}$, wherein X$^{10}$ is halogen, and X$^{11}$ is independently in each occurrence —B(OH)$_2$, —B(OY$^1$)$_2$,

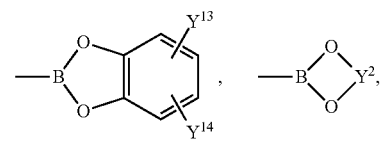

wherein Y$^1$ is independently in each occurrence a C$_1$-C$_{10}$alkyl group and Y$^2$ is independently in each occurrence a C$_2$-C$_{10}$alkylene group and Y$^{13}$ and Y$^{14}$ are independently of each other hydrogen, or a C$_1$-C$_{10}$alkyl group, in a solvent and in the presence of a catalyst; or reacting a dihalogenide of formula X$^{10}$-A-X$^{10}$ with an equimolar amount of an organo tin compound corresponding to formula $$X^{11'}\text{—}\!\!+\!\!\text{COM}^1\!\!+\!\!\text{—}X^{11'},$$

or reacting a dihalogenide of formula $$X^{10}\text{—}\!\!+\!\!\text{COM}^1\!\!+\!\!\text{—}X^{10}$$

with an equimolar amount of an organo tin compound corresponding to formula X$^{11'}$-A-X$^{11'}$, wherein X$^{11'}$ is independently in each occurrence —SnR$^{207}$R$^{208}$R$^{209}$, wherein R$^{207}$, R$^{208}$ and R$^{209}$ are identical or different and are H or C$_1$-C$_6$alkyl, or two of the groups R$^{207}$, R$^{208}$ and R$^{209}$ form a ring and these groups are optionally branched, A and COM$^1$ are as defined in claim 4, X$^{10}$ is as defined above and n is in the range of 4 to 1000.

* * * * *